(12) United States Patent
Jackson et al.

(10) Patent No.: US 10,363,070 B2
(45) Date of Patent: Jul. 30, 2019

(54) PIVOTAL BONE ANCHOR ASSEMBLIES WITH PRESSURE INSERTS AND SNAP ON ARTICULATING RETAINERS

(75) Inventors: Roger P Jackson, Prairie Village, KS (US); James L Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 13/317,969

(22) Filed: Nov. 1, 2011

(65) Prior Publication Data

US 2012/0046700 A1  Feb. 23, 2012

Related U.S. Application Data

(60) Provisional application No. 61/456,163, filed on Nov. 2, 2010.

(51) Int. Cl.
 *A61B 17/70* (2006.01)
(52) U.S. Cl.
 CPC ...... *A61B 17/7037* (2013.01); *A61B 17/7032* (2013.01)
(58) Field of Classification Search
 CPC ............ A61B 17/7035; A61B 17/7037; A61B 17/7046; A61B 17/8685
 USPC ................. 606/246, 250–279, 300–307, 328
 See application file for complete search history.

(56) References Cited

U.S. PATENT DOCUMENTS

| | | | |
|---|---|---|---|
| 2,243,717 A | 5/1941 | Moreira | |
| 2,346,346 A | 4/1944 | Anderson | |
| 2,362,999 A | 11/1944 | Elmer | |
| 2,531,892 A | 11/1950 | Reese | |
| 2,813,450 A | 11/1957 | Dzus | |
| 3,013,244 A | 12/1961 | Rudy | |
| 3,236,275 A | 2/1966 | Smith | |
| 3,604,487 A | 9/1971 | Gilbert | |
| 3,640,416 A | 2/1972 | Temple | |
| 4,033,139 A | 7/1977 | Frederick | |
| 4,041,939 A | 8/1977 | Hall | |

(Continued)

FOREIGN PATENT DOCUMENTS

| | | |
|---|---|---|
| DE | G 92 02 745.8 | 4/1992 |
| DE | G9202745.8 | 4/1992 |

(Continued)

OTHER PUBLICATIONS

*EBI Omega 21 Brochure*, EBI Spine Systems, pub. 1999.

(Continued)

*Primary Examiner* — Lynnsy M Summitt
(74) *Attorney, Agent, or Firm* — Polsinelli PC

(57) ABSTRACT

A polyaxial bone screw assembly includes a threaded shank body having an integral upper portion receivable in a receiver, the receiver having an upper channel for receiving a longitudinal connecting member and a lower cavity cooperating with a lower opening. The shank upper portion expands a retaining member in the receiver cavity to capture the shank upper portion in the receiver. The retaining member and attached shank are pivotable with respect to the receiver until locked in place with respect to the receiver. A pre-assembled receiver, retaining member and compression insert may be popped-on or snapped-on to the shank upper portion prior to or after implantation of the shank into a vertebra.

31 Claims, 28 Drawing Sheets

(56) References Cited

U.S. PATENT DOCUMENTS

| | | |
|---|---|---|
| 4,373,754 A | 2/1983 | Bollfrass et al. |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,067,955 A | 11/1991 | Cotrel |
| 5,092,635 A | 3/1992 | DeLange et al. |
| 5,102,412 A | 4/1992 | Rogozinski |
| 5,129,388 A | 7/1992 | Vignaud et al. |
| 5,147,363 A | 7/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno |
| 5,499,892 A | 3/1996 | Reed |
| 5,501,684 A * | 3/1996 | Schlapfer ............... A61B 17/60 403/90 |
| 5,505,731 A | 4/1996 | Tornier |
| 5,507,745 A | 4/1996 | Logroscino et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A * | 9/1997 | Biedermann ...... A61B 17/7032 606/271 |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,392 A | 11/1997 | Richelsoph |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,735,853 A * | 4/1998 | Olerud ............................ 606/71 |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A * | 4/1999 | Morrison et al. .............. 606/266 |
| RE36,221 E | 6/1999 | Breard et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |

(56) References Cited

U.S. PATENT DOCUMENTS

| | | |
|---|---|---|
| 6,136,002 A | 10/2000 | Shih et al. |
| 6,143,032 A | 11/2000 | Schafer et al. |
| 6,146,383 A * | 11/2000 | Studer et al. ............... 606/308 |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,241,730 B1 | 6/2001 | Alby |
| 6,241,731 B1 * | 6/2001 | Fiz .................... A61B 17/8047 606/295 |
| 6,248,105 B1 | 6/2001 | Schlapfer et al. |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 * | 8/2001 | Barker et al. ............... 606/60 |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,402,757 B1 | 6/2002 | Moore et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 * | 12/2003 | Barker et al. ............... 606/328 |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 * | 4/2004 | Jackson .................... 606/266 |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,001,389 B1 * | 2/2006 | Navarro ............. A61B 17/8047 606/281 |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,066,062 B2 | 6/2006 | Flesher |
| 7,066,937 B2 | 6/2006 | Shluzas |

(56) References Cited

U.S. PATENT DOCUMENTS

| | | |
|---|---|---|
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,160,300 B2 | 1/2007 | Jackson |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2* | 3/2007 | Baynham .......... A61B 17/7035 606/266 |
| 7,207,992 B2 | 4/2007 | Ritland |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2* | 12/2007 | Sasing .......... A61B 17/7037 606/279 |
| 7,314,467 B2 | 1/2008 | Howland |
| 7,316,684 B1 | 1/2008 | Baccelli et al. |
| 7,322,979 B2 | 1/2008 | Crandall et al. |
| 7,322,981 B2* | 1/2008 | Jackson .......... A61B 17/7037 606/266 |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mujwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 8/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,618,444 B2 | 11/2009 | Shluzas |
| 7,621,941 B2 | 11/2009 | Schlapfer et al. |
| 7,625,394 B2 | 12/2009 | Molz, IV et al. |
| 7,625,396 B2* | 12/2009 | Jackson .......... A61B 17/7037 606/266 |
| 7,641,674 B2 | 1/2010 | Young |
| 7,645,294 B2 | 1/2010 | Kalfasetd |
| 7,648,522 B2 | 1/2010 | David |
| 7,658,739 B2 | 2/2010 | Shluzas |
| 7,662,172 B2 | 2/2010 | Warnick |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,497 B2 | 4/2010 | Cordaro et al. |
| 7,695,498 B2 | 4/2010 | Ritland |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,258 B2 | 7/2010 | Biedermann et al. |
| 7,758,618 B2 | 7/2010 | Walder et al. |
| 7,763,057 B2 | 7/2010 | Abdelgany et al. |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,776,067 B2* | 8/2010 | Jackson .......... A61B 17/7032 606/246 |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,819,902 B2 | 10/2010 | Abdelgany et al. |
| 7,833,251 B1 | 11/2010 | Ahlgren et al. |
| 7,857,834 B2 | 12/2010 | Boschert |
| 7,875,065 B2* | 1/2011 | Jackson .................. 606/305 |
| 7,922,748 B2 | 4/2011 | Hoffman |
| 7,947,065 B2* | 5/2011 | Hammill et al. .......... 606/267 |
| 8,021,097 B2 | 9/2011 | Farris et al. |
| 8,021,397 B2* | 9/2011 | Farris et al. ............ 606/269 |
| 8,034,089 B2* | 10/2011 | Matthis et al. ............. 606/306 |
| 8,048,112 B2 | 11/2011 | Suzuki et al. |
| 8,048,126 B2* | 11/2011 | Altarac et al. ............ 606/267 |
| 8,066,744 B2* | 11/2011 | Justis et al. .............. 606/266 |
| 8,133,262 B2* | 3/2012 | Whipple .................. 606/269 |
| 8,137,386 B2* | 3/2012 | Jackson .......... A61B 17/7032 606/266 |
| 8,206,422 B2 | 6/2012 | Hestad et al. |
| 8,277,485 B2* | 10/2012 | Krishna et al. ........... 606/246 |
| 8,361,129 B2 | 1/2013 | Chao |
| 8,430,914 B2 | 4/2013 | Spratt et al. |
| 8,444,681 B2 | 5/2013 | Jackson et al. |
| 8,449,578 B2* | 5/2013 | Keiser .............. A61B 17/7032 606/264 |
| 8,506,609 B2 | 8/2013 | Biedermann et al. |
| 8,591,558 B2* | 11/2013 | Matthis .......... A61B 17/7037 606/306 |

(56) References Cited

U.S. PATENT DOCUMENTS

| | | | |
|---|---|---|---|
| 8,657,858 B2* | 2/2014 | Garamszegi | A61B 17/7037 606/278 |
| 8,771,324 B2* | 7/2014 | Black | A61B 17/8047 606/305 |
| 8,814,913 B2 | 8/2014 | Jackson | |
| 8,986,349 B1 | 3/2015 | German | |
| 9,168,069 B2 | 10/2015 | Jackson | |
| 9,393,047 B2 | 7/2016 | Jackson et al. | |
| 9,439,681 B2 | 9/2016 | Keyer et al. | |
| 9,456,853 B2 | 10/2016 | Jackson | |
| 9,480,517 B2 | 11/2016 | Jackson et al. | |
| 9,504,496 B2 | 11/2016 | Jackson et al. | |
| 9,895,172 B2 | 2/2018 | Biedermann et al. | |
| 9,918,745 B2 | 3/2018 | Jackson | |
| 9,980,753 B2 | 5/2018 | Jackson | |
| 10,172,649 B2 | 1/2019 | Jackson et al. | |
| 10,179,010 B2 | 1/2019 | Jackson et al. | |
| 2001/0001119 A1 | 5/2001 | Lombardo | |
| 2001/0010000 A1 | 7/2001 | Gertzbein | |
| 2001/0029375 A1 | 10/2001 | Betz | |
| 2001/0037111 A1 | 11/2001 | Dixon et al. | |
| 2002/0007184 A1 | 1/2002 | Ogilvie et al. | |
| 2002/0013586 A1 | 1/2002 | Justis et al. | |
| 2002/0022842 A1 | 2/2002 | Horvath et al. | |
| 2002/0026193 A1 | 2/2002 | Barker et al. | |
| 2002/0035366 A1 | 3/2002 | Walder et al. | |
| 2002/0045898 A1 | 4/2002 | Freid et al. | |
| 2002/0058942 A1 | 5/2002 | Biedermann et al. | |
| 2002/0072751 A1 | 6/2002 | Jackson | |
| 2002/0082602 A1 | 6/2002 | Biedermann et al. | |
| 2002/0111626 A1 | 8/2002 | Ralph et al. | |
| 2002/0133159 A1 | 9/2002 | Jackson | |
| 2002/0143341 A1* | 10/2002 | Biedermann et al. | 606/73 |
| 2002/0173789 A1 | 11/2002 | Howland | |
| 2002/0193795 A1 | 12/2002 | Gertzbein et al. | |
| 2003/0023240 A1 | 1/2003 | Amrein et al. | |
| 2003/0023243 A1 | 1/2003 | Biedermann et al. | |
| 2003/0073996 A1 | 4/2003 | Doubler et al. | |
| 2003/0083657 A1 | 5/2003 | Drewry et al. | |
| 2003/0093078 A1 | 5/2003 | Ritland | |
| 2003/0100896 A1 | 5/2003 | Biedermann et al. | |
| 2003/0105460 A1 | 6/2003 | Crandall et al. | |
| 2003/0109880 A1 | 6/2003 | Shirado et al. | |
| 2003/0114852 A1 | 6/2003 | Biedermann et al. | |
| 2003/0125741 A1 | 7/2003 | Biedermann et al. | |
| 2003/0149432 A1 | 8/2003 | Frigg et al. | |
| 2003/0153911 A1 | 8/2003 | Shluzas | |
| 2003/0163133 A1 | 8/2003 | Altarac et al. | |
| 2003/0171749 A1 | 9/2003 | Le Couedic et al. | |
| 2003/0176862 A1 | 9/2003 | Taylor et al. | |
| 2003/0191470 A1 | 10/2003 | Ritland | |
| 2003/0199873 A1 | 10/2003 | Richelsoph | |
| 2003/0208204 A1 | 11/2003 | Bailey et al. | |
| 2003/0216735 A1 | 11/2003 | Altarac et al. | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0006342 A1 | 1/2004 | Altarac et al. | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0078082 A1 | 4/2004 | Lange | |
| 2004/0087949 A1 | 5/2004 | Bono et al. | |
| 2004/0087952 A1 | 5/2004 | Borgstrom et al. | |
| 2004/0092934 A1 | 5/2004 | Howland | |
| 2004/0097933 A1 | 5/2004 | Lourdel et al. | |
| 2004/0116929 A1 | 6/2004 | Barker et al. | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0147929 A1 | 7/2004 | Biedermann et al. | |
| 2004/0158247 A1 | 8/2004 | Sitiso et al. | |
| 2004/0172022 A1 | 9/2004 | Landry et al. | |
| 2004/0176766 A1 | 9/2004 | Shluzas | |
| 2004/0186473 A1 | 9/2004 | Cournoyer et al. | |
| 2004/0210216 A1 | 10/2004 | Farris et al. | |
| 2004/0225289 A1 | 11/2004 | Biedermann et al. | |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2004/0236330 A1 | 11/2004 | Purcell et al. | |
| 2004/0249380 A1 | 12/2004 | Glascott | |
| 2004/0260283 A1 | 12/2004 | Wu et al. | |
| 2004/0267264 A1 | 12/2004 | Konieczynski et al. | |
| 2005/0027296 A1* | 2/2005 | Thramann | A61B 17/7059 606/281 |
| 2005/0033298 A1 | 2/2005 | Hawkes et al. | |
| 2005/0038432 A1 | 2/2005 | Shaolian et al. | |
| 2005/0049593 A1* | 3/2005 | Duong | A61B 17/8047 606/287 |
| 2005/0049708 A1 | 3/2005 | Atkinson et al. | |
| 2005/0055026 A1* | 3/2005 | Biedermann et al. | 606/73 |
| 2005/0065515 A1 | 3/2005 | Jahng | |
| 2005/0065516 A1 | 3/2005 | Jahng | |
| 2005/0070899 A1 | 3/2005 | Doubler et al. | |
| 2005/0080415 A1 | 4/2005 | Keyer et al. | |
| 2005/0085815 A1 | 4/2005 | Harms et al. | |
| 2005/0085816 A1 | 4/2005 | Michelson | |
| 2005/0096652 A1 | 5/2005 | Burton | |
| 2005/0096654 A1 | 5/2005 | Lin | |
| 2005/0107788 A1 | 5/2005 | Beaurain et al. | |
| 2005/0113927 A1 | 5/2005 | Malek | |
| 2005/0124991 A1 | 6/2005 | Jahng | |
| 2005/0131404 A1 | 6/2005 | Mazda et al. | |
| 2005/0131407 A1 | 6/2005 | Sicvol et al. | |
| 2005/0131413 A1 | 6/2005 | O'Driscoll et al. | |
| 2005/0137597 A1 | 6/2005 | Butler et al. | |
| 2005/0143737 A1 | 6/2005 | Pafford et al. | |
| 2005/0143823 A1 | 6/2005 | Boyd et al. | |
| 2005/0149020 A1 | 7/2005 | Jahng | |
| 2005/0149023 A1 | 7/2005 | Ritland | |
| 2005/0154389 A1 | 7/2005 | Selover et al. | |
| 2005/0154390 A1 | 7/2005 | Biedermann et al. | |
| 2005/0154391 A1 | 7/2005 | Doherty et al. | |
| 2005/0159750 A1 | 7/2005 | Doherty | |
| 2005/0165396 A1 | 7/2005 | Fortin et al. | |
| 2005/0165400 A1 | 7/2005 | Fernandez | |
| 2005/0171540 A1 | 8/2005 | Lim et al. | |
| 2005/0171542 A1* | 8/2005 | Biedermann et al. | 606/61 |
| 2005/0171543 A1 | 8/2005 | Timm et al. | |
| 2005/0177157 A1 | 8/2005 | Jahng | |
| 2005/0182401 A1 | 8/2005 | Timm et al. | |
| 2005/0187548 A1 | 8/2005 | Butler et al. | |
| 2005/0187555 A1 | 8/2005 | Biedermann et al. | |
| 2005/0192580 A1 | 9/2005 | Dalton | |
| 2005/0203511 A1 | 9/2005 | Wilson-MacDonald et al. | |
| 2005/0203513 A1 | 9/2005 | Jahng et al. | |
| 2005/0203514 A1 | 9/2005 | Jahng et al. | |
| 2005/0203516 A1 | 9/2005 | Biedermann et al. | |
| 2005/0203517 A1 | 9/2005 | Jahng et al. | |
| 2005/0203518 A1 | 9/2005 | Biedermann et al. | |
| 2005/0203519 A1 | 9/2005 | Harms et al. | |
| 2005/0216001 A1 | 9/2005 | David | |
| 2005/0216003 A1 | 9/2005 | Biedermann et al. | |
| 2005/0228501 A1 | 10/2005 | Miller et al. | |
| 2005/0234450 A1 | 10/2005 | Barker | |
| 2005/0234451 A1 | 10/2005 | Markworth | |
| 2005/0234452 A1 | 10/2005 | Malandain | |
| 2005/0234453 A1 | 10/2005 | Shaolian et al. | |
| 2005/0234454 A1 | 10/2005 | Chin | |
| 2005/0234456 A1 | 10/2005 | Malandain | |
| 2005/0240181 A1 | 10/2005 | Boomer et al. | |
| 2005/0240183 A1 | 10/2005 | Vaughan | |
| 2005/0245930 A1 | 11/2005 | Timm et al. | |
| 2005/0251137 A1 | 11/2005 | Ball | |
| 2005/0251140 A1 | 11/2005 | Shaolian et al. | |
| 2005/0251141 A1 | 11/2005 | Frigg et al. | |
| 2005/0260058 A1 | 11/2005 | Cassagne, III | |
| 2005/0261685 A1 | 11/2005 | Fortin et al. | |
| 2005/0261687 A1 | 11/2005 | Garamszegi et al. | |
| 2005/0267470 A1 | 12/2005 | McBride | |
| 2005/0267471 A1 | 12/2005 | Biedermann et al. | |
| 2005/0267474 A1 | 12/2005 | Dalton | |
| 2005/0273099 A1 | 12/2005 | Baccelli et al. | |

(56) References Cited

U.S. PATENT DOCUMENTS

| | | |
|---|---|---|
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0116677 A1 | 6/2006 | Burd et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | Schumacher |
| 2006/0200123 A1 | 9/2006 | Mueller |
| 2006/0200130 A1 | 9/2006 | Hawkins |
| 2006/0200131 A1 | 9/2006 | Chao et al. |
| 2006/0200133 A1 | 9/2006 | Jackson |
| 2006/0200149 A1 | 9/2006 | Hoy et al. |
| 2006/0212033 A1 | 9/2006 | Rothman |
| 2006/0212034 A1 | 9/2006 | Triplett et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0276787 A1 | 12/2006 | Zubok et al. |
| 2006/0276789 A1* | 12/2006 | Jackson ............ A61B 17/7032 606/916 |
| 2006/0276791 A1 | 12/2006 | Shluzas |
| 2006/0276792 A1 | 12/2006 | Ensign et al. |
| 2006/0282074 A1* | 12/2006 | Renaud ............ A61B 17/7035 606/279 |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |

(56) References Cited

U.S. PATENT DOCUMENTS

| | | |
|---|---|---|
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073291 A1 | 3/2007 | Cordaro et al. |
| 2007/0073293 A1 | 3/2007 | Martz |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1* | 4/2007 | Biedermann et al. .......... 606/61 |
| 2007/0093819 A1 | 4/2007 | Albert |
| 2007/0093826 A1* | 4/2007 | Hawkes ............. A61B 17/7032 606/279 |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1* | 5/2007 | Altarac et al. .................. 606/61 |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jean et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1* | 10/2007 | Schlapfer ............ A61B 17/7035 606/86 A |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0124249 A1 | 11/2007 | Aerrabotu et al. |
| 2007/0260243 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |

(56) References Cited

U.S. PATENT DOCUMENTS

| | | |
|---|---|---|
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0132957 A1* | 6/2008 | Matthis et al. ............... 606/301 |
| 2008/0140075 A1 | 6/2008 | Ensign et al. |
| 2008/0140135 A1 | 6/2008 | Konieczynski et al. |
| 2008/0140136 A1 | 6/2008 | Jackson |
| 2008/0147129 A1* | 6/2008 | Biedermann et al. ........ 606/308 |
| 2008/0154315 A1 | 6/2008 | Jackson |
| 2008/0161859 A1 | 7/2008 | Nilsson |
| 2008/0161863 A1* | 7/2008 | Arnold et al. ................ 606/319 |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0188898 A1 | 8/2008 | Jackson |
| 2008/0195159 A1 | 8/2008 | Kloss et al. |
| 2008/0200956 A1 | 8/2008 | Beckwith et al. |
| 2008/1018889 | 8/2008 | Jackson |
| 2008/0215095 A1 | 9/2008 | Biedermann et al. |
| 2008/0215100 A1* | 9/2008 | Matthis .............. A61B 17/7032 606/309 |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0234761 A1* | 9/2008 | Jackson .............. A61B 17/7037 606/309 |
| 2008/0249570 A1 | 10/2008 | Carson et al. |
| 2008/0249576 A1 | 10/2008 | Hawkes et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1* | 10/2008 | Garamszegi ....... A61B 17/7037 606/305 |
| 2008/0287994 A1 | 11/2008 | Perez-Cruet et al. |
| 2008/0288002 A1 | 11/2008 | Crall et al. |
| 2008/0294202 A1 | 11/2008 | Peterson et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1* | 8/2009 | Aschmann ................... 606/264 |
| 2009/0216280 A1 | 8/2009 | Hutchinson |
| 2009/0240290 A1 | 9/2009 | Choi |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0023061 A1 | 1/2010 | Randol et al. |
| 2010/0030224 A1 | 2/2010 | Winslow et al. |
| 2010/0030271 A1 | 2/2010 | Winslow et al. |
| 2010/0030283 A1 | 2/2010 | King et al. |
| 2010/0036417 A1 | 2/2010 | James et al. |
| 2010/0036420 A1 | 2/2010 | Kalfas et al. |
| 2010/0036422 A1 | 2/2010 | Flynn et al. |
| 2010/0036432 A1 | 2/2010 | Ely |
| 2010/0036433 A1 | 2/2010 | Jackson |
| 2010/0042155 A1 | 2/2010 | Biedermann et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063545 A1 | 3/2010 | Richelsoph |
| 2010/0063546 A1 | 3/2010 | Miller et al. |
| 2010/0063550 A1 | 3/2010 | Felix et al. |
| 2010/0063551 A1 | 3/2010 | Richelsoph |
| 2010/0063553 A1 | 3/2010 | Warnick |
| 2010/0069963 A1 | 3/2010 | Eckman |
| 2010/0069969 A1 | 3/2010 | Ampuero et al. |
| 2010/0087861 A1 | 4/2010 | Lechmann et al. |
| 2010/0087865 A1 | 4/2010 | Biedermann et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |

(56) References Cited

U.S. PATENT DOCUMENTS

| | | | |
|---|---|---|---|
| 2010/0094353 A1 | 4/2010 | Shim et al. | |
| 2010/0100136 A1 | 4/2010 | Won et al. | |
| 2010/0100137 A1* | 4/2010 | Justis | A61B 17/7037 606/308 |
| 2010/0106189 A1 | 4/2010 | Miller | |
| 2010/0114170 A1 | 5/2010 | Barrus et al. | |
| 2010/0114171 A1 | 5/2010 | Boachie-Adjei et al. | |
| 2010/0114180 A1 | 5/2010 | Rock et al. | |
| 2010/0125302 A1 | 5/2010 | Hammill, Sr. et al. | |
| 2010/0131017 A1 | 5/2010 | Farris et al. | |
| 2010/0131018 A1 | 5/2010 | Konieczynski et al. | |
| 2010/0137918 A1 | 6/2010 | Wilcox et al. | |
| 2010/0137920 A1 | 6/2010 | Hammill, Sr. et al. | |
| 2010/0145390 A1 | 6/2010 | McCarthy et al. | |
| 2010/0152776 A1 | 6/2010 | Keyer et al. | |
| 2010/0152785 A1 | 6/2010 | Forton et al. | |
| 2010/0152787 A1 | 6/2010 | Walsh et al. | |
| 2010/0152788 A1 | 6/2010 | Warnick | |
| 2010/0160965 A1 | 6/2010 | Viker | |
| 2010/0160974 A1 | 6/2010 | Viker | |
| 2010/0160980 A1 | 6/2010 | Walsh et al. | |
| 2010/0168796 A1 | 7/2010 | Eliasen et al. | |
| 2010/0168800 A1 | 7/2010 | Biedermann et al. | |
| 2010/0168801 A1 | 7/2010 | Biedermann et al. | |
| 2010/0174322 A1 | 7/2010 | Abdelgany et al. | |
| 2010/0179603 A1 | 7/2010 | Warnick | |
| 2010/0185247 A1 | 7/2010 | Richelsoph | |
| 2010/0191290 A1 | 7/2010 | Felix | |
| 2010/0198269 A1 | 8/2010 | Taylor et al. | |
| 2010/0198270 A1 | 8/2010 | Barker et al. | |
| 2010/0198272 A1 | 8/2010 | Keyer et al. | |
| 2010/0204735 A1 | 8/2010 | Gephart et al. | |
| 2010/0222822 A1 | 9/2010 | Farris et al. | |
| 2010/0228293 A1 | 9/2010 | Courtney et al. | |
| 2010/0234891 A1 | 9/2010 | Freeman et al. | |
| 2010/0234902 A1 | 9/2010 | Biedermann et al. | |
| 2010/0241170 A1 | 9/2010 | Cammisa et al. | |
| 2010/0249846 A1 | 9/2010 | Simonson | |
| 2010/0249856 A1 | 9/2010 | Iott et al. | |
| 2010/0256681 A1 | 10/2010 | Hammer et al. | |
| 2010/0256682 A1 | 10/2010 | Fallin et al. | |
| 2010/0256686 A1* | 10/2010 | Fisher | A61B 17/8047 606/286 |
| 2010/0262195 A1* | 10/2010 | Jackson | 606/305 |
| 2010/0262196 A1 | 10/2010 | Barrus et al. | |
| 2010/0274288 A1 | 10/2010 | Prevost et al. | |
| 2010/0305621 A1 | 12/2010 | Wang et al. | |
| 2011/0040338 A1 | 2/2011 | Jackson | |
| 2011/0077694 A1 | 3/2011 | Biedermann et al. | |
| 2011/0152949 A1 | 6/2011 | Biedermann et al. | |
| 2011/0160778 A1 | 6/2011 | Elsbury | |
| 2011/0196430 A1 | 8/2011 | Walsh et al. | |
| 2011/0213424 A1 | 9/2011 | Biedermann et al. | |
| 2011/0282399 A1 | 11/2011 | Jackson | |
| 2012/0010661 A1* | 1/2012 | Farris et al. | 606/264 |
| 2012/0035670 A1 | 2/2012 | Jackson et al. | |
| 2012/0046699 A1 | 2/2012 | Jones et al. | |
| 2012/0046700 A1 | 2/2012 | Jackson et al. | |
| 2012/0059426 A1 | 3/2012 | Jackson et al. | |
| 2012/0078307 A1 | 3/2012 | Nihalani | |
| 2012/0143266 A1 | 6/2012 | Jackson et al. | |
| 2012/0179212 A1 | 7/2012 | Jackson et al. | |
| 2012/0232598 A1 | 9/2012 | Hestad et al. | |
| 2012/0310284 A1* | 12/2012 | Gerchow | 606/264 |
| 2013/0023941 A1 | 1/2013 | Jackson et al. | |
| 2013/0103098 A1 | 4/2013 | Jackson et al. | |
| 2013/0144346 A1 | 6/2013 | Jackson et al. | |
| 2013/0150852 A1 | 6/2013 | Shluzas et al. | |
| 2013/0211465 A1 | 8/2013 | Savage | |
| 2014/0128927 A1 | 5/2014 | Jackson | |
| 2016/0051290 A1 | 2/2016 | Jackson et al. | |
| 2016/0354121 A1 | 12/2016 | Jackson | |
| 2017/0042586 A1 | 2/2017 | Jackson et al. | |
| 2017/0135729 A1 | 5/2017 | Garamszegi | |
| 2017/0189074 A1 | 7/2017 | Biedermann et al. | |
| 2017/0224386 A1 | 8/2017 | Leff et al. | |
| 2017/0245897 A1 | 8/2017 | Nichols et al. | |
| 2017/0265902 A1 | 9/2017 | Jackson | |
| 2017/0296234 A1 | 10/2017 | Jackson et al. | |
| 2017/0333086 A1 | 11/2017 | Jackson | |
| 2017/0354443 A1 | 12/2017 | Jackson | |
| 2018/0000523 A1 | 1/2018 | Jackson | |
| 2018/0014859 A1 | 1/2018 | Biedermann et al. | |
| 2018/0098795 A1 | 4/2018 | Jackson | |
| 2018/0250036 A1 | 9/2018 | Jackson et al. | |
| 2018/0325560 A1 | 11/2018 | Jackson et al. | |

FOREIGN PATENT DOCUMENTS

| | | |
|---|---|---|
| DE | 4239716 | 8/1994 |
| DE | 4425392 | 11/1995 |
| DE | 195 07 141 | 9/1996 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| EP | 0667127 | 8/1995 |
| EP | 0669109 | 8/1995 |
| EP | 0677277 | 10/1995 |
| EP | 0885598 | 12/1998 |
| EP | 1 121 902 | 8/2001 |
| EP | 1121902 | 8/2001 |
| EP | 1190678 | 3/2002 |
| EP | 1210914 | 6/2002 |
| EP | 1570795 | 2/2005 |
| EP | 1570795 | 9/2005 |
| EP | 1579816 | 9/2005 |
| EP | 1634537 | 3/2006 |
| EP | 1925263 | 5/2008 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 2365345 | 2/2002 |
| GB | 2382304 | 5/2003 |
| JP | 10277070 | 10/1998 |
| JP | 2000325358 | 3/2000 |
| WO | WO 92/03100 | 3/1992 |
| WO | WO 94/10927 | 5/1994 |
| WO | WO 94/26191 | 11/1994 |
| WO | WO 95/01132 | 1/1995 |
| WO | WO9641582 | 12/1996 |
| WO | WO 01/10317 | 2/2001 |
| WO | WO01/10317 | 2/2001 |
| WO | WO2001/45576 | 6/2001 |
| WO | WO02/054966 | 7/2002 |
| WO | WO2002/102259 | 12/2002 |
| WO | WO2003/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |

(56) References Cited

FOREIGN PATENT DOCUMENTS

| WO | WO2006/012088 | 2/2006 |
|----|---------------|--------|
| WO | WO2006/017616 | 2/2006 |
| WO | WO2006/028537 | 3/2006 |
| WO | WO2006/045094 | 4/2006 |
| WO | WO2006/119241 | 11/2006 |
| WO | WO2007/118045 | 10/2007 |
| WO | WO2007/124222 | 11/2007 |
| WO | WO2007/0130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |
| WO | WO2010/017631 | 2/2010 |

OTHER PUBLICATIONS

*Claris Instrumentation Brochure*, G Med, pub. 1997.
*VLS System Variable Locking Screw Brochure*, Interpore Cross International, 1999.
*CD Horizon M8 Multi Axial Screw Spinal System Brochure*, Medtronic Sofamor Danek, no publish date.
*Contour Spinal System Brochure*, Ortho Development, no publish date.
*Xia Spinal System Brochure*, Stryker Howmedica Osteonics, no publish date.
*The Rod Plate System Brochure*, Stryker Howmedica Osteonics, pub. Oct. 1999.
*Silhouette Spinal Fixation System Brochure*, Sulzer Medica Spine-Tech, no publish date.
*SDRS Surgical Dynamics Rod System Brochure*, Surgical Dynamics, pub. 1998-99.
*Versalok Low Back Fixation System Brochure*, Wright Medical Technology, Inc., pub. 1997.
*The Strength of Innovation Advertisement*, Blackstone Medical Inc., no publish date.
*The Moss Miami 6.0mm System Advertisement*, author unknown, no publish date.
*Spine*, Lipcott, Williams & Wilkins, Inc. vol. 24, No. 15, p. 1495 Brochure of Tyco/Healthcae/Surgical Dynamics on Spiral Radius 90D, Publication Date: Sep. 2001, pp. 1-8.
*CD Horizon MB Multi Axial Screw Spinal System* Brochure, Medtronic Sofamor Danek, no publish date.

* cited by examiner

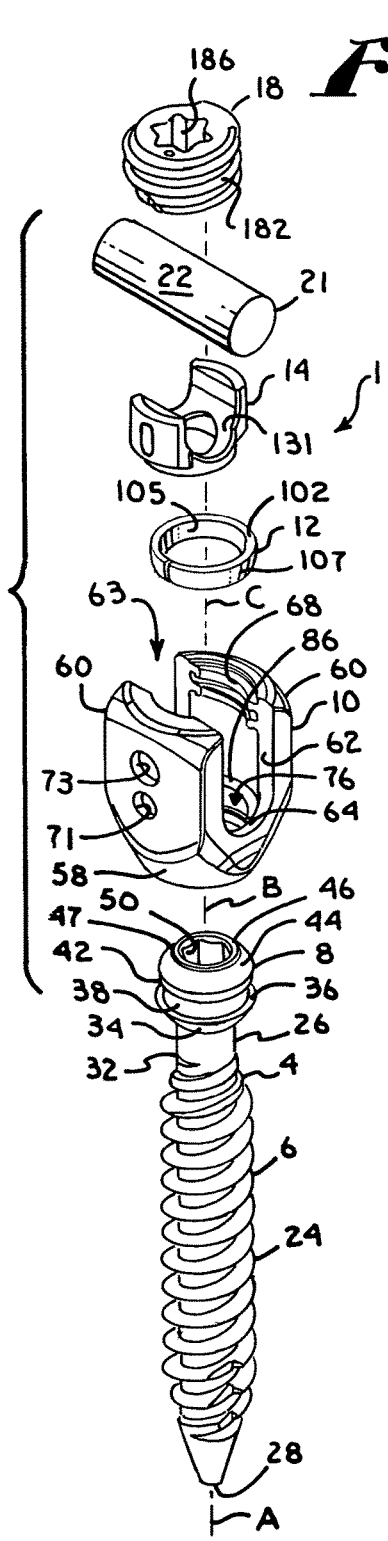
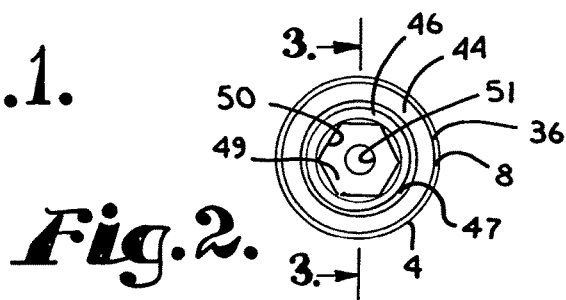
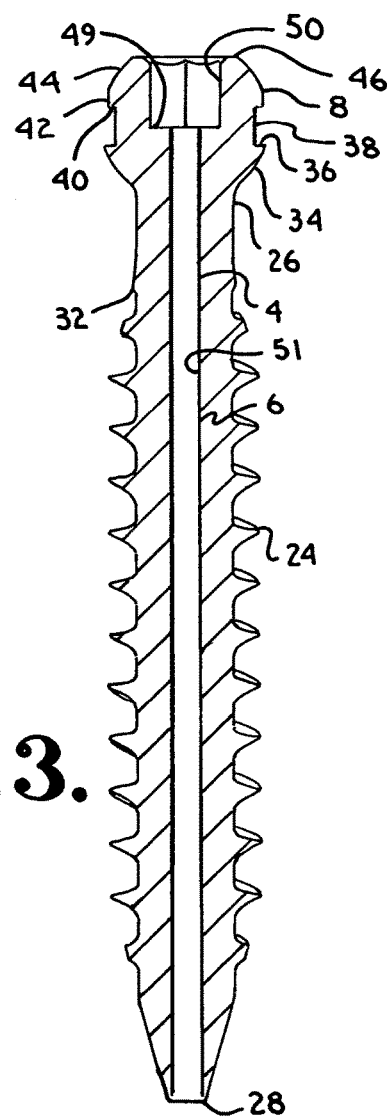
Fig.1.
Fig.2.
Fig.3.

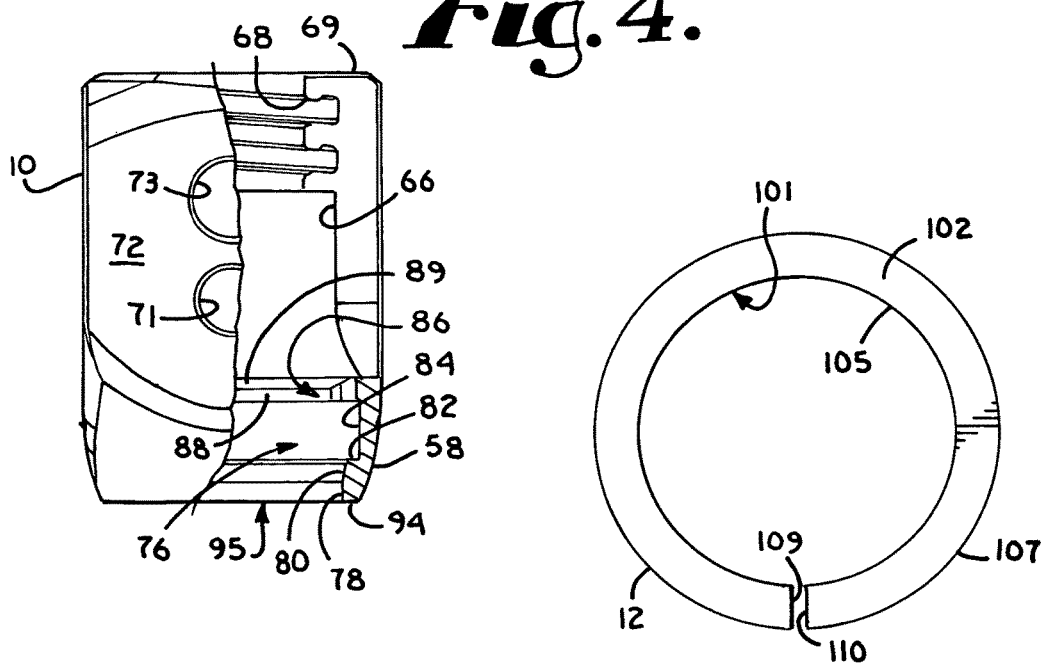
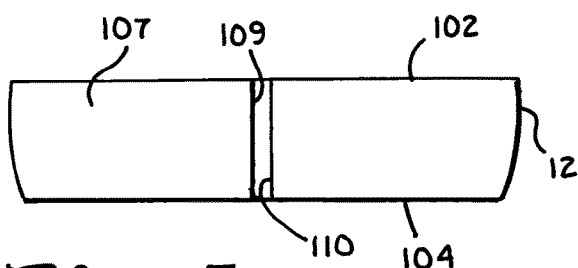
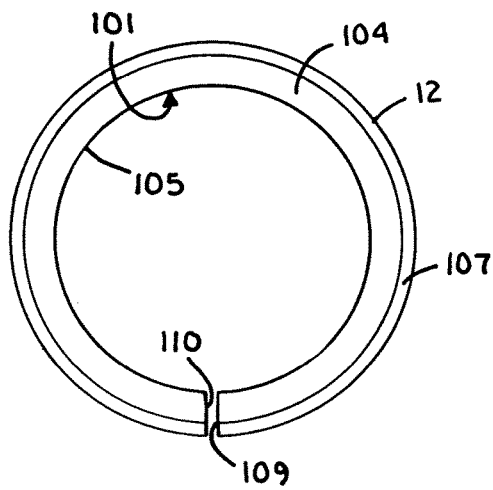

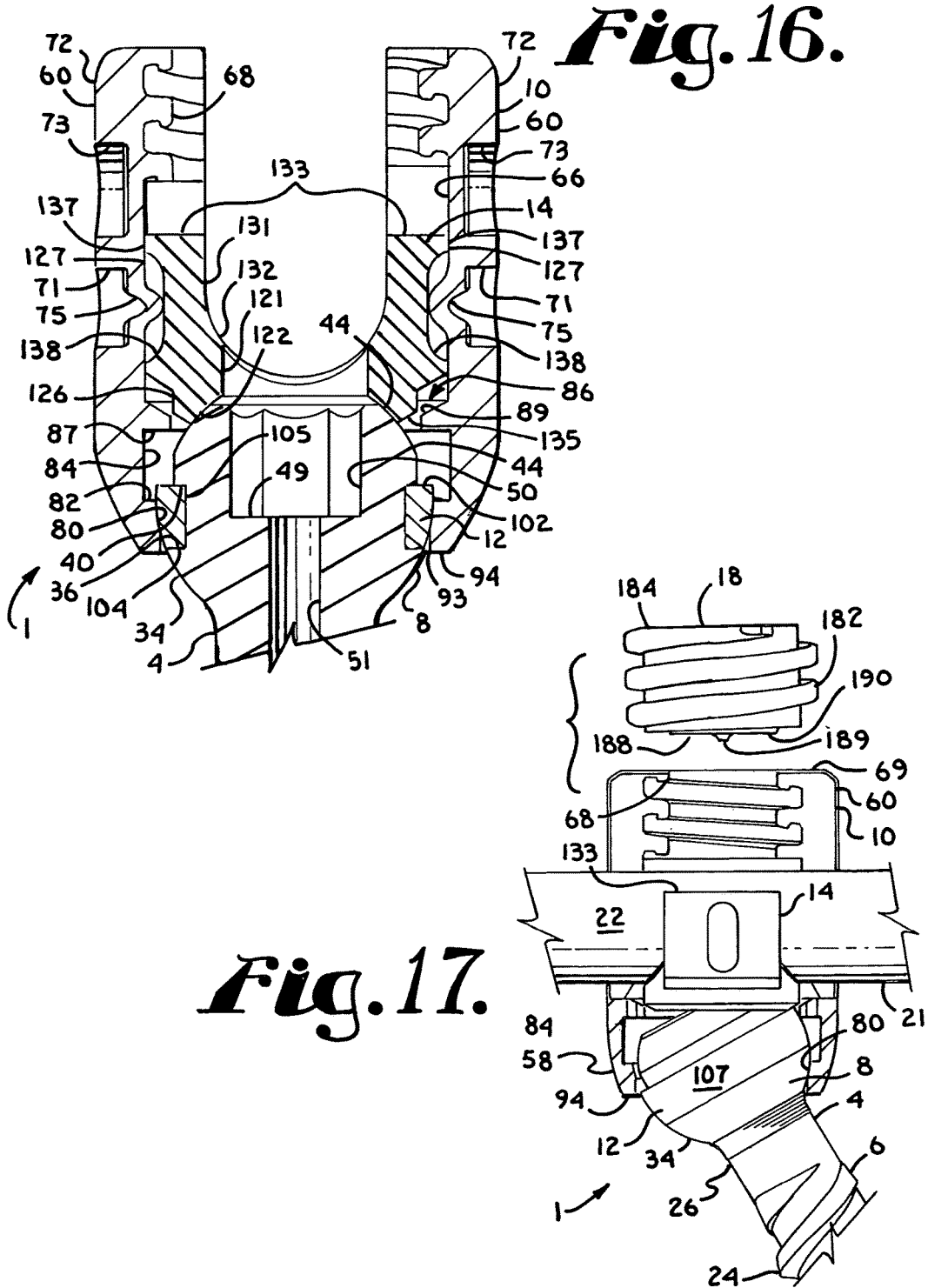

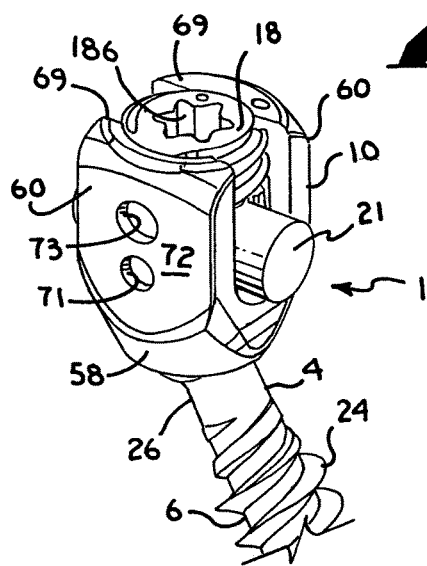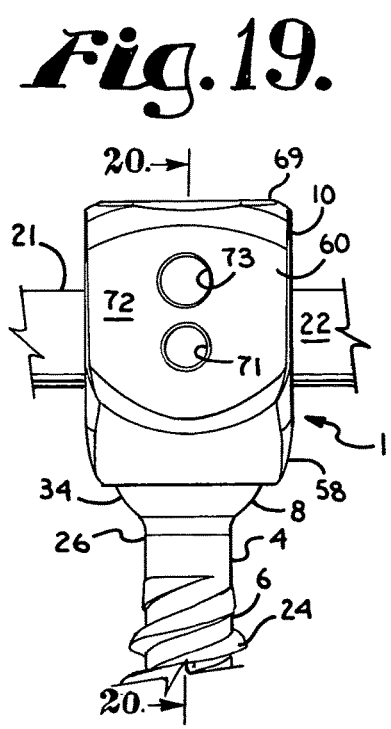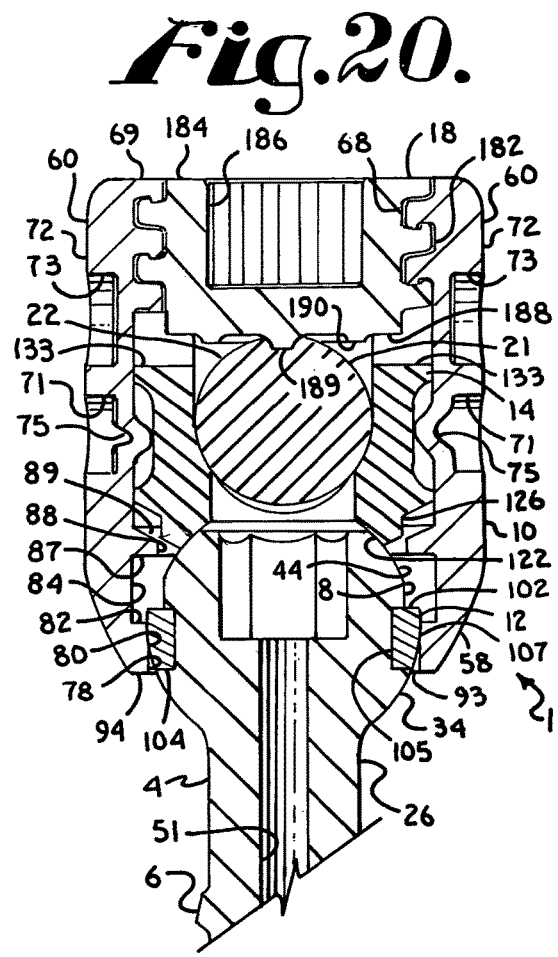

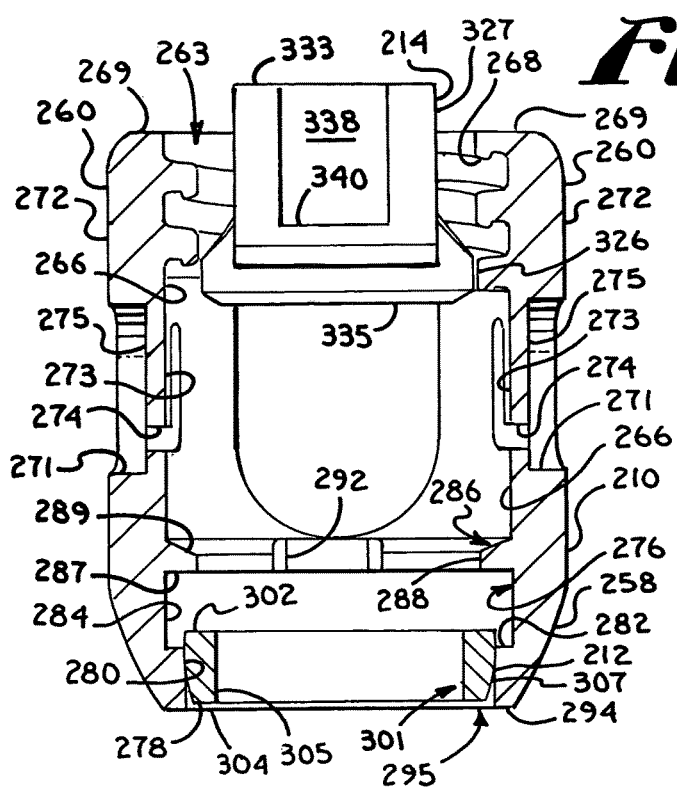
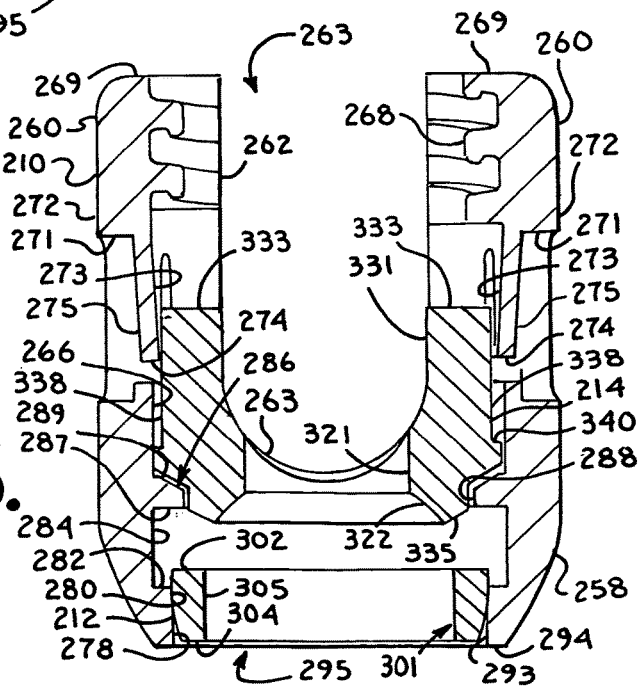

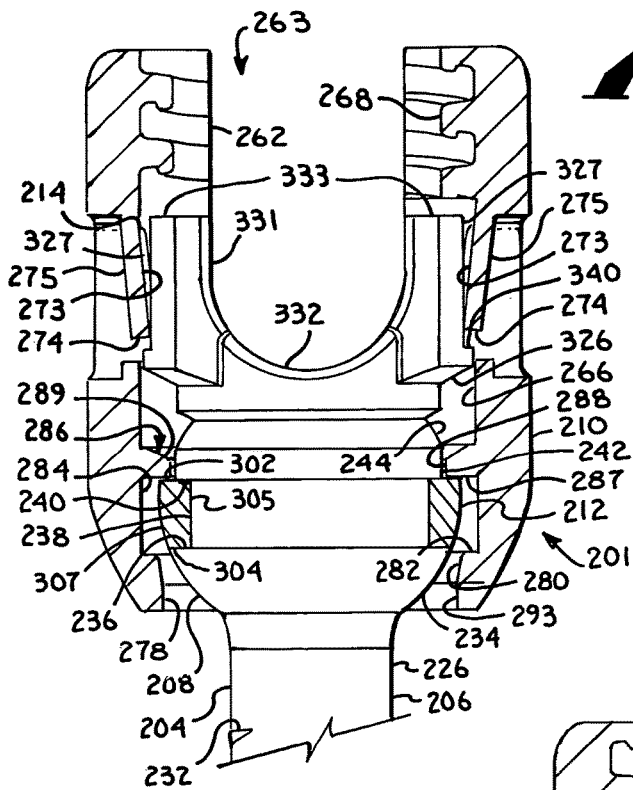
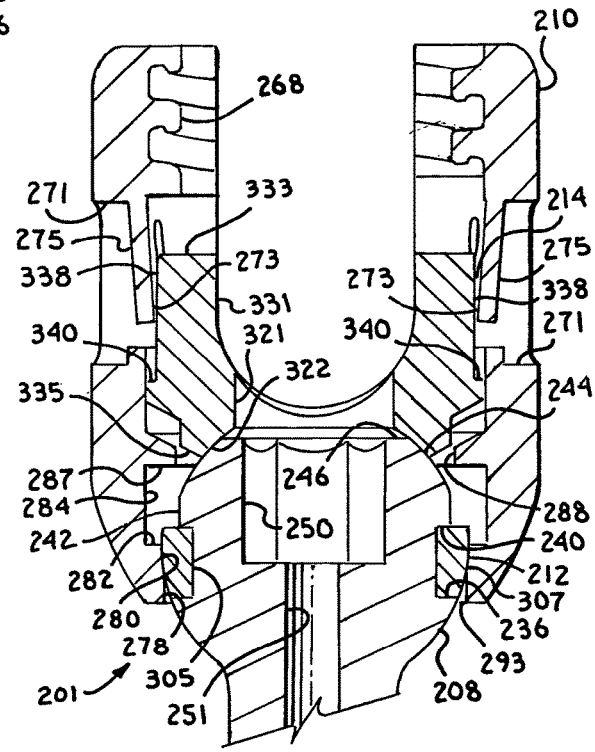

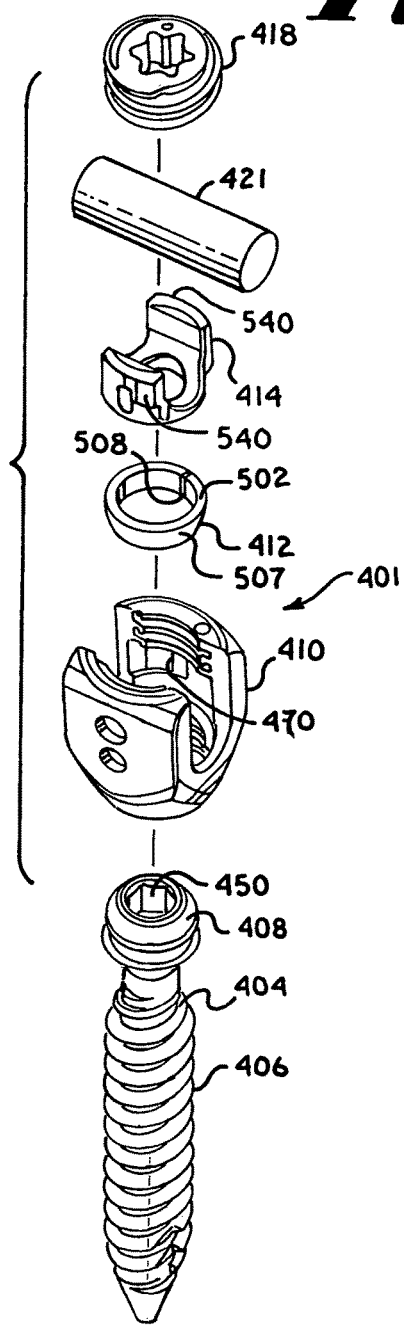
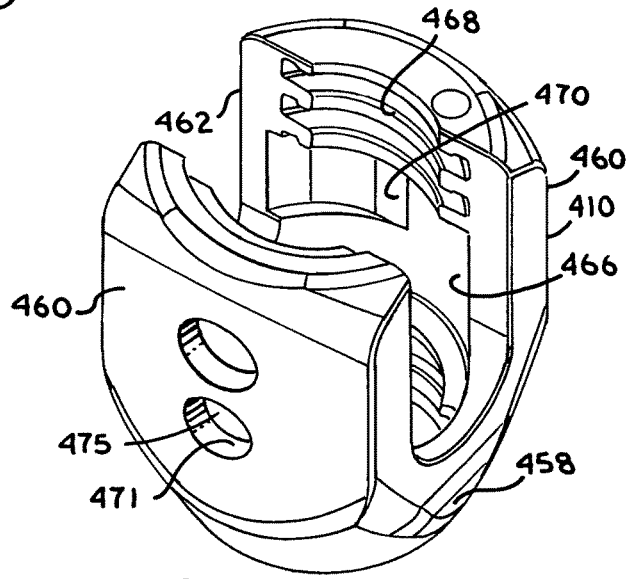
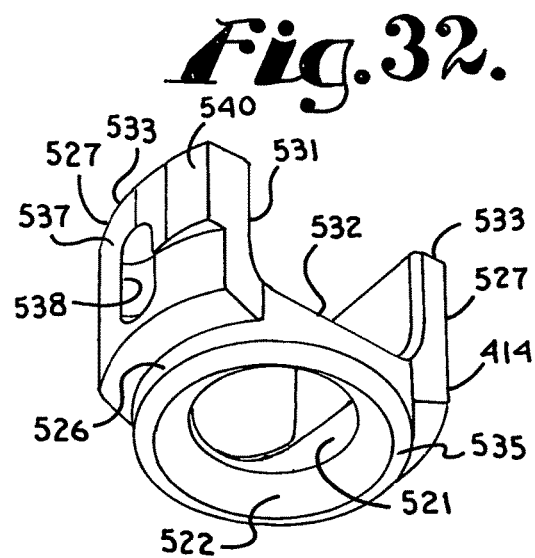
Fig. 30.
Fig. 31.
Fig. 32.

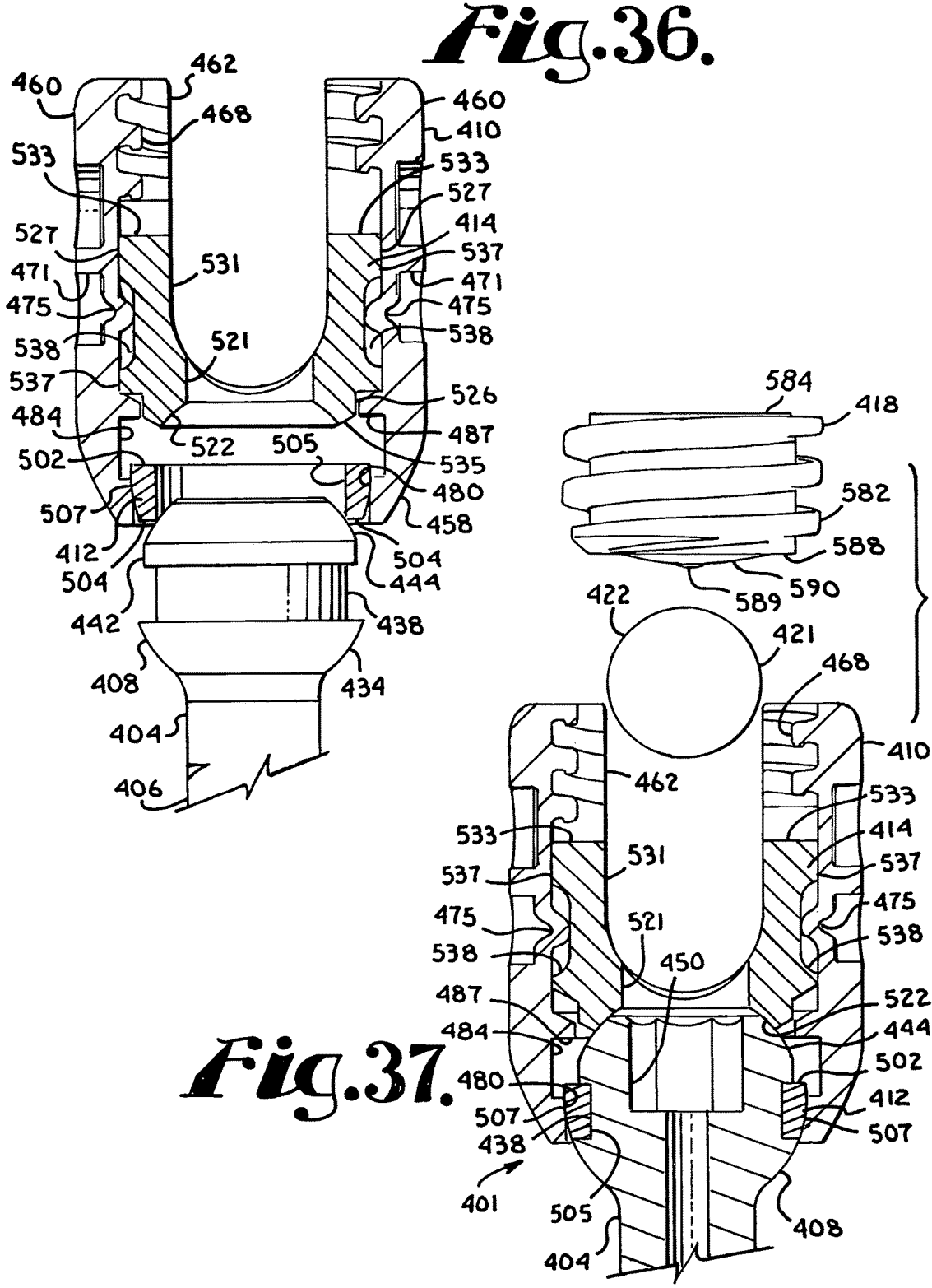

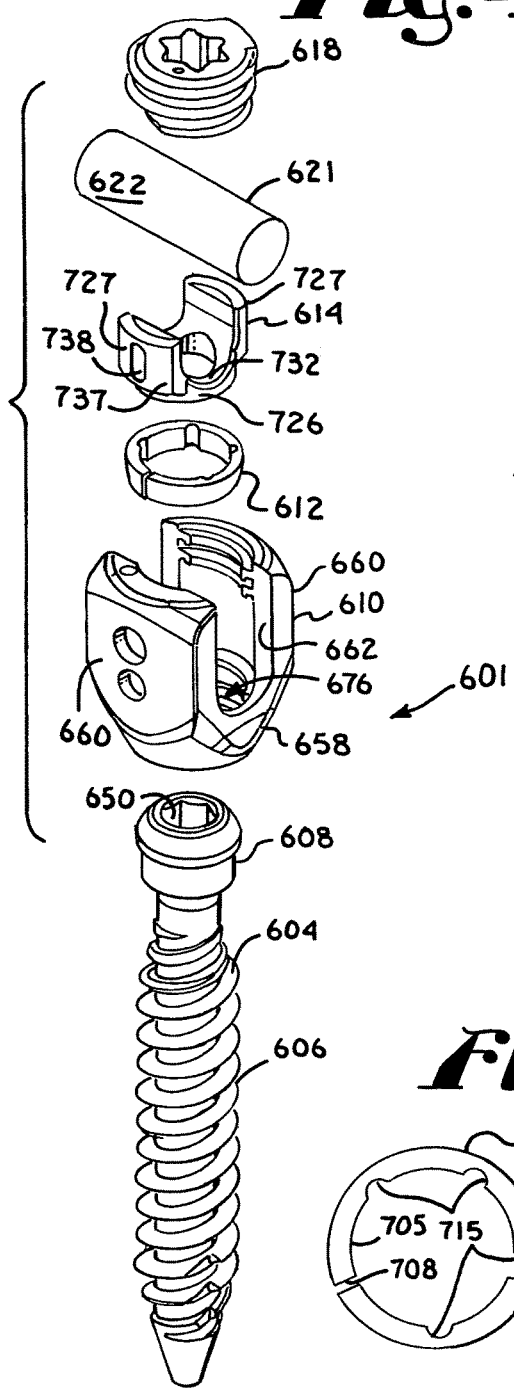
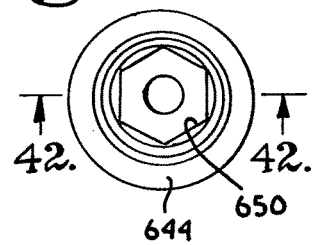
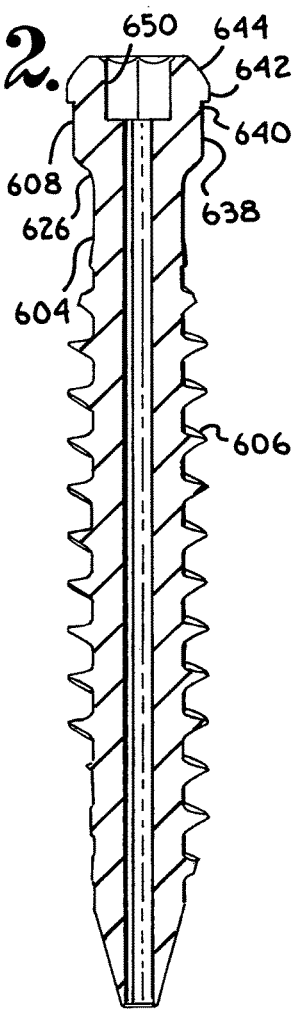
Fig. 40. Fig. 41. Fig. 42. Fig. 43.

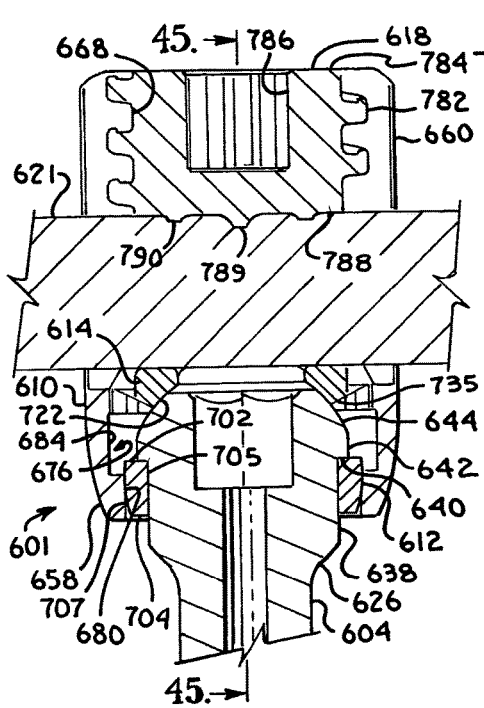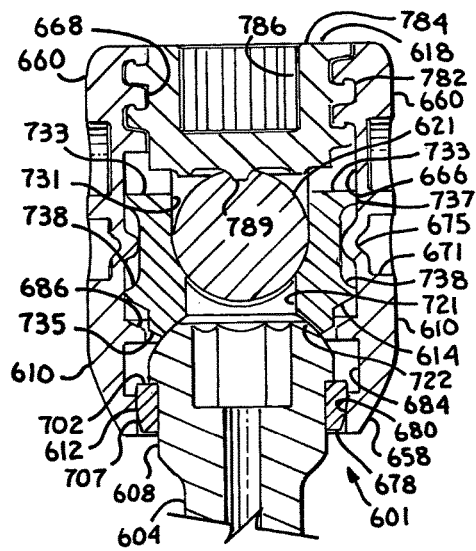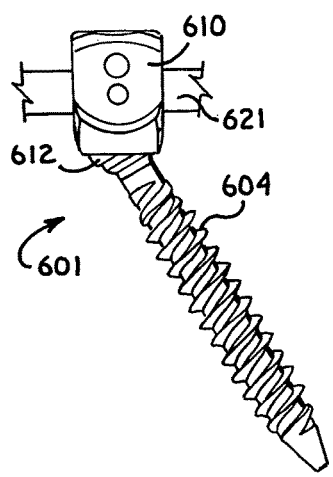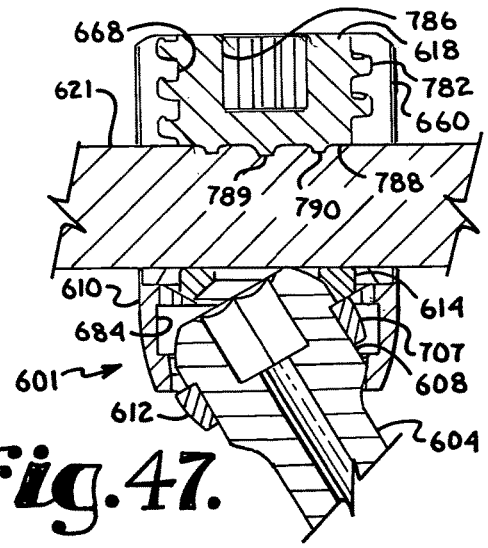

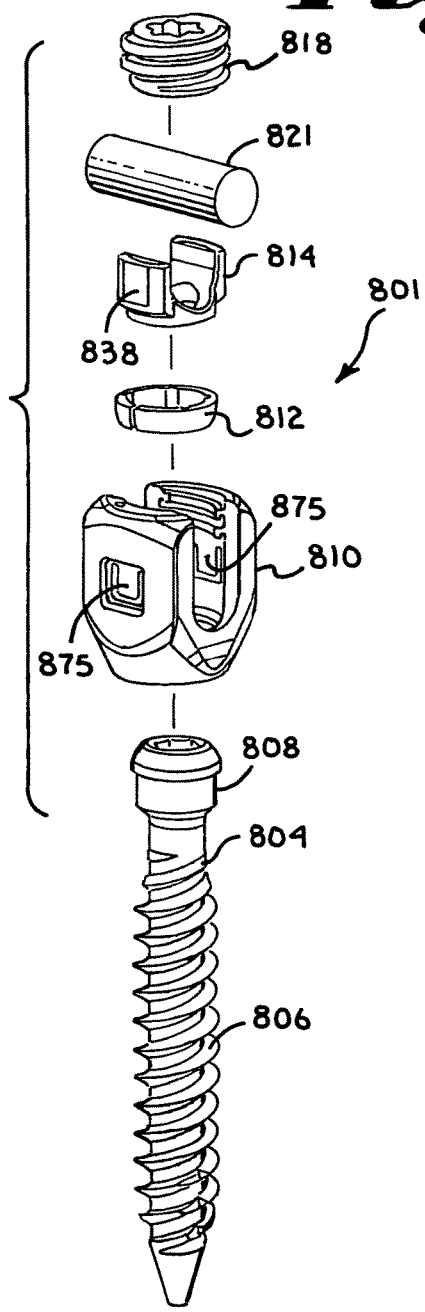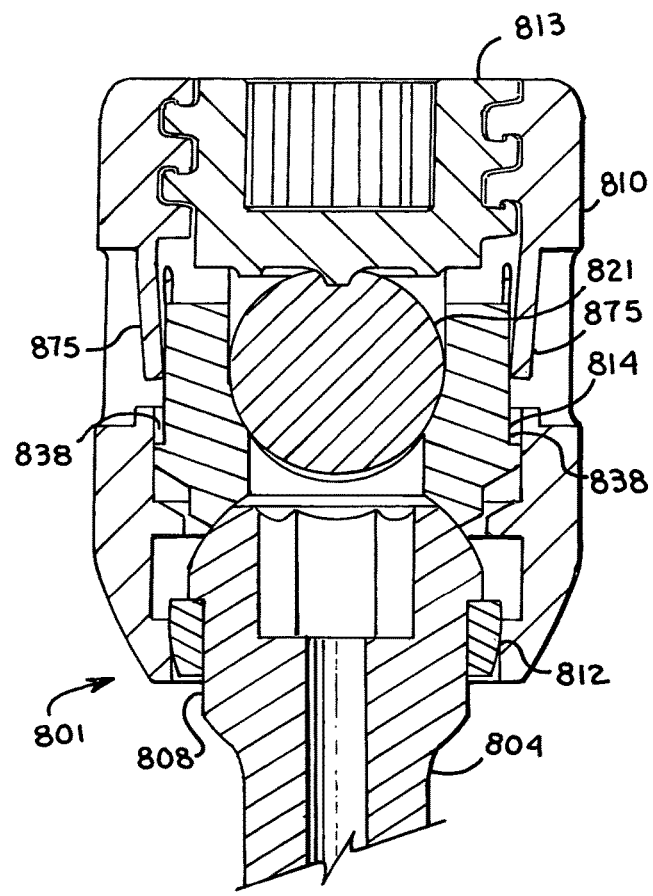
Fig. 48.
Fig. 49.

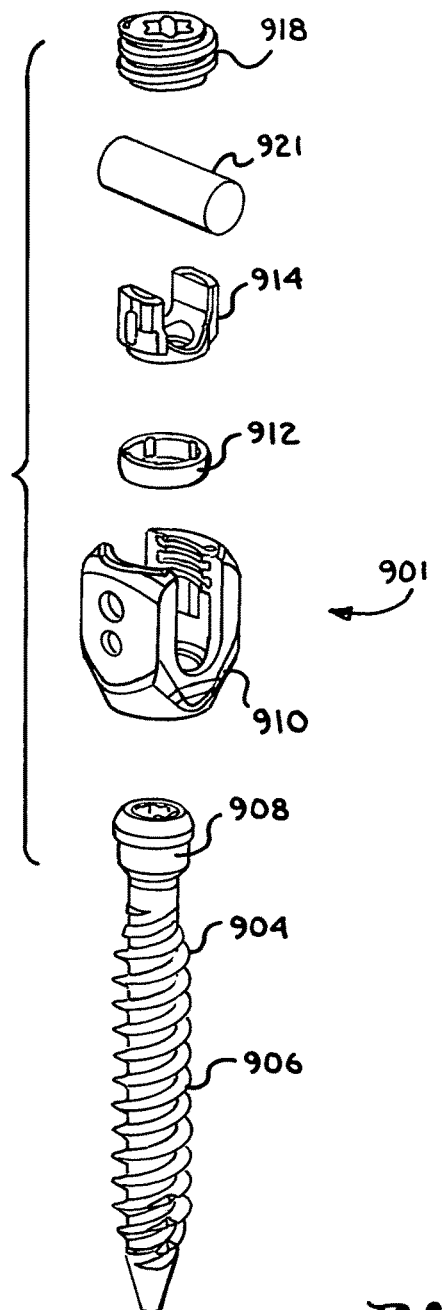
Fig.52.
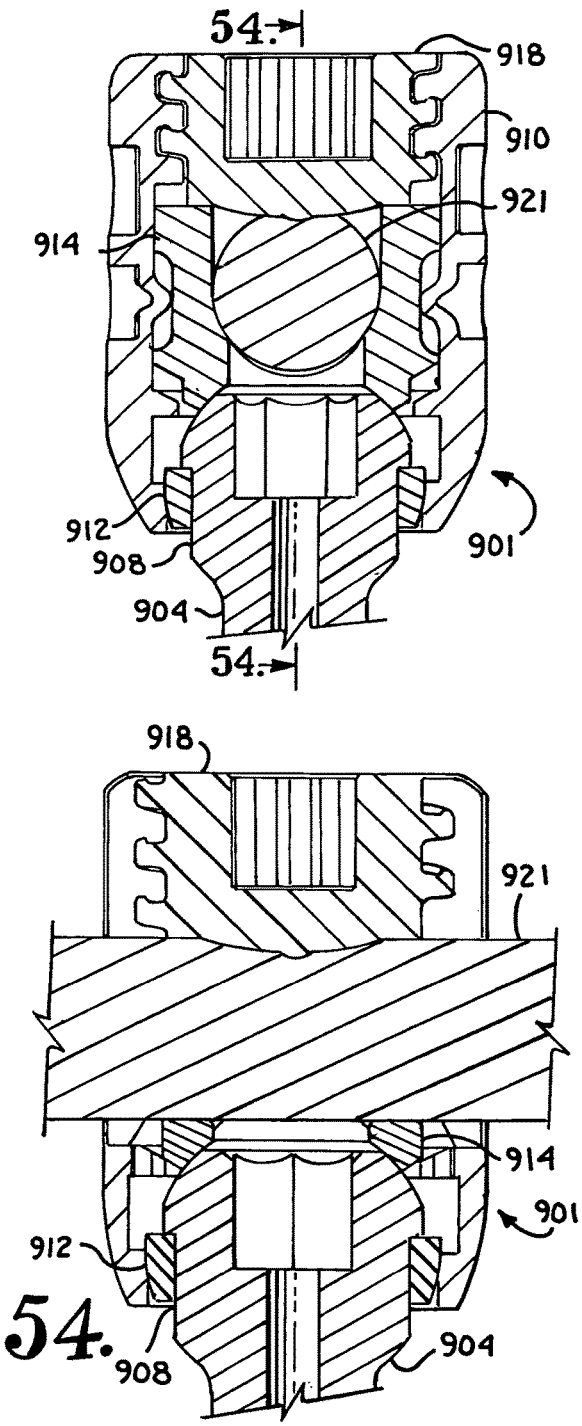
Fig.53
Fig.54.

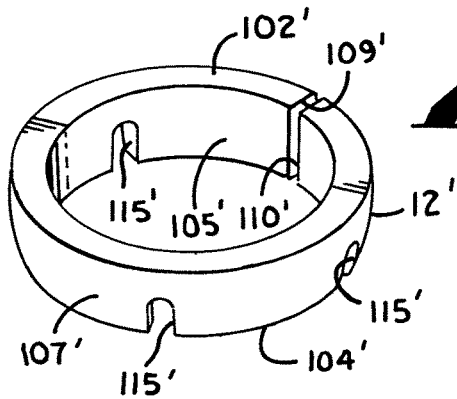
Fig.55.
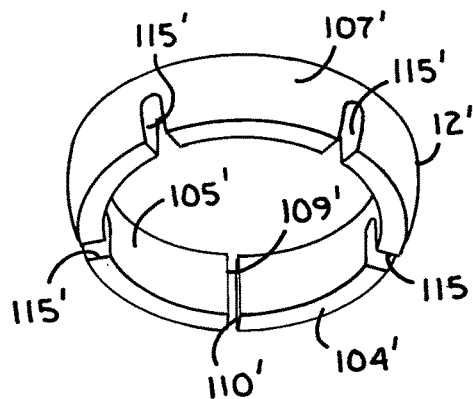
Fig.56.
Fig.57.
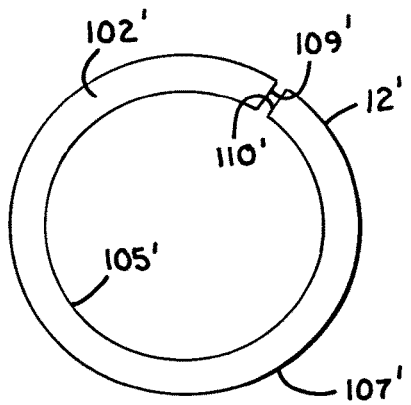
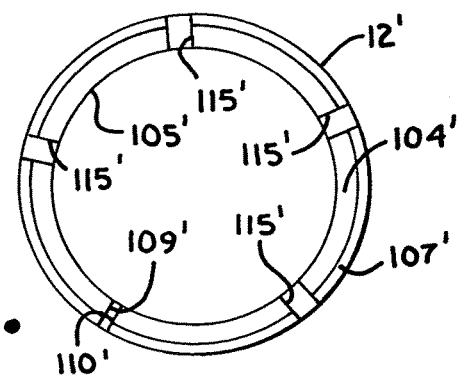
Fig.58.

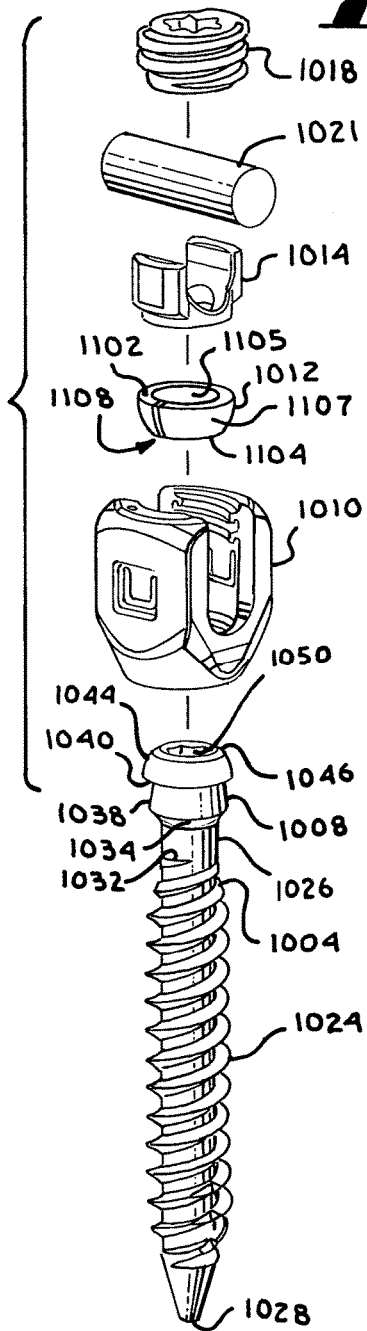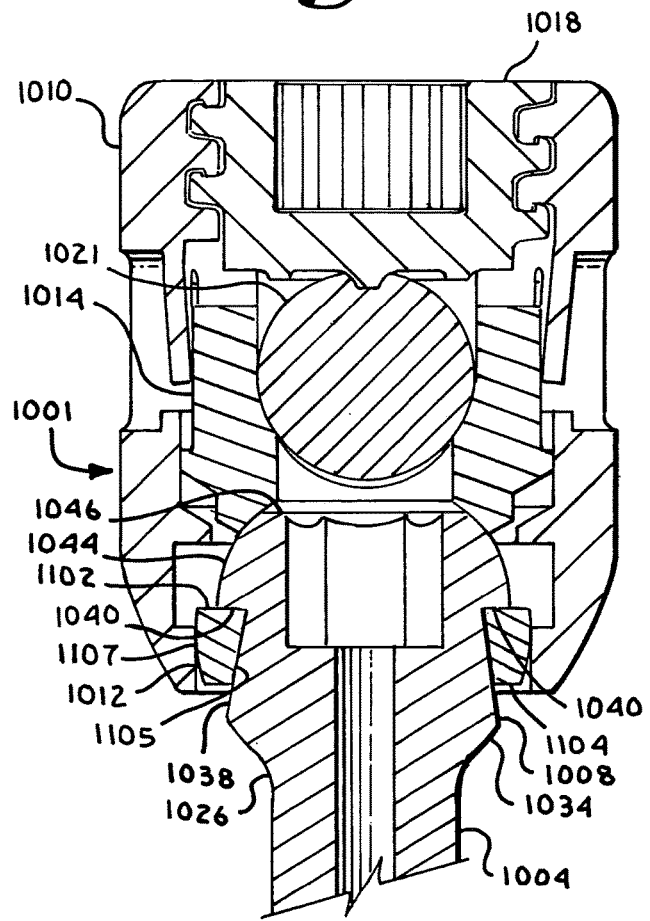

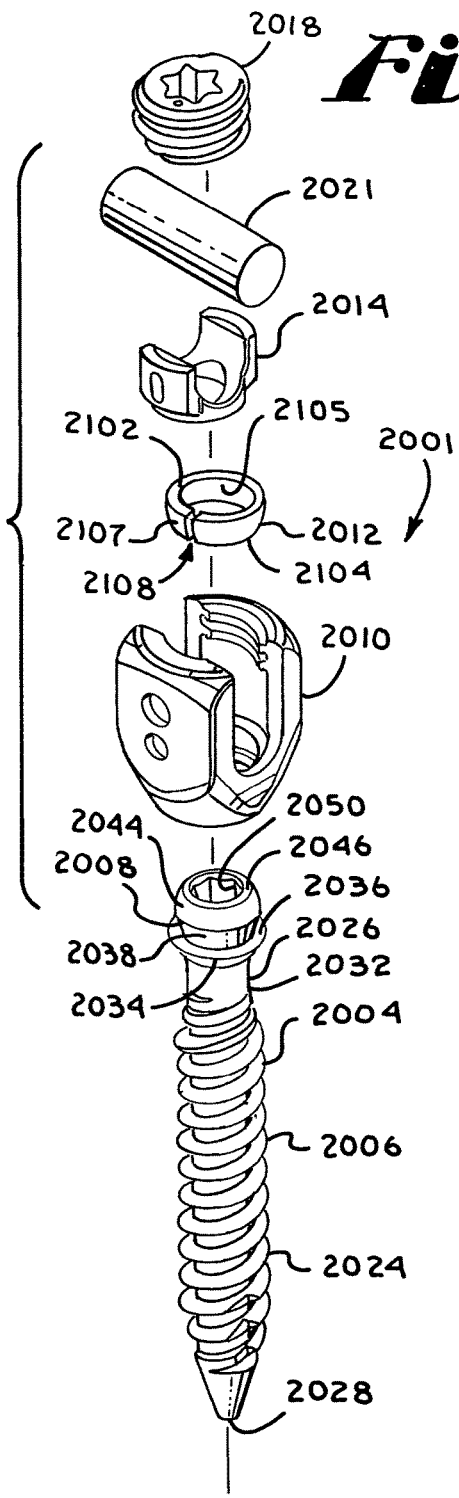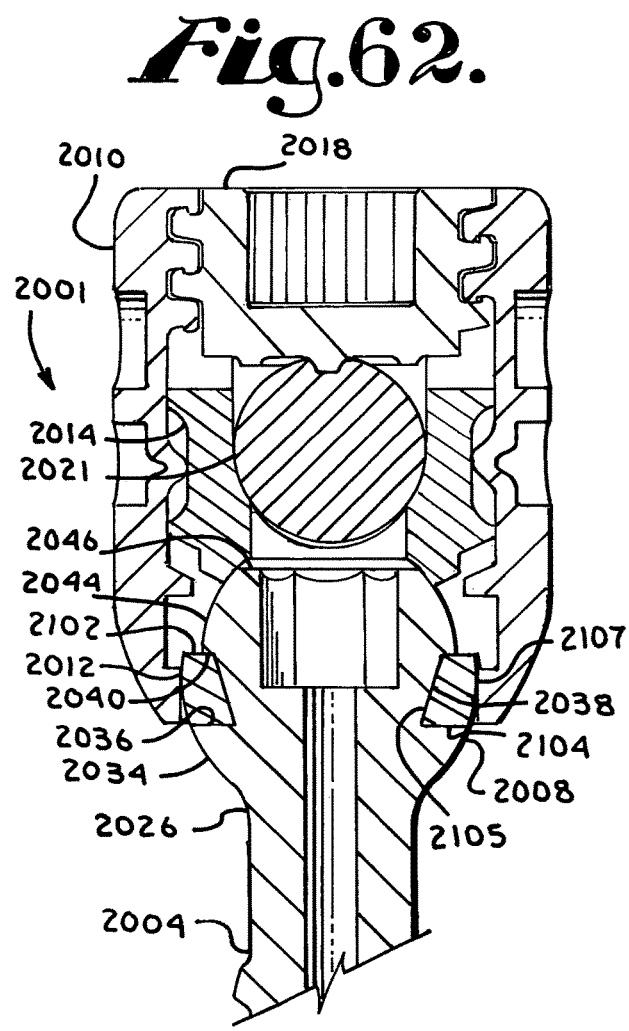

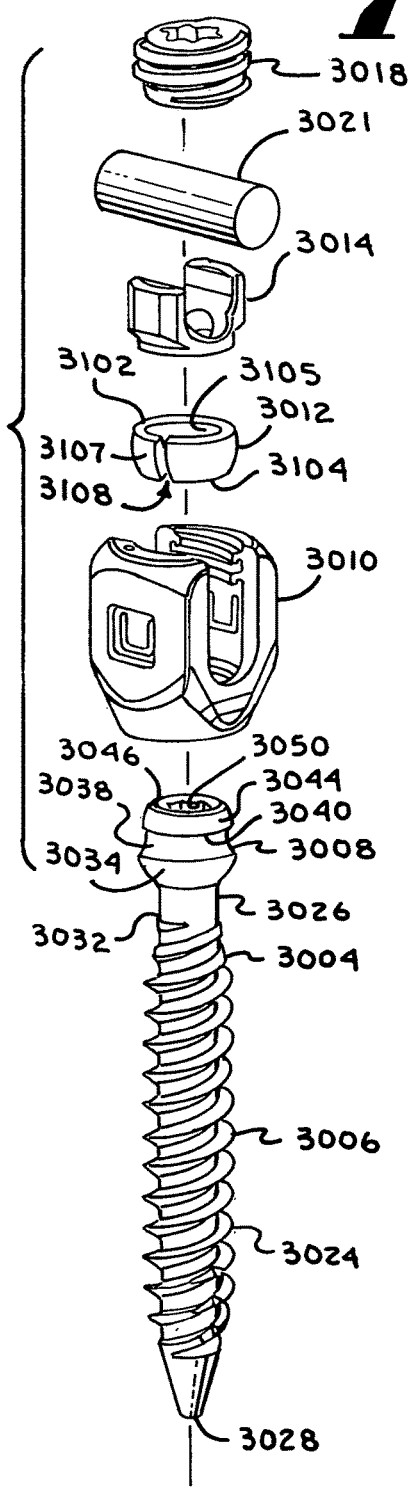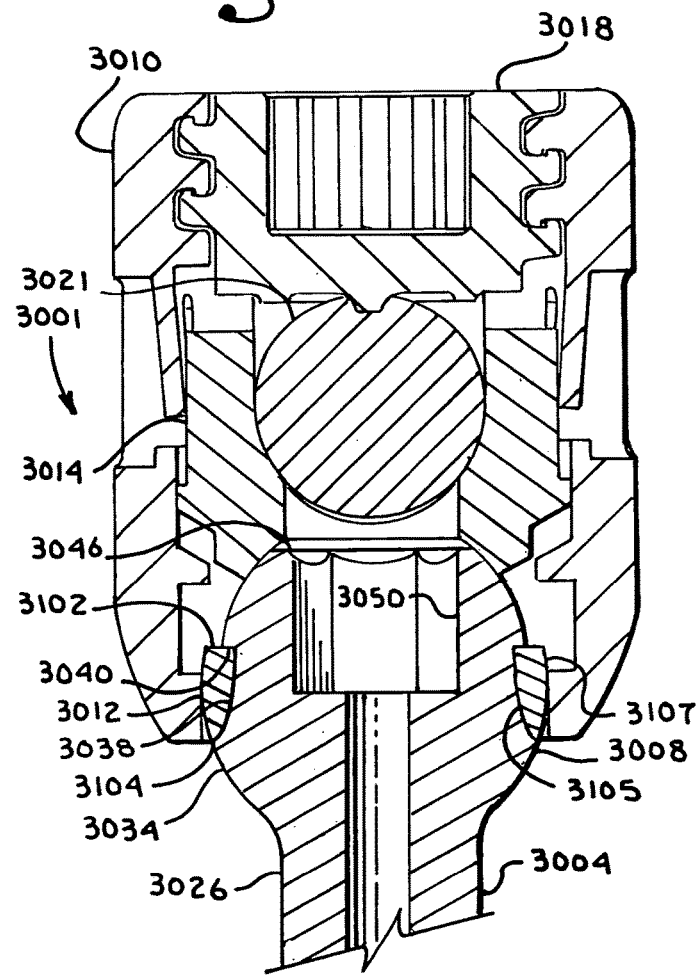
Fig. 63.
Fig. 64.

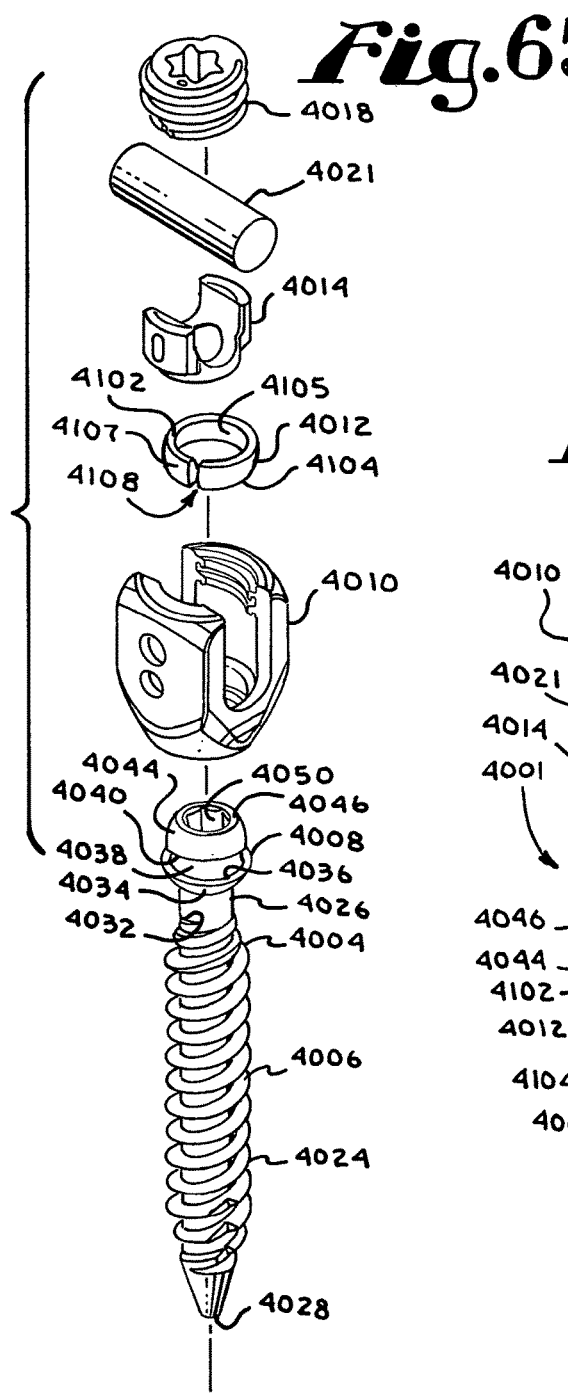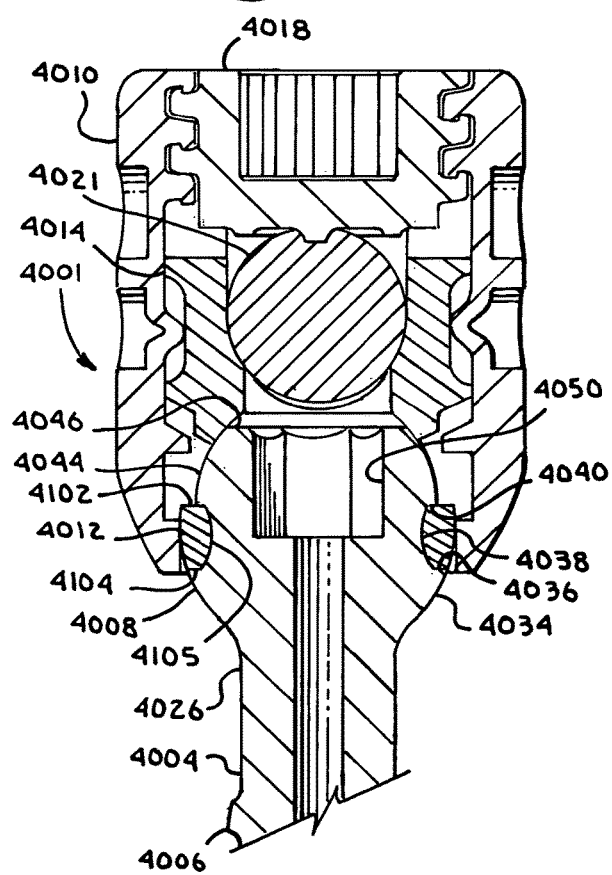

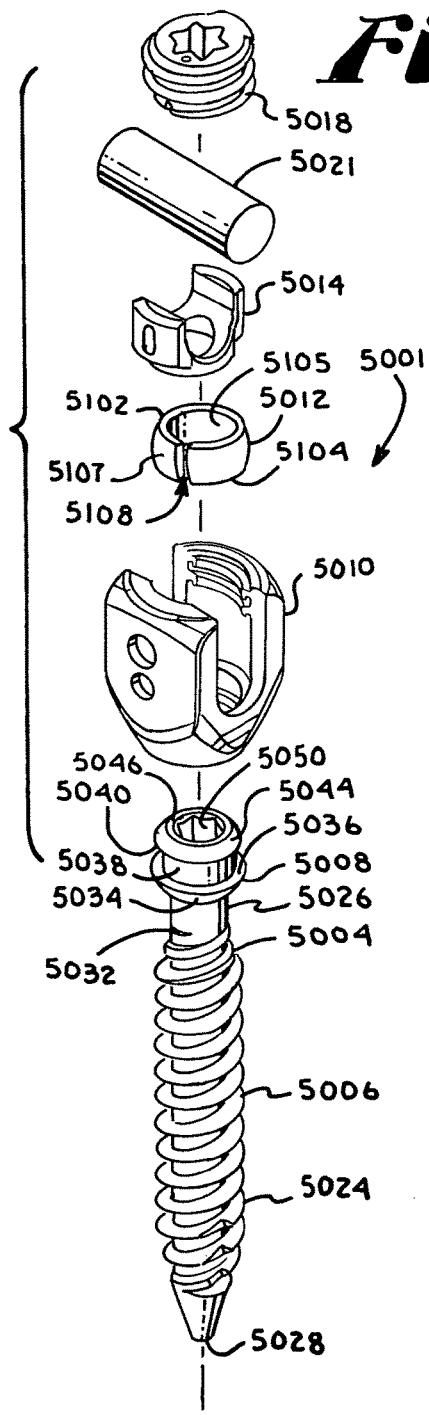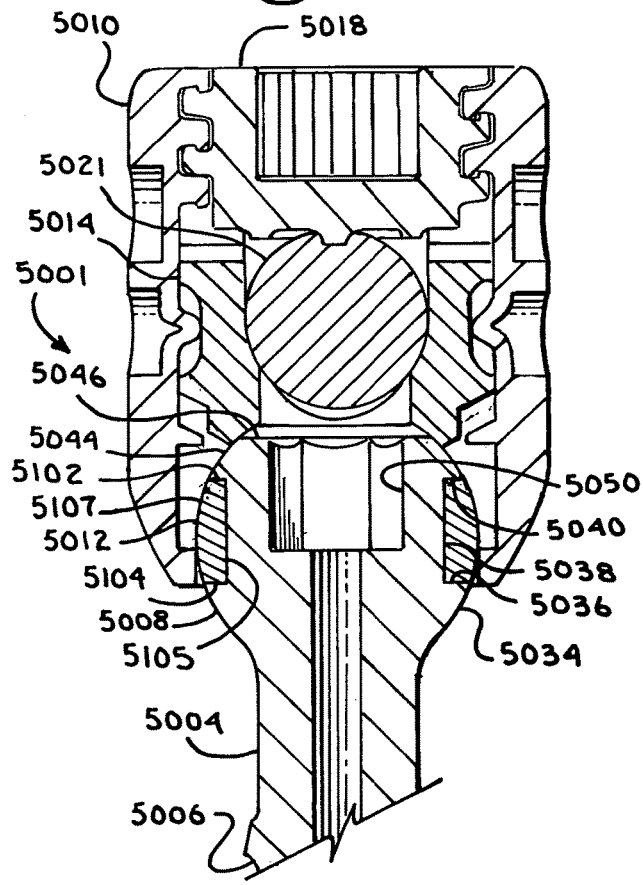

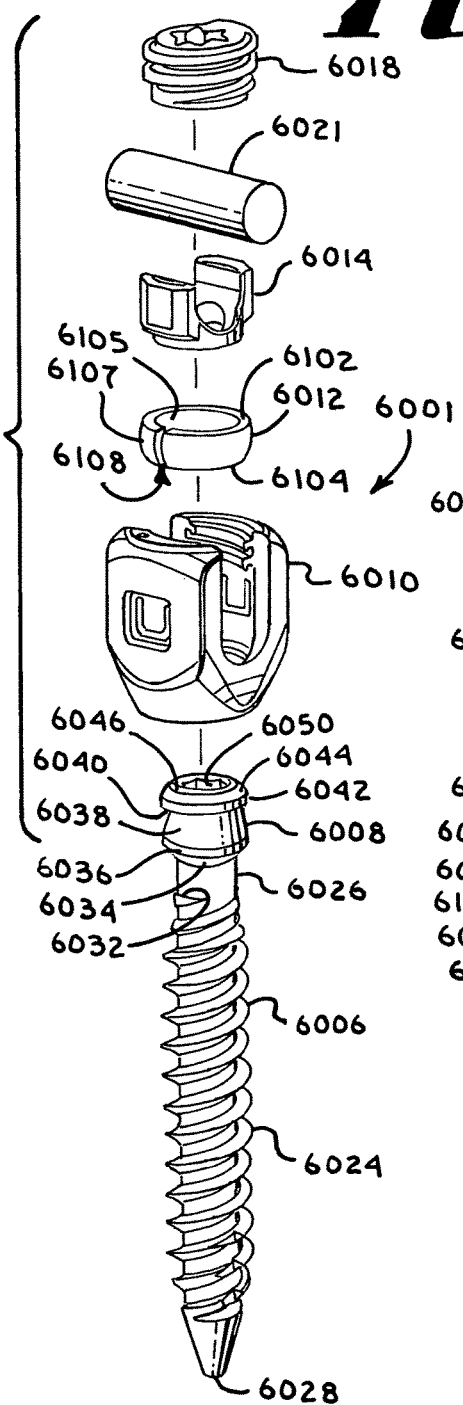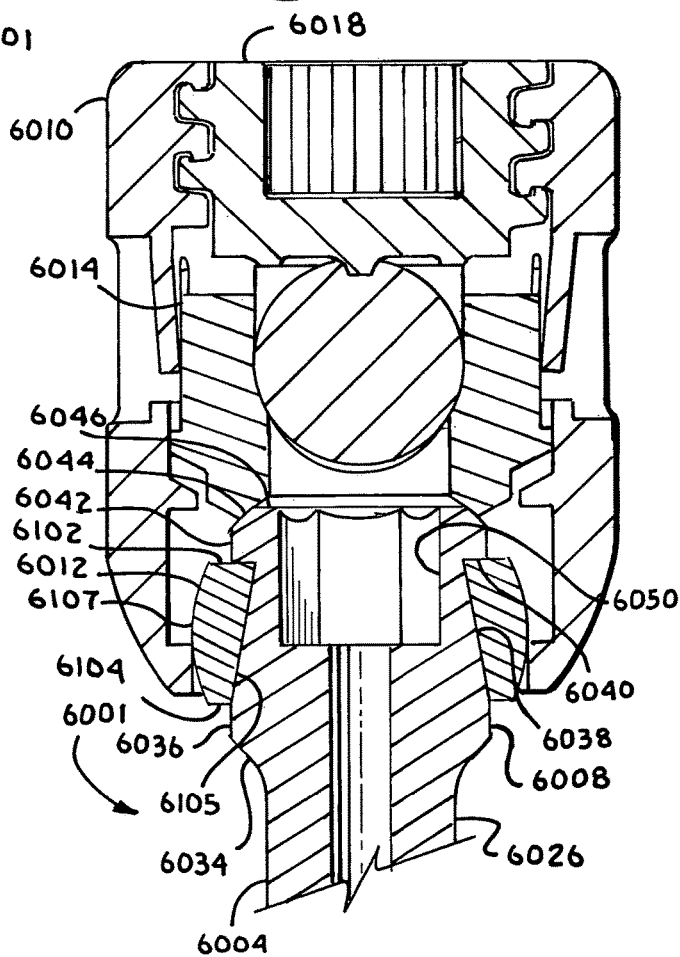
Fig. 69.
Fig. 70.

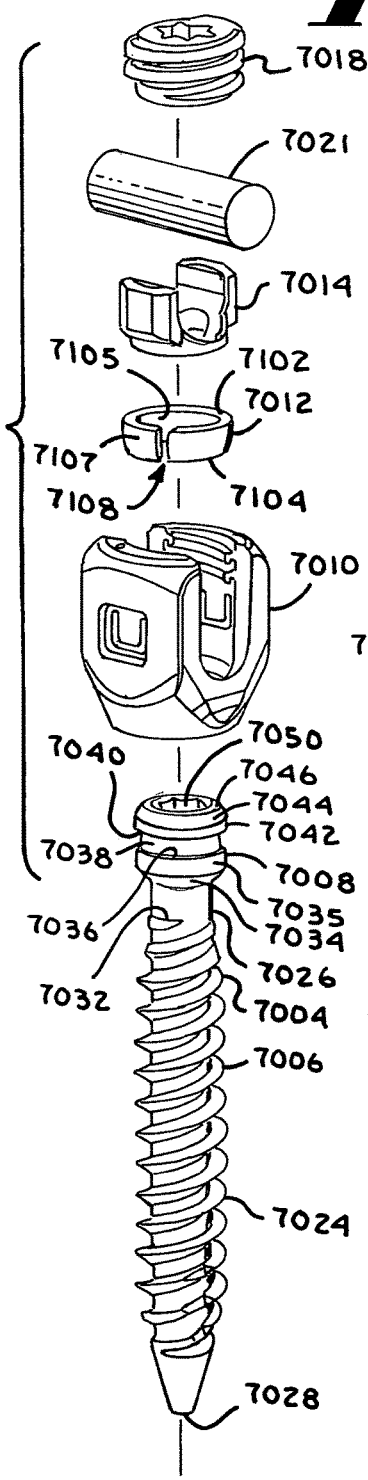
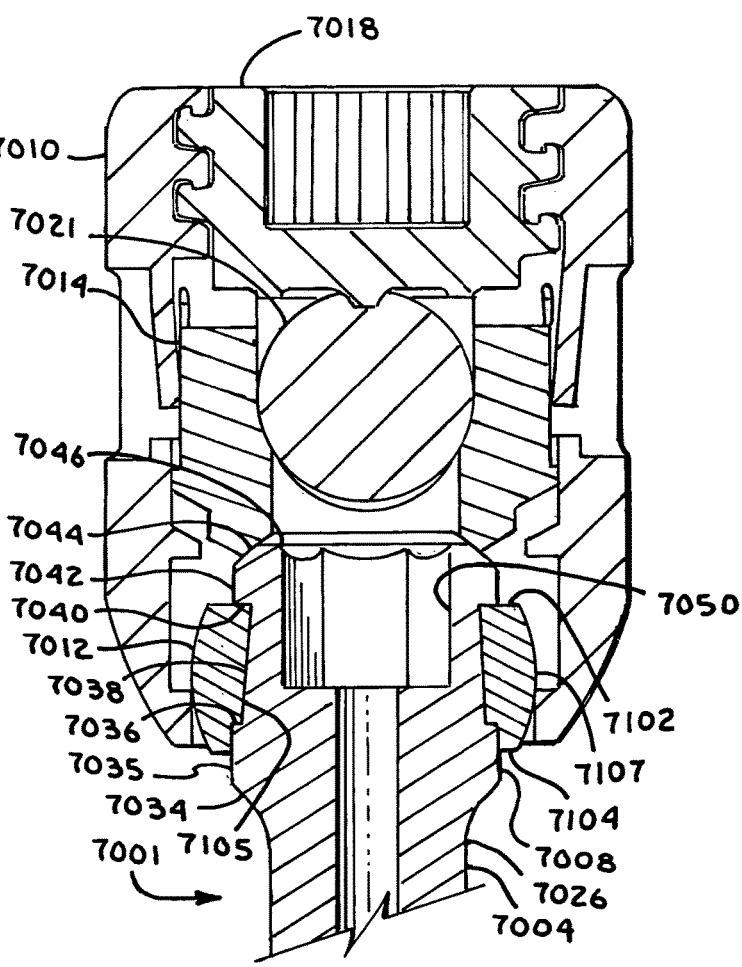
Fig. 71.
Fig. 72.

PIVOTAL BONE ANCHOR ASSEMBLIES WITH PRESSURE INSERTS AND SNAP ON ARTICULATING RETAINERS

CROSS-REFERENCE TO RELATED APPLICATIONS

This application claims the benefit of U.S. Provisional Application Ser. No. 61/456,163 filed Nov. 2, 2010 that is incorporated by reference herein.

BACKGROUND OF THE INVENTION

The present invention is directed to polyaxial bone screws for use in bone surgery, particularly spinal surgery and particularly to such screws with compression or pressure inserts.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod or other longitudinal connecting member can be inserted into the head or receiver and eventually the receiver is locked or fixed in a particular position relative to the shank. During the rod implantation process it is desirable to utilize bone screws or other bone anchors that have components that remain within the bone screw and further remain properly aligned during what is sometimes a very lengthy, difficult procedure.

SUMMARY OF THE INVENTION

A polyaxial bone screw assembly according to the invention includes a shank having an upper portion and a body for fixation to a bone; a receiver defining an upper open channel, a cavity and a lower opening; a compression insert; and an open ring-like resilient retainer for capturing the shank upper portion in the receiver along a cylindrical, frusto-conical, curvate or combination interface, the upper portion and attached retainer thereafter being pivotable with respect to the receiver prior to locking of the shank into a desired configuration. The compression insert operatively engages the shank upper portion and may be configured to be spaced from the retainer at all angular orientations of the shank with respect to the receiver. According to an aspect of the invention, an outer radius of the shank upper portion is different than an outer radius of the retainer. In some embodiments, the shank and retainer have the same outer radius. In various embodiments of the invention, the compression insert and retainer may or may not be down- or top-loaded through the upper open channel of the receiver while the shank upper portion is always bottom- or up-loadable into the receiver lower cavity at the lower opening. The resilient retainer is sized and shaped to expand about the shank upper portion and then "snap" or "pop" into place about the upper portion within the receiver cavity. Illustrated receivers typically include structure prohibiting the compression insert from moving upwardly out of the receiver channel and the compression insert prohibits movement of the retainer out of the receiver. Thus, after the compression insert and retainer are loaded into the receiver, both the compression insert and the retainer are captured within the receiver. A pre-assembled receiver, compression insert and retainer may be "popped on" or "snapped-on" to the shank upper portion prior to or after implantation of the shank into a vertebra. Such a "popping on" procedure includes the steps of uploading the shank upper portion into the receiver lower opening, the shank upper portion pressing against and expanding the resilient retainer followed by contraction of the retainer to an original or near original shape thereof about the shank upper portion along a cylindrical, curvate or frusto-conical surface thereof.

It is an object of the present invention to provide apparatus and methods directed to polyaxial bone screw assemblies with features that may be readily, securely fastened to each other and to bone. Furthermore, it is an object of the invention to provide apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention including a shank, a receiver, an open retainer and a compression insert and also shown with a closure top and a longitudinal connecting member in the form of a hard rod.

FIG. 2 is an enlarged top plan view of the shank of FIG. 1.

FIG. 3 is a cross-sectional view taken along the line 3-3 of FIG. 2.

FIG. 4 is an enlarged side elevational view of the receiver of FIG. 1 with portions broken away to show the detail thereof.

FIG. 5 is an enlarged side elevational view of the retainer of FIG. 1.

FIG. 6 is a top plan view of the retainer of FIG. 5.

FIG. 7 is a bottom plan view of the retainer of FIG. 5.

FIG. 16 is an enlarged and partial front elevational view, similar to FIG. 15, with portions broken away to show the detail thereof, showing the shank fully assembled with the retainer and showing the compression insert in a subsequent rod receiving position.

FIG. 17 is an enlarged and partially exploded side elevational view of the shank, retainer, receiver, compression insert, rod and closure of FIG. 1 with portions broken away to show the detail thereof, shown in a stage of assembly subsequent to that shown in FIG. 16 and with the shank disposed at an angle with respect to the receiver.

FIG. 18 is a reduced and partial perspective view of the assembly of FIG. 17, shown fully assembled.

FIG. 19 is an enlarged and partial front elevational view of the assembly of FIG. 17 shown with the shank shown axially aligned with the receiver.

FIG. 20 is an enlarged and partial cross-sectional view taken along the line 20-20 of FIG. 19.

FIG. 24 is a cross-sectional view of the receiver taken along the line 24-24 of FIG. 22, with the compression insert of FIG. 21 shown in side elevation in an early stage of assembly and further shown with the retainer of FIG. 21 with portions broken away to show the detail thereof.

FIG. 25 is an enlarged front elevational view of the receiver, retainer and compression insert of FIG. 24 with portions broken away to show the detail thereof, the insert shown in a further stage of assembly.

FIG. 26 is a partial front elevational view of the shank, receiver, retainer and compression insert of FIG. 25 with portions broken away to show the detail thereof and shown in a stage of assembly of the shank with the retainer.

FIG. 27 is a partial front elevational view with portions broken away, similar to FIG. 26, showing the shank, retainer and compression insert fully assembled within the receiver and positioned for receiving the rod of FIG. 21.

FIG. 30 is an exploded perspective view of a third, alternative embodiment of a polyaxial bone screw assembly according to the present invention including a shank, a receiver, a retainer, a compression insert and a closure top, and further shown with a longitudinal connecting member in the form of a deformable rod.

FIG. 31 is an enlarged perspective view of the receiver of FIG. 30.

FIG. 32 is an enlarged perspective view of the compression insert of FIG. 30.

FIG. 36 is an enlarged and partial front elevational view of the shank, receiver, retainer and compression insert of FIG. 30 with portions broken away to show the detail thereof and showing the shank in an initial stage of assembly with the retainer.

FIG. 37 is an enlarged and partial and partially exploded front elevational view of the shank, receiver, retainer, compression insert, rod and closure top of FIG. 30 with portions broken away to show the detail thereof.

FIG. 40 is an exploded perspective view of a fourth, alternative embodiment of a polyaxial bone screw assembly according to the present invention including a shank, a receiver, a retainer, a compression insert and a closure top, and further shown with a longitudinal connecting member in the form of a rod.

FIG. 41 is an enlarged top plan view of the shank of FIG. 40.

FIG. 42 is a cross-sectional view taken along the line 42-42 of FIG. 41.

FIG. 43 is an enlarged top plan view of the retainer of FIG. 40.

FIG. 44 is an enlarged and partial side elevational view of the assembly of FIG. 40 with portions broken away to show the detail thereof.

FIG. 45 is a reduced and partial cross-sectional view taken along the line 45-45 of FIG. 44.

FIG. 46 is a reduced side elevational view of the assembly of FIG. 40 shown with the shank disposed at an angle with respect to the receiver.

FIG. 47 is an enlarged and partial side elevational view, similar to FIG. 46, with portions broken away to show the detail thereof.

FIG. 48 is an exploded perspective view of a fifth, alternative embodiment of a polyaxial bone screw assembly according to the present invention including a shank, a receiver, a retainer, a compression insert and a closure top, and further shown with a longitudinal connecting member in the form of a rod.

FIG. 49 is an enlarged and partial front elevational view of the assembly of FIG. 48 with portions broken away to show the detail thereof.

FIG. 52 is an exploded perspective view of a sixth, alternative embodiment of a polyaxial bone screw assembly according to the present invention including a shank, a receiver, a retainer, a compression insert and a closure top, and further shown with a longitudinal connecting member in the form of a deformable rod.

FIG. 53 is an enlarged and partial front elevational view of the assembly of FIG. 52 with portions broken away to show the detail thereof.

FIG. 54 is an enlarged and partial cross-sectional view taken along the line 54-54 of FIG. 53.

FIG. 55 is a perspective view of an alternative retainer for use with polyaxial bone screw assembles according to the invention.

FIG. 56 is a bottom perspective view of the retainer of FIG. 55.

FIG. 57 is a top plan view of the retainer of FIG. 55.

FIG. 58 is a bottom plan view of the retainer of FIG. 55.

FIG. 59 is an exploded perspective view of a seventh alternative embodiment of a polyaxial bone screw assembly according to the present invention including a shank, a receiver, a retainer, a compression insert and a closure top, and further shown with a longitudinal connecting member in the form of a rod.

FIG. 60 is an enlarged and partial front elevational view of the assembly of FIG. 59 with portions broken away to show the detail thereof.

FIG. 61 is an exploded perspective view of a eighth alternative embodiment of a polyaxial bone screw assembly according to the present invention including a shank, a receiver, a retainer, a compression insert and a closure top, and further shown with a longitudinal connecting member in the form of a rod.

FIG. 62 is an enlarged and partial front elevational view of the assembly of FIG. 61 with portions broken away to show the detail thereof.

FIG. 63 is an exploded perspective view of a ninth alternative embodiment of a polyaxial bone screw assembly according to the present invention including a shank, a receiver, a retainer, a compression insert and a closure top, and further shown with a longitudinal connecting member in the form of a rod.

FIG. 64 is an enlarged and partial front elevational view of the assembly of FIG. 63 with portions broken away to show the detail thereof.

FIG. 65 is an exploded perspective view of a tenth alternative embodiment of a polyaxial bone screw assembly according to the present invention including a shank, a receiver, a retainer, a compression insert and a closure top, and further shown with a longitudinal connecting member in the form of a rod.

FIG. 66 is an enlarged and partial front elevational view of the assembly of FIG. 65 with portions broken away to show the detail thereof.

FIG. 67 is an exploded perspective view of a eleventh alternative embodiment of a polyaxial bone screw assembly according to the present invention including a shank, a receiver, a retainer, a compression insert and a closure top, and further shown with a longitudinal connecting member in the form of a rod.

FIG. 68 is an enlarged and partial front elevational view of the assembly of FIG. 67 with portions broken away to show the detail thereof.

FIG. 69 is an exploded perspective view of a twelfth alternative embodiment of a polyaxial bone screw assembly according to the present invention including a shank, a receiver, a retainer, a compression insert and a closure top, and further shown with a longitudinal connecting member in the form of a rod.

FIG. 70 is an enlarged and partial front elevational view of the assembly of FIG. 69 with portions broken away to show the detail thereof.

FIG. 71 is an exploded perspective view of a thirteenth alternative embodiment of a polyaxial bone screw assembly according to the present invention including a shank, a receiver, a retainer, a compression insert and a closure top, and further shown with a longitudinal connecting member in the form of a rod.

FIG. 72 is an enlarged and partial front elevational view of the assembly of FIG. 71 with portions broken away to show the detail thereof.

DETAILED DESCRIPTION OF THE INVENTION

Figure 8:
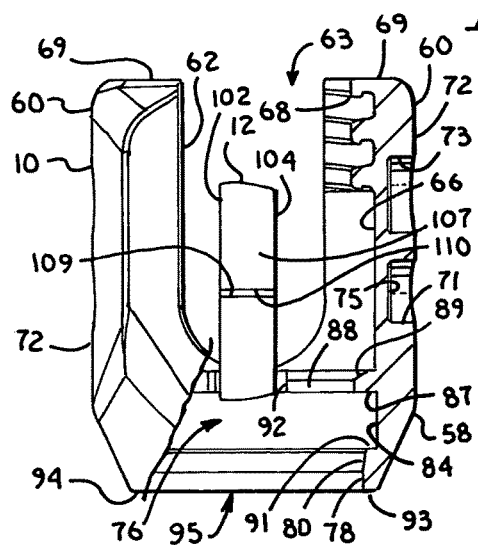
FIG. 8 is an enlarged front elevational view of the receiver of FIG. 1 with portions broken away to show the detail thereof and shown in an early stage of assembly with the retainer of FIG. 5.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-20 the reference number 1 generally represents a polyaxial bone screw apparatus or assembly according to the present invention. The assembly 1 includes a shank 4, that further includes a body 6 integral with an upwardly extending upper portion or capture structure 8; a receiver 10; a retaining structure or retainer 12 and a compression or pressure insert 14. The receiver 10, retainer 12 and compression insert 14 are initially assembled and may be further assembled with the shank 4 either prior or subsequent to implantation of the shank body 6 into a vertebra 13, as will be described in greater detail below. FIG. 1 further shows a closure structure 18 of the invention for capturing a longitudinal member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 13. The illustrated rod 21 is hard, stiff, non-elastic and cylindrical, having an outer cylindrical surface 22. It is foreseen (and also will be described with respect to other embodiments) that the rod 21 may be elastic, deformable and/or of a different cross-sectional geometry. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The shank 4, best illustrated in FIGS. 1-3, is elongate, with the shank body 6 having a helically wound bone implantable thread 24 (single or dual lead thread form) extending from near a neck 26 located adjacent to the upper portion or capture structure 8, to a tip 28 of the body 6 and extending radially outwardly therefrom. During use, the body 6 utilizing the thread 24 for gripping and advancement is implanted into the vertebra 13 leading with the tip 28 and driven down into the vertebra with an installation or driving tool (not shown), so as to be implanted in the vertebra to near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the upper end 32 and thus at a distance from the vertebra 13 when the body 6 is implanted in such vertebra.

The shank upper portion 8 is configured for a pivotable connection between the shank 4 (with attached retainer 12) and the receiver 10 prior to fixing of the shank 4 in a desired position with respect to the receiver 10. The shank upper portion 8 has an outer, convex and substantially spherical lower surface 34 that extends outwardly and upwardly from the neck 26 and terminates at a substantially planar ledge or shelf 36 that is annular and disposed perpendicular to the shank axis A. The spherical lower surface 34 has an outer radius that is the same or substantially similar to an outer radius of the retainer 12 as will be described in greater detail below, the surface 34 as well as the retainer 12 outer surface participating in the ball and socket joint formed by the shank 4 and attached retainer 12 within the partially spherical surface defining an inner cavity of the receiver 10. Extending upwardly from the ledge 36 is a cylindrical surface 38, the surface 38 having a radius that is smaller than the radius of the lower spherical surface 34. Extending outwardly from the cylindrical surface 38 is another annular surface or upper ledge 40 that faces toward the ledge 36 and is also substantially perpendicular to the axis A. As will be discussed in greater detail below, the lower ledge 36, cylindrical surface 38 and upper ledge 40 cooperate to capture and fix the resilient open retainer 12 to the shank upper portion 8, prohibiting movement of the retainer 12 along the axis A once the retainer 12 is located between the ledges 36 and 40. Extending upwardly from the upper ledge 40 is a cylindrical surface 42 having a radius smaller than the radius of the spherical surface 34 but larger than the radius of the cylindrical surface 38. Extending upwardly from the surface 42 is an upper partially spherical or domed surface 44. The spherical surface 44 has an outer radius configured for sliding cooperation and ultimate frictional mating with a substantially spherical concave surface of the compression insert 14 that has the same or substantially similar radius as the surface 44. The radius of the surface 44 is smaller than the radius of the lower spherical surface 34. Located near or adjacent to the surface 44 is an annular top surface 46. In the illustrated embodiment bevel 47 extends about the spherical surface 44 and is located between the spherical surface 44 and the annular planar top surface 46.

Figure 13:
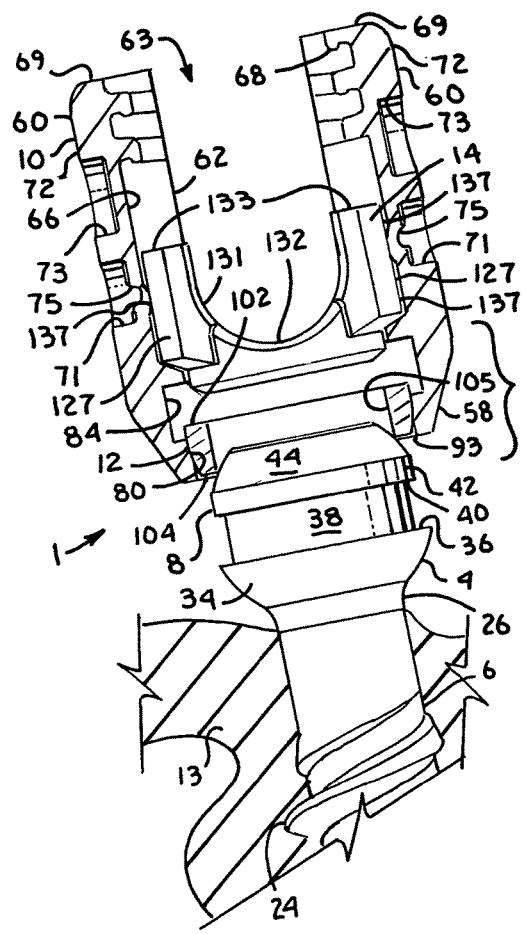
FIG. 13 is an enlarged and partial, partially exploded front elevational view of the shank of FIG. 1 and the receiver, retainer and compression insert as assembled as in FIG. 12, with portions broken away to show the detail thereof, the shank being shown implanted in a vertebra.

A counter sunk substantially planar base or seating surface 49 partially defines an internal drive feature or imprint 50. The illustrated internal drive feature 50 is an aperture formed in the top surface 46 and has a hex shape designed to receive a hex tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base 49 of the drive feature 50 is disposed perpendicular to the axis A with the drive feature 50 otherwise being coaxial with the axis A. In operation, a driving tool is received in the internal drive feature 50, being seated at the base 49 and engaging the six faces of the drive feature 50 for both driving and rotating the shank body 6 into the vertebra 13, either before the shank 4 is attached to the receiver 10 as shown in FIG. 13 or after the shank 4 is attached to the receiver 10, with the shank body 6 being driven into the vertebra 13 with the driving tool extending into the receiver 10.

The shank 4 shown in the drawings is cannulated, having a small central bore 51 extending an entire length of the shank 4 along the axis A. The bore 50 is defined by an inner cylindrical wall of the shank 4 and has a circular opening at the shank tip 28 and an upper opening communicating with the internal drive 50 at the surface 49. The bore 51 is coaxial with the threaded body 6 and the upper portion 8. The bore 51 provides a passage through the shank 4 interior for a length of wire (not shown) inserted into the vertebra 13 prior to the insertion of the shank body 6, the wire providing a guide for insertion of the shank body 6 into the vertebra 13.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_9)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1, 4 and 8-11, the receiver 10 has a generally U-shaped appearance with a partially discontinuous substantially cylindrical inner profile and a partially cylindrical and partially faceted outer profile.

The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 13, the axis B is typically disposed at an angle with respect to the axis A, as shown, for example, in FIGS. 17 and 18.

The receiver 10 includes a substantially cylindrical base 58 integral with a pair of opposed upstanding arms 60 forming a cradle and defining a U-shaped channel 62 between the arms 60 with an upper opening, generally 63, and a U-shaped lower seat 64, the channel 62 having a width for operably snugly receiving the rod 21 between the arms 60. Each of the arms 60 has an interior surface 66 that has a cylindrical profile and further includes a partial helically wound guide and advancement structure 68 extending radially inwardly from the surface 66 and located adjacent top surfaces 69 of each of the arms 60. In the illustrated embodiment, the guide and advancement structure 68 is a partial helically wound interlocking flangeform configured to mate under rotation with a similar structure on the closure structure 18, as described more fully below. However, it is foreseen that the guide and advancement structure 68 could alternatively be a square-shaped thread, a buttress thread, a reverse angle thread or other thread-like or non-thread-like helically wound discontinuous advancement structure for operably guiding under rotation and advancing the closure structure 18 downward between the arms 60, as well as eventual torquing when the closure structure 18 abuts against the rod 21.

An opposed pair of tool receiving and engaging apertures 71 are formed on outer surfaces 72 of the arms 60. Furthermore, two additional pair of tool receiving and engaging apertures 73 are formed on the arm surfaces 72 between each top surface 69 and the aperture 71. Some or all of the apertures 71 and 73 may be used for holding the receiver 10 during assembly with the shank 4 and the retainer 12, during the implantation of the shank body 6 into a vertebra when the shank is pre-assembled with the receiver 10, and during assembly of the bone anchor assembly 1 with the rod 21 and the closure structure 18. It is foreseen that tool receiving grooves or apertures may be configured in a variety of shapes and sizes and be disposed at other locations on the receiver arms 62. As illustrated, the apertures 71 do not extend completely through the arms 60. At each aperture 71, a thin wall 75 partially defines the aperture 71, the wall 75 being pushed or crimped inwardly toward and into a cooperating aperture of the pressure insert 14 during assembly therewith as will be described in greater detail below. Alternatively, and as will be described in greater detail below, the receiver or the pressure insert may be equipped with spring tabs that bias against a respective pressure insert or receiver to prohibit rotational movement of the insert about the receiver axis once the insert is loaded in the receiver and positioned with the rod-receiving channel of the insert in alignment with the U-shaped channel of the receiver.

Communicating with and located beneath the U-shaped channel 62 of the receiver 10 at the base portion 58 thereof is a chamber or cavity, generally 76, defined in part by a lower inner cylindrical surface 78, a substantially curved or spherical seating surface portion 80, a lower ledge 82, a central cylindrical portion 84, and an upper shelf, generally 86, further defined by a lower annular surface or stop 87, a cylindrical surface 88 and an upper frusto-conical surface 89. An annular surface 90 disposed perpendicular to the axis B spans between the surface 89 and the cylindrical surface 66 that substantially defines each of the receiver inner arms. In the illustrated embodiment, a frusto-conical or beveled surface 91 is located between the spherical seating surface 80 and the lower ledge 82. Opposed grooves 92 are formed in the shelf 86, the grooves 92 located near each U-shaped lower seat 64, the grooves 92 being sized and shaped for receiving the retainer 12 there through during assembly of the retainer 12 with the receiver 10 as will be described in greater detail below. The central cylindrical portion 84 is sized and shaped to allow for expansion of the retainer 12 about the surface 42 of the shank upper portion 8 during assembly while the upper shelf 86 acts as a stop, prohibiting upward movement of the retainer 12 out of the receiver cavity 76. The seating surface 80 is sized and shaped for slidably mating with the retainer 12 and also the surface 34 of the shank 4 and ultimately frictionally mating with the retainer 12 and or the surface 34 as will be described in greater detail below. The lower cylindrical surface 78 includes a bottom edge or neck 93 that forms a lower opening, generally 95, that communicates with both the cavity 76 and a receiver lower exterior or bottom 94 of the base 58. The neck 93 is substantially coaxially aligned with respect to the rotational axis B of the receiver 10. The lower neck 93 is also sized and shaped to be smaller than an outer radial dimension of the retainer 12 when the retainer 12 is fixed to the shank upper portion 8, so as to form a restriction to prevent the structure 12 and attached shank portion 8 from passing through the cavity 76 and out the lower exterior 94 of the receiver 10 during operation thereof.

With particular reference to FIGS. 1 and 5-10, the open retainer 12 that operates to capture the shank upper portion 8 within the receiver 10 has a central axis C that is operationally the same as the axis A associated with the shank 4 when the shank upper portion 8 and the retainer 12 are installed within the receiver 10. The retainer 12 is made from a resilient material, such as a stainless steel or titanium alloy, so that the retainer 12 may be expanded during assembly as will be described in greater detail below. However, because there is no need to compress the retainer 12 during assembly, the opening or slit that allows for expansion of the retainer 12 is designed to be very narrow, advantageously providing substantial or almost full surface contact between the retainer and the shank upper portion 8 and also between the retainer and the receiver seating surface 80. The retainer 12 has a central channel or hollow through bore, generally 101, that passes entirely through the structure 12 from a top surface 102 to a bottom surface 104 thereof. The bore 101 is primarily defined by a discontinuous inner cylindrical surface 105 that runs from the top surface 102 to the bottom surface 104. In some embodiments of the invention, as will be described in greater detail below, notches or grooves may be formed in the inner and/or bottom surfaces to more evenly distribute stress across the entire retainer during expansion thereof. The retainer 12 further includes an outer substantially spherical surface 107 running between the top surface 102 and the bottom surface 104, the surface 107 having the same or similar radius as the receiver seating surface 80 and the shank lower spherical surface 34. The resilient retainer 12 further includes first and second end surfaces, 109 and 110 disposed in spaced relation to one another when the retainer is in a neutral state. Both end surfaces 109 and 110 are disposed substantially perpendicular to the top surface 102 and the bottom surface 104. The embodiment shown in FIGS. 1-20 illustrates the surfaces 109 and 110 as substantially parallel, however, it is foreseen that it may be desirable to orient the surfaces obliquely or at a slight angle.

Figure 10:
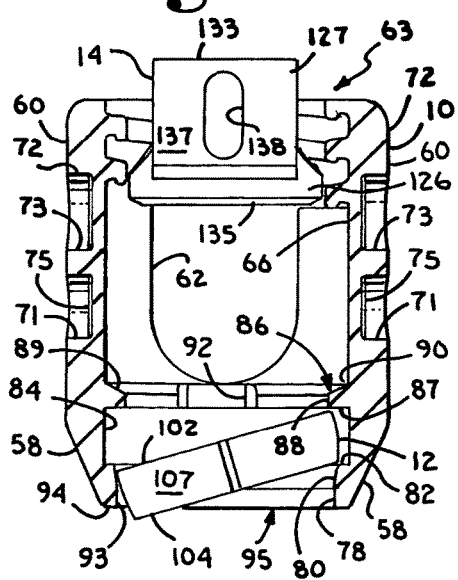
FIG. 10 is a front elevational view of the receiver, similar to FIG. 8, with portions broken away to show the detail thereof, further showing the retainer and also the compression insert of FIG. 1 in a later stage of assembly, the compression insert shown in side elevation.
Figure 11:
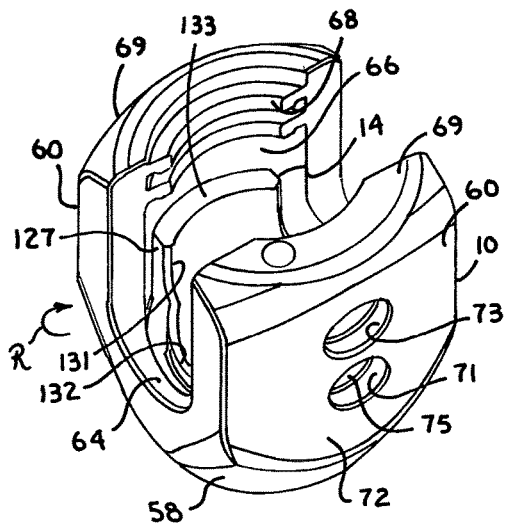
FIG. 11 is a perspective view, showing the receiver and compression insert of FIG. 10 in an assembled configuration.
Figure 12:
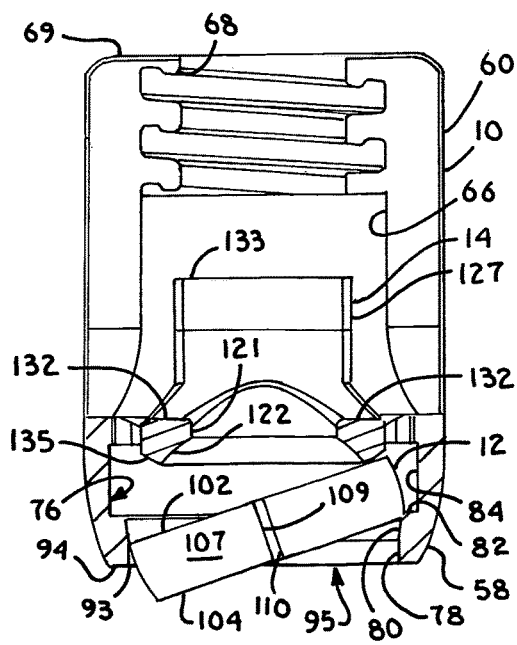
FIG. 12 is an enlarged side elevational view with portions broken away to show the detail thereof, showing the receiver, retainer and compression insert of FIG. 11.

With reference to FIGS. 1 and 10-16, the compression insert 14 is illustrated that is sized and shaped to be received by and down-loaded into the receiver 10 through the channel 64 and then rotated (see arrow R) as best illustrated in FIGS. 10 and 11. The compression insert 14 has an operational central axis that is the same as the central axis B of the receiver 10. With particular reference to FIG. 12, the compression insert 14 has a central channel or through bore substantially defined by an inner cylindrical surface 121 coaxial with an inner partially spherical surface 122. The compression insert 14 through bore is sized and shaped to receive a driving tool (not shown) therethrough that engages the shank drive feature 50 when the shank body 6 is driven into bone with the receiver 10 attached. The surface 122 is sized and shaped to slidingly receive and ultimately frictionally engage the substantially spherical or domed surface 44 of the shank upper portion 8 such that the surface 44 initially slidingly and pivotally mates with the spherical surface 122 to create a ball-and-socket type joint. The surfaces 44 and/or 122 may include a roughening or surface finish to aid in frictional contact between them once a desired angle of articulation of the shank 4 with respect to the receiver 10 is reached.

The compression insert 14 has a substantially cylindrical body 126 integral with a pair of upstanding arms 127. The bore defined by the inner surface 121 is disposed primarily within and through the body 126 and communicates with a generally U-shaped through channel 131 that is defined by the upstanding arms 127. The channel 131 has a lower seat 132 sized and shaped to closely, snugly engage the rod 21. It is foreseen that an alternative embodiment may be configured to include planar holding surfaces that closely hold a square or rectangular bar as well as hold a cylindrical rod-shaped, cord, or sleeved cord longitudinal connecting member. The arms 127 disposed on either side of the channel 131 extend upwardly from the body 126 to top surfaces 133. The arms 127 are sized and configured for ultimate placement below the receiver guide and advancement structure 68. It is foreseen that in some embodiments of the invention, the arms may be extended and the closure top configured such the arms ultimately directly engage the closure top 18 for locking of the polyaxial mechanism, for example, when the rod 21 is made from a deformable material. In such embodiments, the insert 14 would include a rotation blocking structure or feature that abuts against cooperating structure located on an inner wall of the receiver 10 (such as the insert shown with the assembly shown in FIGS. 30-39, for example), preventing rotation of the insert with respect to the receiver when the closure top is rotated into engagement with the insert. In the present embodiment, the top surfaces 133 of the arms 127 are ultimately positioned in spaced relation with the closure top 18, so that the closure top 18 frictionally engages the rod 21 only, pressing the rod 21 downwardly against the seating surface 132, the insert 14 in turn pressing against the shank 4 upper portion 8 that presses against the retainer 12 to lock the polyaxial mechanism of the bone screw assembly 1 at a desired angle.

The insert body 126 has a bottom surface 135 that is adjacent to the inner spherical surface 122. In the illustrated embodiment, the surface 134 is disposed at an angle with respect to the cylindrical surface of the body 126, providing improved clearance between components of the assembly 1 (as shown, for example, in FIG. 12). In other embodiments, the bottom surface may be substantially perpendicular to the cylindrical body 126 or have more than one curved, conical or annular surfaces.

The illustrated insert 14 further includes other features for manipulating and holding the insert 14 within the receiver 10. Each insert arm 127 includes an outer surface 137 having a substantially vertical groove 138 formed thereon, the grooves 138 cooperate with the receiver crimp wall 75 to aid in alignment of the insert channel 131 with the receiver channel 62.

The insert body 126 has an outer diameter slightly smaller than a diameter between crests of the guide and advancement structure 68 of the receiver 10, allowing for top loading of the compression insert 14 into the receiver opening 63, with the arms 127 of the insert 14 being located between the receiver arms 60 during insertion of the insert 14 into the receiver 10. Once the arms 127 of the insert 14 are generally located beneath the guide and advancement structure 68, the insert 14 is rotated into place about the receiver axis B (see FIG. 11 and the arrow R) until the insert top surfaces 133 are located directly below the guide and advancement structure 68 of each receiver arm 60 as will be described in greater detail below.

With reference to FIGS. 1 and 17-20, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A-rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 17-20, the closure structure or closure top 18 shown with the assembly 1 is rotatably received between the spaced arms 60 of the receiver 10. It is noted that the closure 18 top could be a twist-in or slide-in closure structure. The illustrated closure structure 18 is substantially cylindrical and includes an outer helically wound guide and advancement structure 182 in the form of a flange that operably joins with the guide and advancement structure 68 disposed on the arms 60 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 60 and having such a nature as to resist splaying of the arms 60 when the closure structure 18 is advanced into the channel 62, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 186 is used for both rotatable engagement and, if needed, disengagement of the closure 18 from the receiver arms 60. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a point 189 and a rim 190 for engagement and penetration into the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 60.

Preferably, the receiver 10, the retainer 12 and the compression insert 14 are assembled at a factory setting that includes tooling for holding, alignment and manipulation of the component pieces, as well as crimping a portion of the receiver 10 toward the insert 14. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point (see, e.g., FIG. 13). In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost.

Figure 9:
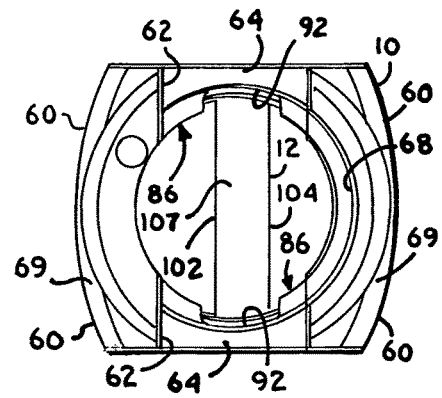
FIG. 9 is a top plan view of the receiver and retainer of FIG. 8.

Pre-assembly of the receiver 10, retainer 12 and compression insert 14 is shown in FIGS. 8-12. With particular reference to FIGS. 8 and 9, first the retainer 12 is inserted into the upper receiver opening 63, leading with the outer surface 107, the top surface 102 facing one arm 60 and the retainer bottom surface 104 facing the opposing arm 60. The retainer 12 is then lowered in such sideways manner into the channel 62 and partially into the receiver cavity through the opposed grooves 92, followed by tilting the retainer 12 such that the top surface 102 is moved into a position within the receiver under the annular surface or ledge 87 as best shown in FIG. 10. The retainer 12 is now at least partially seated on the receiver spherical surface 80.

Also with reference to FIG. 10 and with further reference to FIGS. 11 and 12, the compression insert 14 is then downloaded into the receiver 10 through the upper opening 63 with the bottom surface 135 facing the receiver arm top surfaces 69 and the insert arms 127 located between the opposed receiver arms 60. The insert 14 is then lowered toward the channel seat 64 until the insert 14 arm upper surfaces 133 are adjacent the receiver arm inner surfaces 66 located below the guide and advancement structure 68. Thereafter, the insert 14 is rotated in a clockwise or counterclockwise manner (see the arrow R) about the receiver axis B until the upper arm surfaces 133 are directly below the guide and advancement structure 68 of each arm as illustrated in FIGS. 11 and 12 with the U-shaped channel 131 of the insert 14 aligned with the U-shaped channel 62 of the receiver 10. In some embodiments, the insert arms 127 may need to be compressed slightly during rotation to clear inner surfaces of the receiver arms 60. As shown in FIGS. 12 and 13, the insert cylindrical base body 126 is received within the cylindrical surface 88 of the shelf 86 that defines an upper portion of the receiver base 58 with lower portions of the arms 127 in contact with the shelf surface 89. With reference to FIG. 13, the receiver thin walls 75 are then crimped inwardly toward the axis B by inserting a tool (not shown) through the receiver apertures 71, the tool pressing the walls 75 until the inner wall surfaces engage the insert 14 at the grooves 138 formed on the outer surface 137 of each of the insert arms 127 (see, e.g., FIG. 16). The crimping of the walls 75 into the grooves 138 keeps the insert 14 U-shaped channel 131 aligned with the receiver U-shaped channel 62. The crimping of the receiver walls 75 prohibits rotation of the insert 14 about the receiver axis B but allows for limited axial movement of the insert 14 with respect to the receiver 10 along the axis B when some force is exerted to slide the insert with respect to the receiver crimped walls up or down along the grooves 138. The insert 14 is fully captured within the receiver 10 by the guide and advancement structure 68 prohibiting movement of the insert 14 up and out through the receiver opening 63 as well as by retainer 12 located below the insert as shown in FIG. 12. Furthermore, as best shown in FIG. 12, during shipping and handling, the insert 14 prohibits the retainer 12 from escaping out of the receiver 10 through the opening 63 and also prohibits the retainer from moving out of alignment within the receiver chamber 76, and, in some embodiments from escaping out of the bottom opening 95. The receiver 10, retainer 12 and insert 14 combination is now pre-assembled and ready for assembly with the shank 4 either at the factory, by surgery staff prior to implantation, or directly upon an implanted shank 4 as will be described herein.

As illustrated in FIG. 13, the bone screw shank 4 or an entire assembly 1 made up of the assembled shank 4, receiver 10, retainer 12 and compression insert 14, is screwed into a bone, such as the vertebra 13, by rotation of the shank 4 using a suitable driving tool (not shown) that operably drives and rotates the shank body 6 by engagement thereof at the internal drive 50. Specifically, the vertebra 13 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 51 by first threading the wire into the opening at the bottom 28 and then out of the top opening at the drive feature 50. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. When the shank 4 is driven into the vertebra 13 without the remainder of the assembly 1, the shank 4 may either be driven to a desired final location or may be driven to a location slightly above or proud to provide for ease in assembly with the pre-assembled receiver, compression insert and retainer.

Figure 14:
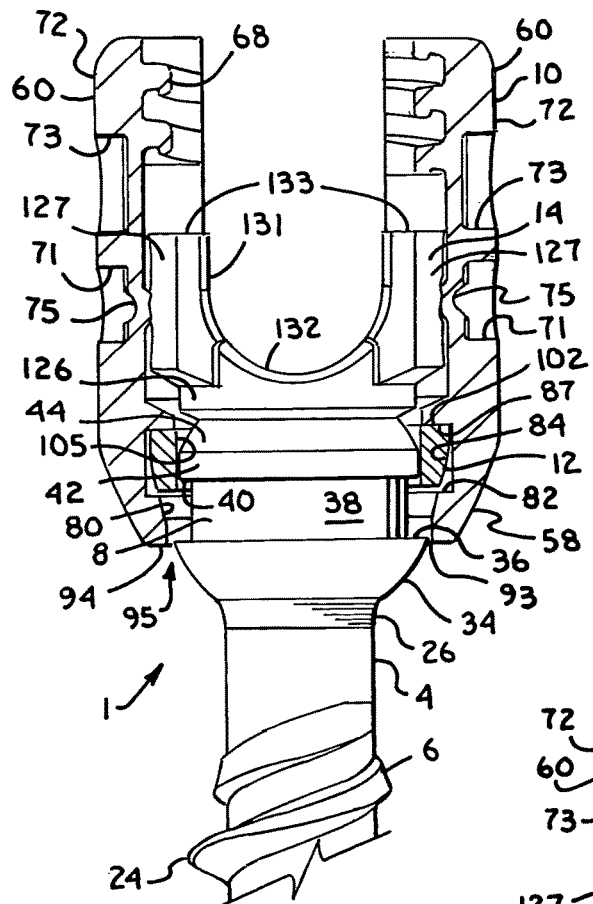
FIG. 14 is a partial front elevational view, similar to FIG. 13, with portions broken away to show the detail thereof and showing the shank in a stage of assembly with the retainer.
Figure 15:
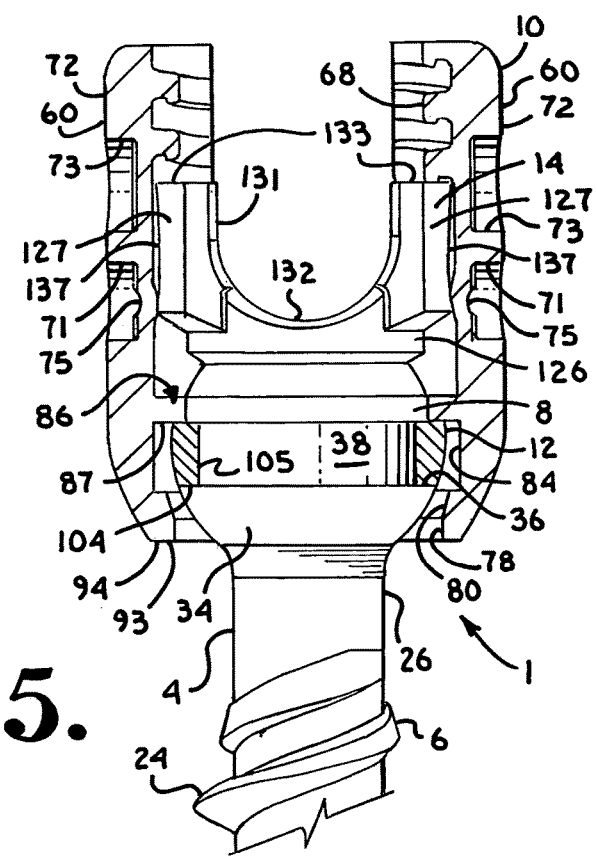
FIG. 15 is a partial front elevational view, similar to FIG. 14, with portions broken away to show the detail thereof and showing the shank in a subsequent stage of assembly with the retainer.

With further reference to FIG. 13, the pre-assembled receiver, insert and retainer are placed above the shank upper portion 8 until the shank upper portion is received within the opening 95. With particular reference to FIGS. 14 and 15, as the shank upper portion 8 is moved into the interior 76 of the receiver base, the shank upper portion 8 presses upwardly against the retainer 12 in the recess partially defined by the cylindrical surface 84. As the portion 8 continues to move upwardly toward the channel 62, the surface 44 forces outward movement of the retainer 12 towards the cylindrical surface 84 in the receiver expansion chamber or area as the shank 4 presses the retainer 12 against the receiver lower annular ledge surface 87. The retainer 12 initially expands about the shank upper spherical surface 44 and then slides along the cylindrical surface 42, snapping or popping into the recessed cylindrical surface 38, the surface 105 of the retainer 12 fully contacting and frictionally engaging the cylindrical surface 38 between the shank lower ledge 36 and the upper ledge 40. At this time, the retainer 12 is in a neutral or slightly expanded state, fully snapped onto the shank upper portion 8 with both the retainer 12 and shank upper portion 8 in pivotal relation with the receiver 10.

With reference to FIG. 16, the shank 4 and attached retainer 12 are then moved downwardly into a desired position with the retainer seated on the surface 80. The insert 14 may be pressed downwardly by a tool or by a rod and closure top as shown in FIG. 20. In some embodiments, the crimp walls 75 require that some force is used to press the inert 14 downwardly against the shank upper portion 8. In such embodiments, the insert 14 surface 122 is in frictional engagement with the shank upper portion surface 44 to an extent that the shank is pivotable with respect to the receiver, but in a non-floppy manner. In some embodiments, when the receiver 10 is pre-assembled with the shank 4, the entire assembly 1 may be implanted at this time by inserting the driving tool (not shown) into the receiver and the shank drive 50 and rotating and driving the shank 4 into a desired location of the vertebra 13.

The rod 21 is eventually positioned in an open or percutaneous manner in cooperation with the at least two bone screw assemblies 1. The closure structure 18 is then inserted into and advanced between the arms 60 of each of the receivers 10. The closure structure 18 is rotated, using a tool engaged with the inner drive 186 until a selected pressure is reached at which point the rod 21 engages the U-shaped seating surface 131 of the compression insert 14, further pressing the insert spherical surface 122 against the shank spherical surface 44, pressing the shank upper portion 8 and attached retainer 12 into locked frictional engagement with the receiver 10. With specific reference to FIGS. 19 and 20, as the closure structure 18 rotates and moves downwardly into the respective receiver 10, the point 189 and rim 190 engage and penetrate the rod surface 22, the closure structure 18 pressing downwardly against and biasing the rod 21 into compressive engagement with the insert 14 that urges the shank upper portion 8 and attached retainer 12 into locking engagement with the receiver, the retainer 12 spherical surface 107 frictionally abutting the spherical seating surface 80 of the receiver 10. For example, about 80 to about 120 inch pounds of torque on the closure top may be applied for fixing the bone screw shank 6 with respect to the receiver 10. Also, for example, with reference to FIGS. 17 and 18, when the shank 4 is disposed at an angle with respect to the receiver 10, the lower spherical surface 34 of the shank upper portion 8 may also be in frictional engagement with a portion of the receiver spherical seating surface 80. The retainer 12 may also expand slightly upon locking, providing a full and secure frictional locking engagement with the receiver at the surface 80.

If removal of the rod 21 from any of the bone screw assemblies 1 is necessary, or if it is desired to release the rod 21 at a particular location, disassembly is accomplished by using the driving tool (not shown) that mates with the internal drive 186 on the closure structure 18 to rotate and remove such closure structure from the cooperating receiver 10. Disassembly is then accomplished in reverse order to the procedure described previously herein for assembly.

Figure 21:
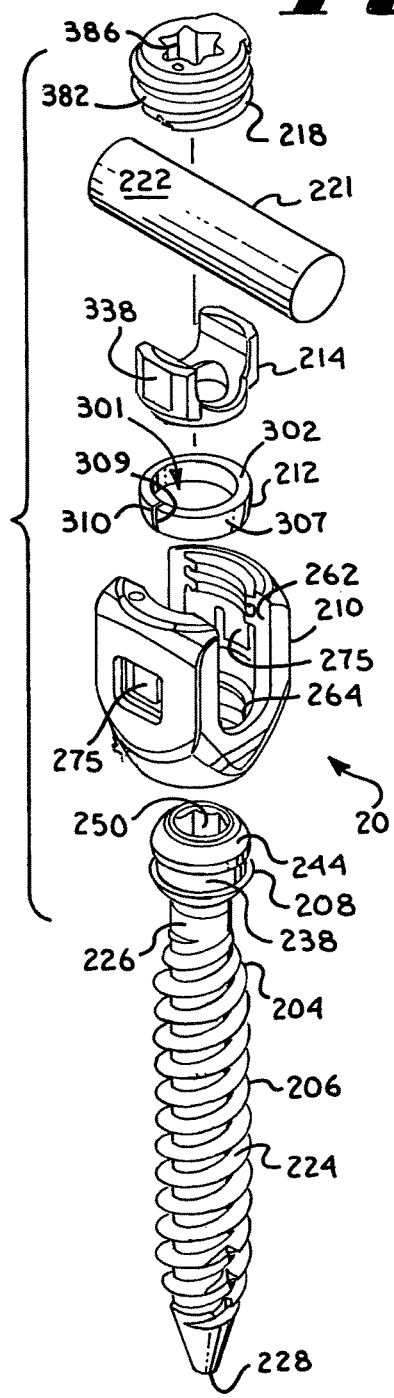
FIG. 21 is an exploded perspective view of a second, alternative embodiment of a polyaxial bone screw assembly according to the present invention including a shank, a receiver, a retainer, a compression insert and a closure top, and further shown with a longitudinal connecting member in the form of a rod.
Figure 22:
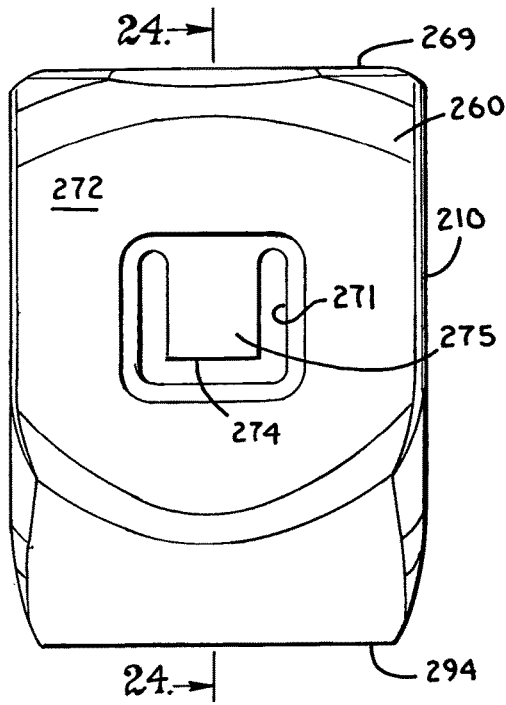
FIG. 22 is an enlarged side elevational view of the receiver of FIG. 21.
Figure 23:
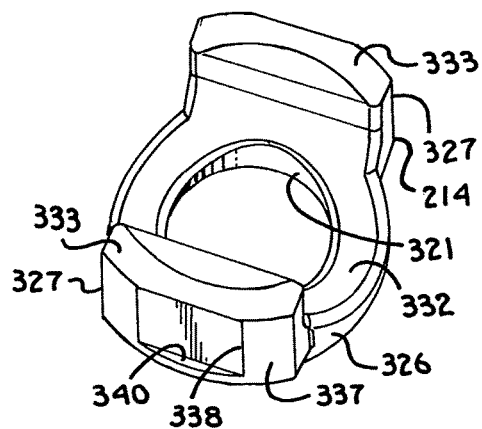
FIG. 23 is an enlarged perspective view of the compression insert of FIG. 21.
Figure 28:
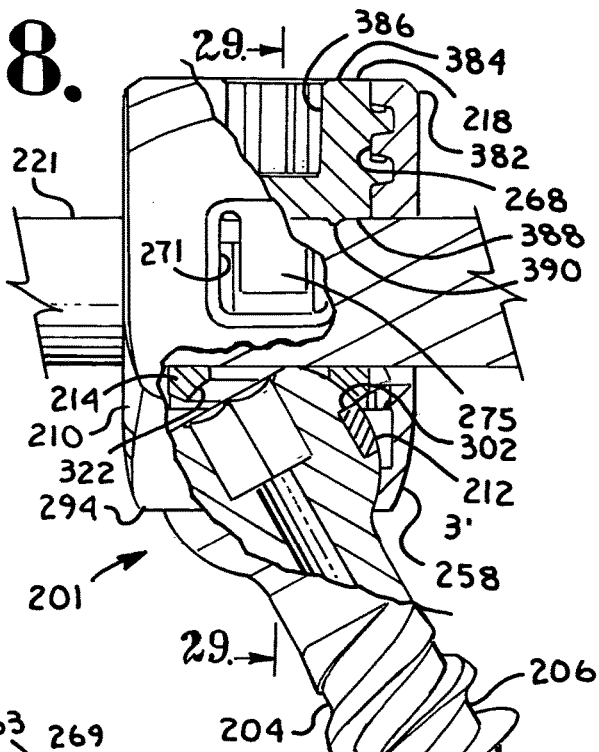
FIG. 28 is an enlarged and partial side elevational view of the shank, receiver, retainer, compression insert, rod and closure of FIG. 21 with portions broken away to show the detail thereof and shown fully assembled and with the shank disposed at an angle with respect to the receiver.
Figure 29:
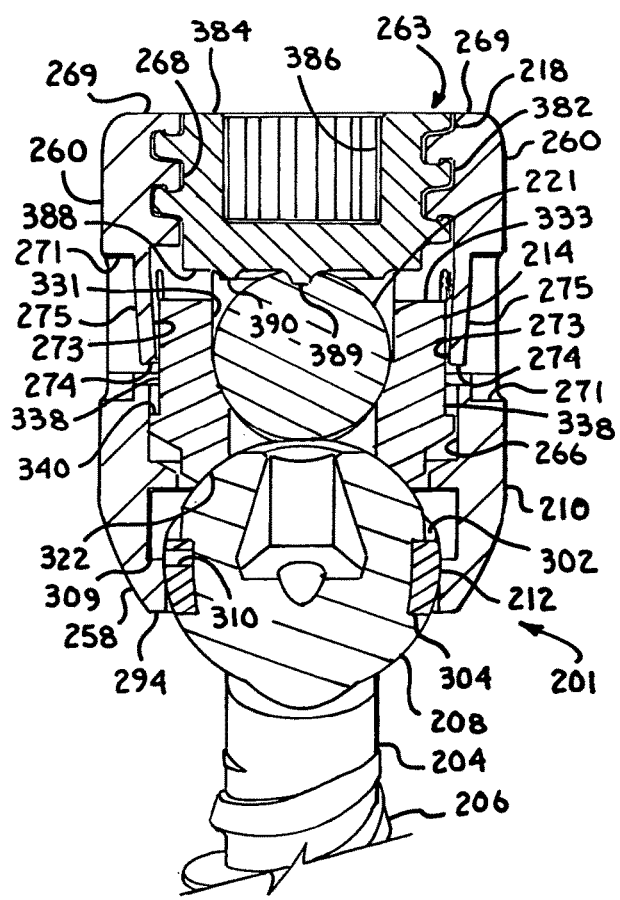
FIG. 29 is an enlarged and partial cross-sectional view taken along the line 29-29 of FIG. 28.
Figure 33:
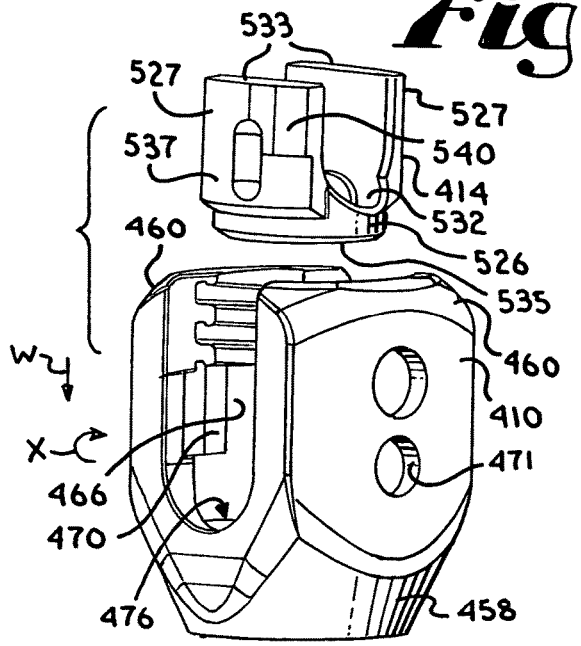
FIG. 33 is an enlarged exploded perspective view of the receiver and compression insert of FIG. 30 shown in a first stage of assembly.

With reference to FIGS. 21-29 the reference number 201 generally represents a polyaxial bone screw apparatus or assembly according to the present invention. The assembly 201 includes a shank 204, that further includes a body 206 integral with an upwardly extending upper portion or capture structure 208; a receiver 210; a retainer structure 212 and a compression or pressure insert 214. The receiver 210, retainer 212 and compression insert 214 are initially assembled and may be further assembled with the shank 204 either prior or subsequent to implantation of the shank body 206 into a vertebra (not shown), such as the vertebra 13 shown in FIG. 13 and described with respect to the assembly 1. FIGS. 21 and 28-29 further show a closure structure 218 of the invention for capturing a longitudinal connecting member, for example, a rod 221 which in turn engages the compression insert 214 that presses against the shank upper portion 208 and popped-on retainer 212, so as to capture, and fix the longitudinal connecting member 221 within the receiver 210 and thus fix the member 221 relative to the vertebra (not shown). The illustrated rod 221 is hard, stiff, non-elastic and cylindrical, having an outer cylindrical surface 222. It is foreseen that in other embodiments, the rod 221 may be elastic, deformable and/or of a different cross-sectional geometry as previously described herein with respect to the rod 21 of the assembly 1. The receiver 210 and the shank 204 cooperate in such a manner that the receiver 210 and the shank 204 can be secured at any of a plurality of angles, articulations or rotational alignments relative to one another and within a selected range of angles both from side to side and from front to rear, to enable flexible or articulated engagement of the receiver 210 with the shank 204 until both are locked or fixed relative to each other near the end of an implantation procedure.

The shank 204, best illustrated in FIGS. 21 and 26-29 is substantially similar to the shank 4 previously described herein with respect to the assembly 1. Thus, the shank 204 includes the shank body 206, upper portion or head 208, a shank thread 224, a neck 226, a tip 228, a top of thread 232, an upper portion lower spherical surface 234 a shelf or ledge 236, a cylindrical surface 238, and upper ledge 240 and upper spherical surface 244, a top surface 246, an internal drive 250 and a cannulation bore 251 the same or substantially similar to the respective body 6, upper portion or head 8, shank thread 24, neck 26, tip 28, top of thread 32, lower spherical surface 34, shelf 36, cylindrical surface 38, upper ledge 40, upper spherical surface 44, top surface 46, internal drive 50 and cannulation bore 51, as well as other features previously described herein with respect to the shank 4 of the assembly 1.

With particular reference to FIGS. 21, 22 and 24-29, the receiver 210 is substantially similar to the receiver 10 with the exception of opposed resilient spring tabs 275 that are provided in lieu of the thin walls 75 of the receiver 10. As shown in FIG. 25, for example, and discussed in greater detail below, the spring tabs 275 advantageously resiliently hold the insert 214 in an upper portion of the receiver until the insert 214 is pressed down by the user into a friction fit working position wherein the insert 214 is in frictional contact with the shank upper portion 208, the shank still movable with respect to the insert 214, but not in a loose or floppy manner.

The receiver 210 includes a base 258 with integral upstanding arms 260, a U-shaped channel 262 having an upper opening 263 and a lower seat 264, an arm interior substantially cylindrical surface 266, a guide and advancement structure 268, arm top surfaces 269, an inner base cavity or chamber generally 276, a lower cylindrical surface 278, a spherical seating surface 280, a lower ledge 282, a central cylindrical portion 284, an upper shelf, generally 286 further defined by a lower annular surface 287, a cylindrical surface 288, and an upper frusto-conical surface 289, a pair of opposed grooves 292, a neck 293, a bottom surface 294 and a lower opening, generally 295, the same or substantially similar to the respective base 58 with integral upstanding arms 60, U-shaped channel 62, channel upper opening 63 and lower seat 64, arm interior substantially cylindrical surface 66, guide and advancement structure 68, arm top surfaces 69, inner base cavity or chamber generally 76, lower cylindrical surface 78, spherical seating surface 80, lower ledge 82, central cylindrical portion 84, upper shelf, generally 86 further defined by the lower annular surface 87, the cylindrical surface 88, and the upper frusto-conical surface 89, opposed grooves 92, neck 93, bottom surface 94 and lower opening 95 of the receiver 10, and other features previously described herein with respect to the assembly 1.

Extending through each receiver arm 260 is an aperture 271 formed in an arm outer surface 272 and extending through each arm to the inner cylindrical surface 266. Each aperture 271 is in the form of a squared-off U-shape, thus forming each of the spring tabs 275 that are substantially rectangular in profile. Each tab 275 is integral with the respective receiver arm 260 at a location below and near the guide and advancement structure 268. Each tab 275 has an inner surface 273 that is an extension of the inner cylindrical surface 266 and is initially aligned with the surface 266 as shown, for example, in FIG. 24. A bottom surface 274 of each tab 275 is spaced from a remainder of the inner cylindrical surface 266 that extends downwardly to the shelf 286. As shown, for example, in FIG. 25, each spring tab 275 is bent inwardly toward a center axis of the receiver 210 either before or after the insert 214 is mounted within the receiver 210. In the illustrated embodiment, the tabs 275 are pressed inwardly toward grooves in the insert 214 after the insert 214 is located within the receiver as shown in FIG. 25 and as will be described in greater detail below.

With reference to FIGS. 21 and 24-29, the retainer 212 is the same or substantially similar in form and function to the retainer 12 previously described herein with respect to the assembly 1. Therefore, the retainer 212 includes a central through bore 301, a top surface 302, a bottom surface 304, an inner cylindrical surface 305, a spherical surface 307 and end surfaces 309 and 310 that are the same or similar to the respective central through bore 101, top surface 102, bottom surface 104, inner cylindrical surface 105, spherical surface 107 and end surfaces 109 and 110 previously described herein with respect to the retainer 12.

With reference to FIGS. 21 and 23-29, the compression insert 214 is substantially similar in form and function to the insert 14 previously described herein with respect to the assembly 1. The insert 214 differs from the insert 14 only in a groove or flat 338 that has a different geometry than the groove 138 of the insert 14. Therefore, the insert 214 includes an inner cylindrical surface 321, an inner spherical surface 322, a cylindrical body 326, a pair of upstanding arms 327, a U-shaped channel 331 having a lower seat 332, arm top surfaces 333, a bottom surface 335 and arm outer surfaces 337 that are the same or substantially similar to the respective inner cylindrical surface 121, inner spherical surface 122, cylindrical body 126, upstanding arms 127, U-shaped channel 131 with lower seat 132, arm top surfaces 133, the bottom surface 135 and arm outer surfaces 137 of the insert 14 previously described herein.

The flat 338 formed in each arm outer surface 337 runs from the top surface 333 to a lower ledge 340. As shown, for example, in FIG. 26, the flat 338 and the flat lower ledge 340 are sized and shaped to allow the insert 214 to be moved upwardly adjacent to the guide and advancement structure 268 during the "popping-on" of the shank 204 into the retainer 212 located within the receiver expansion chamber formed within the inner cylindrical surface 284. The receiver spring tabs 275 are in sliding frictional engagement with the flats 338 during all of the assembly steps with the shank 204 as well as when the shank 204 is manipulated with respect to the receiver 210, the insert surface 322 in frictional but movable engagement with the shank surface 244, providing non-floppy pivoting of the shank 204 with respect to the receiver 210 until the shank and receiver are locked together by action of the closure top 218 pressing against the rod 221 that in turn presses against the insert 214.

With reference to FIGS. 21 and 28-29, the closure top 218 is identical or substantially similar to the closure top 18 previously described herein with respect to the assembly 1, having a flange form guide and advancement structure 382, a top surface 384, an internal drive 386, a base or bottom surface 388, a point 389 and a rim 390 the same or substantially similar to the respective guide and advancement structure 182, top surface 184, internal drive 186, base or bottom surface 188, point 189 and rim 190 of the closure top 18.

Preferably, the receiver 210, the retainer 212 and the compression insert 214 are assembled at a factory setting that includes tooling for holding, alignment and manipulation of the component pieces, as well as pressing the receiver 210 spring tabs 275 toward the insert 214. In some circumstances, the shank 204 is also assembled with the receiver 210, the retainer 212 and the compression insert 214 at the factory. In other instances, it is desirable to first implant the shank 204, followed by addition of the pre-assembled receiver, retainer and compression insert at the insertion point, similar to what is shown with respect to assembly 1 at FIG. 13. In this way, the surgeon may advantageously and more easily implant and manipulate the shanks 204, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 208 and/or hydroxyapatite on the shank 206), with the receiver, retainer and compression insert. Allowing the surgeon to choose the appropriately sized or treated shank 204 advantageously reduces inventory requirements, thus reducing overall cost.

Pre-assembly of the compression insert 214 with the receiver 210 and retainer 212 is shown FIGS. 24-25. First, however, the retainer 212 is inserted into the upper receiver opening 263, leading with the outer surface 307, the top surface 302 facing one arm 260 and the retainer bottom surface 304 facing the opposing arm 260. The retainer 212 is then lowered in such sideways manner into the channel 262 and partially into the receiver cavity through the opposed grooves 292, followed by tilting the retainer 212 such that the top surface 302 is moved into a position within the receiver under the annular surface or ledge 287 and the retainer is at least partially seated on the receiver spherical surface 280. Reference is made herein to FIGS. 8-10 showing the insertion of the retainer 12 into the receiver 10 which is accomplished in an identical manner to the insertion of the retainer 212 into the receiver 210.

With reference to FIGS. 24 and 25, the compression insert 214 is then downloaded into the receiver 210 through the upper opening 263 with the bottom surface 335 facing the receiver arm top surfaces 269 and the insert arms 327 located between the opposed receiver arms 260. The insert 214 is then lowered toward the channel seat 264 until the insert 214 arm upper surfaces 333 are adjacent the receiver arm inner surfaces 266 located below the guide and advancement structure 268. Thereafter, the insert 214 is rotated in a clockwise or counter-clockwise manner about the receiver axis until the upper arm surfaces 333 are directly below the guide and advancement structure 268 of each arm as illustrated in FIG. 25 with the U-shaped channel 331 of the insert 214 aligned with the U-shaped channel 262 of the receiver 210. At this time, the receiver spring tabs 275 are pressed and bent inwardly until the spring tab surfaces 273 frictionally engage the insert flat surfaces 338. At this time, in some embodiments of the invention, frictional engagement between the tabs 275 and the insert surfaces 338 may be used to hold the insert 214 in an upper portion of the receiver 210, for example as shown in FIG. 26. In other embodiments, the spring tabs 275 function only to hold the insert 214 U-shaped channel 331 in alignment with the receiver U-shaped channel 262. Also, in other embodiments, the spring tabs 275 are bent inwardly before the insert 214 is loaded into the receiver, the tabs 275 being resilient enough to be pushed outwardly during rotation of the insert 214 and then snapping onto the flat surfaces 338 once the insert 214 is rotated into a desired aligned position. In other embodiments of the invention, the spring tabs 275 may be originally formed or machined to be directed inwardly and then are sprung outwardly during rotation of the insert 214, springing back to a neutral inwardly directed position once the flats 338 engage the inner surfaces 273 of the spring tabs 275. As shown in FIG. 24-27, the receiver spring tabs 275 prohibit rotation of the insert 214 about the receiver central axis but allow for limited up and down movement of the insert 214 with respect to the receiver 210 along the central axis thereof when some force is exerted to slide the insert with respect to the receiver spring tab surfaces 273 up or down along the flats 338. The insert 214 is fully captured within the receiver 210 by the guide and advancement structure 268 prohibiting movement of the insert 214 up and out through the receiver opening 263 as well as by the spring tabs 275 abutting against the ledge 340 of the flats 338. Furthermore, similar to what is shown with respect to the assembly 1 in FIG. 12, during shipping and handling, the insert 214 prohibits the retainer 212 from escaping out of the receiver 210 through the opening 263 and also prohibits the retainer from moving out of alignment within the receiver chamber 276, and, in some embodiments from escaping out of the bottom opening 295. The receiver 210, retainer 212 and insert 214 combination is now pre-assembled and ready for assembly with the shank 204 either at the factory, by surgery staff prior to implantation, or directly upon an implanted shank 204 as will be described herein.

Similar to the description herein with respect to the assembly 1, the bone screw shank 204 or an entire assembly 201 made up of the assembled shank 204, receiver 210, retainer 212 and compression insert 214, is screwed into a bone, such as the vertebra 13, by rotation of the shank 204 using a suitable driving tool (not shown) that operably drives and rotates the shank body 206 by engagement thereof at the internal drive 250 and in a percutaneous or minimally invasive surgical manner. When the shank 204 is driven into the vertebra without the remainder of the assembly 201, the shank 204 may either be driven to a desired final location or may be driven to a location slightly above or proud to provide for ease in assembly with the pre-assembled receiver, compression insert and retainer.

With reference to FIGS. 13-15 (directed to identical or substantially similar assembly steps for the assembly 1) and with reference to FIG. 26, the pre-assembled receiver, insert and retainer are placed above the shank upper portion 208 until the shank upper portion is received within the opening 295. As the shank upper portion 208 is moved into the interior 276 of the receiver base, the shank upper portion 208 presses upwardly against the retainer 212 in the recess partially defined by the cylindrical surface 284. As the portion 208 continues to move upwardly toward the channel 262, the surface 244 forces outward movement of the retainer 212 towards the cylindrical surface 284 in the receiver expansion chamber or area as the shank 204 presses the retainer 212 against the receiver lower annular ledge surface 287. The retainer 212 initially expands about the shank upper spherical surface 244 and then slides along the cylindrical surface 242, snapping or popping into the recessed cylindrical surface 238, the surface 305 of the retainer 212 fully contacting and frictionally engaging the cylindrical surface 238 between the shank lower ledge 236 and the upper ledge 240. At this time, the retainer 212 is in a neutral or slightly expanded state, fully snapped onto the shank upper portion 208 with both the retainer 212 and shank upper portion 208 in pivotal relation with the receiver 210.

With reference to FIG. 27, the shank 204 and attached retainer 212 are then moved downwardly into a desired position with the retainer seated on the surface 280. The insert 214 may slide downwardly with the retainer 212, or in some embodiments, remain in an upper part of the receiver 210 retained by the spring tabs 275 until the insert 214 is pressed downwardly by a tool or by a rod and closure top as shown in FIG. 29. In such embodiments, the insert 214 surface 322 is in frictional engagement with the shank upper portion surface 244 to an extent that the shank is pivotable with respect to the receiver, but in a non-floppy manner. In some embodiments, when the receiver 210 is pre-assembled with the shank 204, the entire assembly 201 may be implanted at this time by inserting the driving tool (not shown) into the receiver and the shank drive 250 and rotating and driving the shank 204 into a desired location of the vertebra, such as the previously illustrated vertebra 13.

The rod 221 is eventually positioned in an open or percutaneous manner in cooperation with the at least two bone screw assemblies 201. The closure structure 218 is then inserted into and advanced between the arms 260 of each of the receivers 210. The closure structure 218 is rotated, using a tool engaged with the inner drive 386 until a selected pressure is reached at which point the rod 221 engages the U-shaped seating surface 331 of the compression insert 214, further pressing the insert spherical surface 322 against the shank spherical surface 244, pressing the retainer 212 that is attached to the shank upper portion 208 into locked frictional engagement with the receiver 210. As the closure structure 218 rotates and moves downwardly into the respective receiver 210, the point 389 and rim 390 engage and penetrate the rod surface 222, the closure structure 218 pressing downwardly against and biasing the rod 221 into compressive engagement with the insert 214 that urges the shank upper portion 208 and attached retainer 212 into locking engagement with the receiver, the retainer 212 spherical surface 307 frictionally abutting the spherical seating surface 280 of the receiver 210. For example, about 80 to about 120 inch pounds of torque on the closure top may be applied for fixing the bone screw shank 206 with respect to the receiver 210. Also, for example, with reference to FIGS. 28 and 29, when the shank 204 is disposed at an angle with respect to the receiver 210, the lower spherical surface 234 of the shank upper portion 208 may also be in frictional engagement with a portion of the receiver spherical seating surface 280. The retainer 212 may also expand slightly upon locking, providing a full and secure frictional locking engagement with the receiver at the surface 280.

If removal of the rod 221 from any of the bone screw assemblies 201 is necessary, or if it is desired to release the rod 221 at a particular location, disassembly is accomplished by using the driving tool (not shown) that mates with the internal drive 386 on the closure structure 218 to rotate and remove such closure structure from the cooperating receiver 210. Disassembly is then accomplished in reverse order to the procedure described previously herein for assembly.

Figure 38:
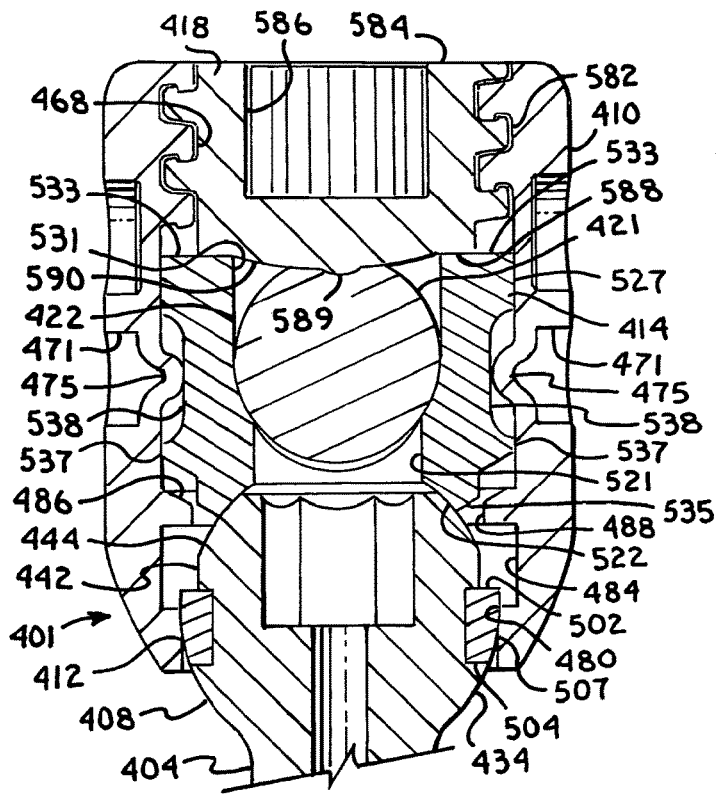
FIG. 38 is a partial front elevational view with portions broken away, similar to FIG. 37, showing all the components of FIG. 30 fully assembled.
Figure 39:
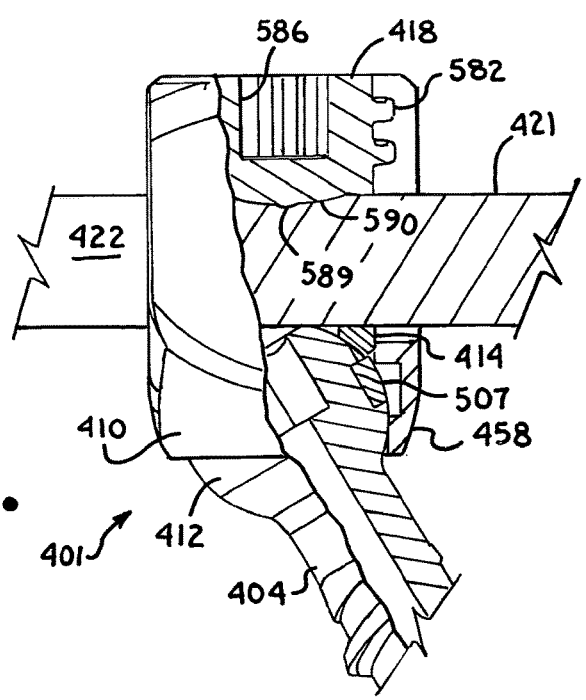
FIG. 39 is an enlarged and partial side elevational view of the assembly shown in FIG. 30 with portions broken away to show the detail thereof and shown fully assembled as in FIG. 38 but with the shank disposed at an angle with respect to the receiver.
Figure 50:
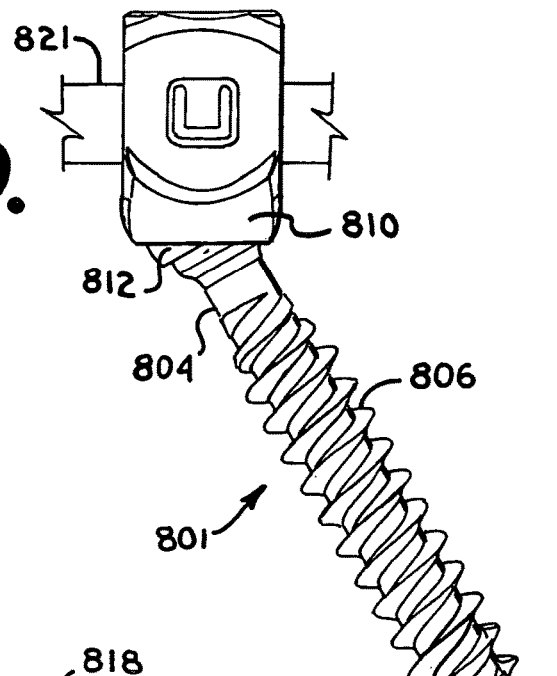
FIG. 50 is a side elevational view of the assembly of FIG. 48 shown with the shank disposed at an angle with respect to the receiver.

With reference to FIGS. 30-39 the reference number 401 generally represents a polyaxial bone screw apparatus or assembly according to the present invention. The assembly 401 includes a shank 404, that further includes a body 406 integral with an upwardly extending upper portion or capture structure 408; a receiver 410; an open retainer structure 412 and a compression or pressure insert 414. FIGS. 30 and 37-39 further show a closure structure 418 of the invention for capturing a longitudinal connecting member, for example, a deformable rod 421 within the receiver 410. The rod 421 may be elastic or inelastic, and is illustrated as a deformable PEEK rod. The assembly 401 is substantially identical to the assembly 1 with a few exceptions. The exceptions are a stop block or blocks 540 located on the insert 414, each cooperating with a receiver recess having a curved or planar stop wall 470 that prohibits rotation of the insert 414 with respect to the receiver 410 in a clock-wise manner, providing for secure and sturdy alignment between the insert 414 and the receiver 410 when the closure top 418 is rotated in a clock-wise manner to press down, not only upon the deformable rod 421, but also on the insert 414 as shown in FIG. 38, for example. Thus, even if the PEEK or other deformable rod 421 shifts or deforms with respect to the closure top 418, the polyaxial mechanism of the assembly 401 will remain locked in place because of the locking force of the closure top 418 on the insert 414 that in turns presses directly against the shank as will be described in greater detail below.

With particular reference to FIGS. 30 and 36-39, the shank 404 is substantially similar in form and function to the shank 4 previously described herein with respect to the assembly 1. Thus, the shank 404 includes the shank body 406, upper portion or head 408, a lower spherical surface 434, a cylindrical surface 438, an upper cylindrical surface 442, an upper spherical surface 444 and an internal drive 250 that are the same or substantially similar in form and function to the respective body 6, upper portion or head 8, lower spherical surface 34, cylindrical surface 38, upper cylindrical surface 42, upper spherical surface 44, internal drive 50, and all the other features previously described herein with respect to the shank 4 of the assembly 1.

With particular reference to FIGS. 30, 31 and 33-39, the receiver 410 is substantially similar to the receiver 10 previously described herein with the exception of the addition of the recessed stop wall 470 mentioned above. Thus, the receiver 410 includes a base 458 with integral upstanding arms 460, a U-shaped channel 462, arm interior substantially cylindrical surfaces 466, a guide and advancement structure 468, a pair of opposed tool apertures 471 each partially defined by a thin crimp wall 475, an inner base cavity or chamber generally 476, a lower cylindrical surface 478, a spherical seating surface 480, a central cylindrical expansion portion 484 and an upper shelf, generally 486, the same or substantially similar in form and function to the respective base 58 with integral upstanding arms 60, U-shaped channel 62, arm interior substantially cylindrical surfaces 66, guide and advancement structure 68, tool apertures 71, crimp walls 75, inner base cavity or chamber generally 76, lower cylindrical surface 78, spherical seating surface 80, central cylindrical expansion portion 84 and upper shelf, generally 86, and other features previously described herein with respect to the receiver 10 of the assembly 1.

With particular reference to FIG. 31, the recess in the receiver that is partially defined by the blocking wall 470 is formed in each cylindrical inner surface 466 located below the guide and advancement structure 468. The recesses with blocking walls 470 are located opposite one another such that the insert 414 may only be rotated into place in a clock-wise manner as will be described in more detail below.

With reference to FIGS. 30 and 36-39, the open, expandable retainer 412 is the same or substantially similar in form and function to the retainer 12 previously described herein with respect to the assembly 1. Therefore, the retainer 212 includes a top surface 502, a bottom surface 504, an inner cylindrical surface 505, an outer spherical surface 507 and a through slit 508 that are the same or similar in form and function to the respective top surface 102, bottom surface 104, inner cylindrical surface 105, outer spherical surface 107 and slit formed by end surfaces 109 and 110 previously described herein with respect to the retainer 12.

With reference to FIGS. 30 and 32-39, the compression insert 414 is substantially similar in form and function to the insert 14 previously described herein with respect to the assembly 1 with the exception of the addition of the block or stop 540. Therefore, the insert 414 includes an inner cylindrical surface 521, an inner spherical surface 522, a cylindrical body 526, a pair of upstanding arms 527, a U-shaped channel 531 having a lower seat 532, arm top surfaces 533, a bottom surface 535 and arm outer surfaces 537, each with a groove 538 formed therein that are the same or substantially similar in form and function to the respective inner cylindrical surface 121, inner spherical surface 122, cylindrical body 126, upstanding arms 127, U-shaped channel 131 with lower seat 132, arm top surfaces 133, the bottom surface 135 and arm outer surfaces 137 with grooves 138 of the insert 14 previously described herein. The illustrated embodiment includes two stop blocks 540, each formed on the outside surface 537 of each arm 527 and located near the arm top surface 533.

With reference to FIGS. 30 and 37-39, the closure top 418 is substantially similar to the closure top 18 previously described herein with respect to the assembly 1 with the exception of the lower rod contacting surfaces thereof. The closure top 418 has a flange form guide and advancement structure 582, a top surface 584 and an internal drive 586 that is the same of substantially similar in form and function to the respective guide and advancement structure 182, top surface 184 and internal drive 186 of the closure top 18 previously described herein. The closure top 418 further includes an annular outer base rim 588 and a central point or nub 589. The nub 589 is located centrally on a domed or spherical surface 590 that is surrounded by and extends from the base rim 588 downwardly away from the closure 418.

The receiver 410 and the retainer 412 are assembled in a manner identical to what has been described herein with respect to the assembly of the receiver 10 and the retainer 12. As with the assembly 1, preferably, the receiver 410, the retainer 412 and the compression insert 414 are assembled at a factory setting that includes tooling for holding, alignment and manipulation of the component pieces, as well as crimping the receiver thin walls 475 into the insert grooves 538.

Figure 34:
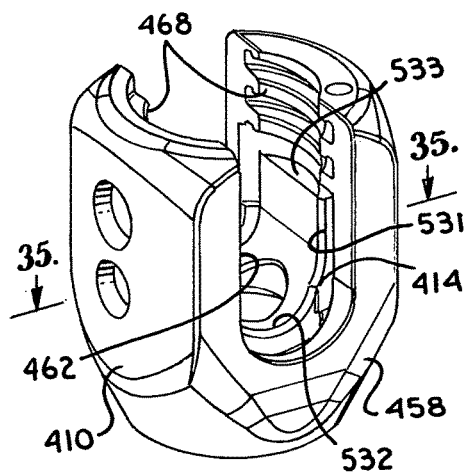
FIG. 34 is a perspective view of the receiver and compression insert of FIG. 33, shown assembled.
Figure 35:
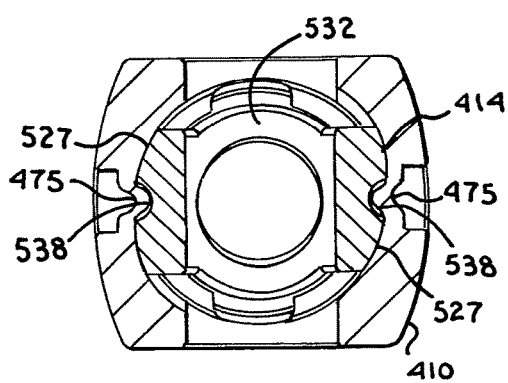
FIG. 35 is a cross-sectional view taken along the line 35-35 of FIG. 34.

Pre-assembly of the compression insert 414 with the receiver 410 and retainer 412 is shown FIGS. 33-36. The compression insert 414 is downloaded (see arrow W) into the receiver 410 with the insert arms 527 located between the opposed receiver arms 460, the insert 414 being lowered toward the receiver base 458 until the insert 414 arm upper surfaces 533 are adjacent the receiver arm inner surfaces 466 located below the guide and advancement structures 468. Thereafter, the insert 414 is rotated in a clockwise direction shown by the arrow X about the receiver axis until the insert stop blocks 540 abut against each of the receiver recess stop walls 470. Such occurs when the upper arm surfaces 533 are directly below the guide and advancement structure 468 of each arm as illustrated in FIG. 34 with the U-shaped channel 531 of the insert 414 aligned with the U-shaped channel 462 of the receiver 410. At this time, the receiver thin crimp walls 475 are pressed inwardly into the insert grooves 538 as shown in FIGS. 35 and 36. At this time, in some embodiments of the invention, frictional engagement between the crimp walls 475 and the insert surfaces grooves 538 may be used to hold the insert 414 in an upper portion of the receiver 410, for example as shown in FIG. 36. In addition to holding the insert 414 in a desired axial position within the receiver 410, the crimping of the walls 475 in the grooves 538 prohibits counter-clockwise rotation of the insert 414 with respect to the receiver 410.

Similar to the description herein with respect to the assembly 1, the bone screw shank 404 or an entire assembly 401 made up of the assembled shank 404, receiver 410, retainer 412 and compression insert 414, is screwed into a bone, such as the vertebra 13, by rotation of the shank 404 using a suitable driving tool (not shown) that operably drives and rotates the shank body 406 by engagement thereof at the internal drive 450 and in a percutaneous or minimally invasive surgical manner, or otherwise as desired. When the shank 404 is driven into the vertebra without the remainder of the assembly 401, the shank 404 may either be driven to a desired final location or may be driven to a location slightly above or proud to provide for ease in assembly with the pre-assembled receiver, compression insert and retainer.

With reference to FIGS. 36-37 (and the discussion previously provided herein with respect to the assembly 1), the pre-assembled receiver, insert and retainer are placed above the shank upper portion 408 and as the shank upper portion 408 is moved into the interior 476 of the receiver base, the shank upper portion 408 presses upwardly against the retainer 412 in the expansion recess partially defined by the cylindrical surface 484. As the portion 408 continues to move upwardly toward the channel 462, the surface 444 forces outward movement of the retainer 412 towards the cylindrical surface 484 in the receiver expansion chamber or area as the shank 404 presses the retainer 412 against the receiver lower annular ledge surface 487. The retainer 412 initially expands about the shank upper spherical surface 444 and then slides along the cylindrical surface 442, snapping or popping into the recessed cylindrical surface 438, the surface 505 of the retainer 412 fully contacting and frictionally engaging the cylindrical surface 438 between the surfaces 434 and 442. At this time, the retainer 412 is in a neutral or slightly expanded state, fully snapped onto the shank upper portion 408 with both the retainer 412 and shank upper portion 408 in pivotal relation with the receiver 410.

With reference to FIG. 37, the shank 404 and attached retainer 412 are then moved downwardly into a desired position with the retainer seated on the surface 480. The insert 414 may slide downwardly with the retainer 412, or in some embodiments, remain in an upper part of the receiver 410 retained by the crimp walls 475 until the insert 414 is pressed downwardly by a tool or by a rod and closure top. In such embodiments, the insert 414 surface 522 is in frictional engagement with the shank upper portion surface 444 to an extent that the shank is pivotable with respect to the receiver, but in a non-floppy manner. In some embodiments, when the receiver 410 is pre-assembled with the shank 404, the entire assembly 401 may be implanted at this time by inserting the driving tool (not shown) into the receiver and the shank drive 450 and rotating and driving the shank 404 into a desired location of the vertebra, such as the previously illustrated vertebra 13.

The rod 421 is eventually positioned in an open or percutaneous manner in cooperation with the at least two bone screw assemblies 401. The closure structure 418 is then inserted into and advanced between the arms 460 of each of the receivers 410. The closure structure 418 is rotated, using a tool engaged with the inner drive 586 until a selected pressure is reached at which point the rod 421 engages the U-shaped seating surface 531 of the compression insert 414. Also, as shown in FIG. 38, the closure top annular base rim 588 engages and presses down upon top surfaces 533 of the insert 414 arms 527, pressing the insert spherical surface 522 against the shank spherical surface 444, that in turn presses the shank upper portion 408 with attached retainer 412 into locked frictional engagement with the receiver 410 independently of any locking pressure placed by the rod 421 onto the insert 414. As the closure structure 418 rotates and moves downwardly into the respective receiver 410, the point or nub 589 and dome 590 engage and penetrate or deform the rod surface 422, the closure structure 418 pressing downwardly against and biasing the rod 421 into compressive engagement with the insert 414 that also urges the shank upper portion 408 and attached retainer 412 into locking engagement with the receiver, the retainer 412 spherical surface 507 frictionally abutting the spherical seating surface 480 of the receiver 410. For example, about 80 to about 120 inch pounds of torque on the closure top may be applied for fixing the bone screw shank 406 with respect to the receiver 410 by direct locking engagement between the closure top 418, the insert 414, the shank upper portion 408 and attached retainer 412 with the receiver seating surface 480. Over- or undue deformation of the deformable rod 421 therefore does not occur because of the direct cooperation between the closure top 418 and the compression insert 414. Also, for example, with reference to FIG. 39, when the shank 404 is disposed at an angle with respect to the receiver 410, the lower spherical surface 434 of the shank upper portion 408 may also be in frictional engagement with a portion of the receiver spherical seating surface 480. The retainer 412 may also expand slightly upon locking, providing a full and secure frictional locking engagement with the receiver at the surface 480.

If removal of the rod 421 from any of the bone screw assemblies 401 is necessary, or if it is desired to release the rod 421 at a particular location, disassembly is accomplished by using the driving tool (not shown) that mates with the internal drive 586 on the closure structure 418 to rotate and remove such closure structure from the cooperating receiver 410. Disassembly is then accomplished in reverse order to the procedure described previously herein for assembly.

With reference to FIGS. 40-47 the reference number 601 generally represents a polyaxial bone screw apparatus or assembly according to the present invention. The assembly 601 includes a shank 604, that further includes a body 606 integral with an upwardly extending upper portion or capture structure 608; a receiver 610; an open retainer structure 612 and a compression or pressure insert 614. FIGS. 40 and 44-47 further show a closure structure 618 of the invention for capturing a longitudinal connecting member, for example, a rod 621 within the receiver 610. The rod 621 having an outer cylindrical surface 622 may be the same or substantially similar to the rod 21 or other longitudinal connecting members previously described herein with respect to the assembly 1. The assembly 601 is substantially identical to the assembly 1 with the exception of a feature of the shank 604 and a feature of the retainer 612. Specifically, the shank 604 does not include a lower spherical surface such as the surface 34 of the shank 4 and the retainer 612 inner cylindrical surface further includes inner vertical grooves.

With particular reference to FIGS. 40-42, the shank 604 is substantially similar in form and function to the shank 4 previously described herein with respect to the assembly 1, and thus includes the shank body 606, upper portion or head 608, a lower cylindrical surface 638, a ledge 640, an upper cylindrical surface 642, an upper spherical surface 644 and an internal drive 650 that are the same or substantially similar in form and function to the respective body 6, upper portion or head 8, cylindrical surface 38, ledge 40, upper cylindrical surface 42, upper spherical surface 44, internal drive 50, and all the other features previously described herein with respect to the shank 4 of the assembly 1 with the exception of the lower spherical surface 34. The shank cylindrical surface 638 extends from the lower ledge 640 to adjacent a neck 626 that joins the shank upper portion 608 with the shank body 606.

With particular reference to FIGS. 40 and 44-47, the receiver 610 is substantially similar to the receiver 10 previously described herein and thus includes a base 658 with integral upstanding arms 660, a U-shaped channel 662, an arm interior substantially cylindrical surface 666, a guide and advancement structure 668, a tool aperture 671 partially defined by a thin crimp wall 675, an inner base cavity or chamber generally 676, a lower cylindrical surface 678, a spherical seating surface 680, a central cylindrical expansion portion 684 and an upper shelf, generally 686, the same or substantially similar in form and function to the respective base 58 with integral upstanding arms 60, U-shaped channel 62, arm interior substantially cylindrical surface 66, guide and advancement structure 68, tool aperture 71, crimp wall 75, inner base cavity or chamber generally 76, lower cylindrical surface 78, spherical seating surface 80, central cylindrical expansion portion 84 and upper shelf, generally 86, and other features previously described herein with respect to the receiver 10 of the assembly 1.

With particular reference to FIGS. 40, 43 and 44, the open, expandable retainer 612 is the same or substantially similar in form and function to the retainer 12 previously described herein with respect to the assembly 1, with the addition of inner grooves. Therefore, the retainer 612 includes a top surface 702, a bottom surface 704, an inner cylindrical surface 705, an outer spherical surface 707 and a through slit 708 that are the same or similar in form and function to the respective top surface 102, bottom surface 104, inner cylindrical surface 105, outer spherical surface 107 and slit formed by end surfaces 109 and 110 previously described herein with respect to the retainer 12. Formed in the inner surface 705 are four equally spaced grooves 715. The grooves 715 aid during the expansion of the retainer 612 and furthermore in resiliency and gripping of the retainer 612 on the shank surface 638. As compared to the retainer 12, the spaced grooves 715 of the retainer 612 provide for a more even expansion during assembly with the shank upper portion 608, resulting in less stress in the area directly opposite the slit 708. The retainer 612 also requires less space for expansion about the upper portion 608 since not all of the expansion is occurring opposite the slit 708, but rather at each of the grooves 715. Less stress during expansion results in a stronger retainer 12 post-expansion.

With reference to FIGS. 40, 44, 45 and 47, the compression insert 614 is substantially similar in form and function to the insert 14 previously described herein with respect to the assembly 1. Therefore, the insert 614 includes an inner cylindrical surface 721, an inner spherical surface 722, a cylindrical body 726, a pair of upstanding arms 727, a U-shaped channel 731 having a lower seat 732, arm top surfaces 733, a bottom surface 735 and arm outer surfaces 737, each with a groove 738 formed therein that are the same or substantially similar in form and function to the respective inner cylindrical surface 121, inner spherical surface 122, cylindrical body 126, upstanding arms 127, U-shaped channel 131 with lower seat 132, arm top surfaces 133, the bottom surface 135 and arm outer surfaces 137 with grooves 138 of the insert 14 previously described herein.

With reference to FIGS. 40 and 44-47, the closure top 618 is identical to the closure top 18 previously described herein with respect to the assembly 1 with the exception of the lower rod contacting surfaces thereof. The closure top 618 has a flange form guide and advancement structure 782, a top surface 784, an internal drive 786, a bottom surface 788, a point 789 and a rim 790 that is the same in form and function to the respective guide and advancement structure 182, top surface 184, internal drive 186, base 188, point 189 and rim 190 of the closure top 18 previously described herein.

The assembly and disassembly, if desired, and implantation and operation of the assembly 601 is performed in a manner identical to what has been described herein with respect to the assembly 1. In operation, the retainer 612 inner surface 705 grips the shank surface 638 with the retainer top surface 702 abutting against the shank ledge 640 as shown, for example, in FIGS. 44-47. The downward force applied on the shank upper spherical surface 644 by the compression insert surface 722 maintains the retainer 612 in engagement with the ledge 640 as the retainer spherical surface 707 is pressed against the receiver seating surface 680 at all desired angles of articulation between the shank 604 and the receiver 610 as shown, for example, in FIG. 47.

Figure 51:
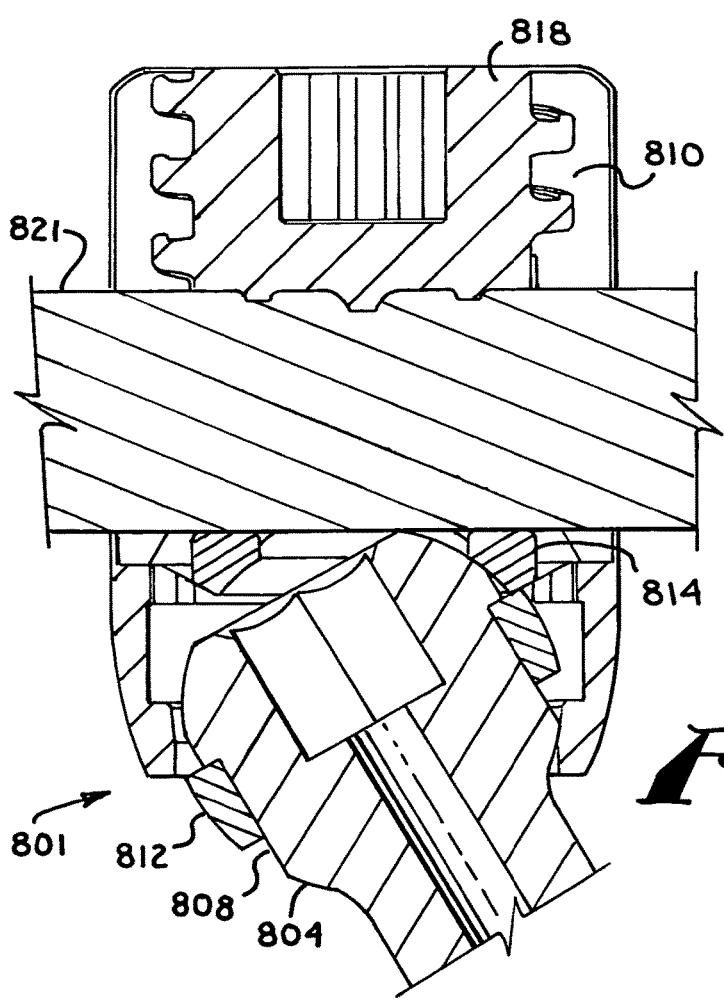
FIG. 51 is an enlarged and partial side elevational view, similar to FIG. 50, with portions broken away to show the detail thereof.

With reference to FIGS. 48-51 the reference number 801 generally represents a polyaxial bone screw apparatus or assembly according to the present invention. The assembly 801 includes a shank 804, that further includes a body 806 integral with an upwardly extending upper portion or capture structure 808; a receiver 810; an open retainer structure 812 and a compression or pressure insert 814. FIGS. 48, 49 and 51 further show a closure structure 818 of the invention for capturing a longitudinal connecting member, for example, a rod 821 within the receiver 810. The rod 821 is the same or substantially similar to the rod 21 or other longitudinal connecting members previously described herein with respect to the assembly 1. The assembly 801 is a combination of the assembly 201 and the assembly 601, both previously described herein. Specifically, the shank 804, the retainer 812 and the closure top 818 are identical or substantially similar to the respective shank 604, retainer 612 and closure top 618 of the assembly 601 while the receiver 810 and the compression insert 814 are identical or substantially similar to the respective receiver 210 and insert 214 of the assembly 201. In other words, the assembly 801 is identical to the previously described assembly 601 with the exception that receiver spring tabs 275 and insert flat surface portions 338 of the assembly 201 have replaced the receiver crimp walls 678 and insert grooves 738 of the assembly 601. The assembly 801 has designated spring tabs 875 and cooperating insert flat surface portions 838. The assembly and disassembly, if desired, and implantation and operation of the assembly 801 is performed in a manner identical to what has been described herein with respect to the assembly 201.

With reference to FIGS. 52-54 the reference number 901 generally represents a polyaxial bone screw apparatus or assembly according to the present invention. The assembly 901 includes a shank 904, that further includes a body 906 integral with an upwardly extending upper portion or capture structure 908; a receiver 910; an open retainer structure 912 and a compression or pressure insert 914. FIGS. 52-54 further show a closure structure 918 of the invention for capturing a longitudinal connecting member, for example, a deformable rod 921 within the receiver 910. The rod 921 is the same or substantially similar to the rod 421 previously described herein with respect to the assembly 401. The assembly 901 is a combination of the assembly 401 and the assembly 601. Specifically, the shank 904 and the retainer 912 are identical or substantially similar to the respective shank 604 and retainer 612 of the assembly 601 while the receiver 910, the compression insert 914 and the closure top 918 are identical or substantially similar to the respective receiver 410, insert 414 and closure top 418 of the assembly 401. The assembly and disassembly, if desired, and implantation and operation of the assembly 901 is performed in a manner identical to what has been described herein with respect to the assembly 401.

With reference to FIGS. 55-58, an alternative open retainer 12' for use with any of the other assemblies described herein is substantially similar to the open retainer 12 previously described herein with the exception of grooves formed in the retainer 12'. Specifically, the retainer 12' includes a top surface 102', a bottom surface 104', an inner cylindrical surface 105', an outer spherical surface 107' and end surfaces 109' and 110' that are the same or similar in form and function to the respective top surface 102, bottom surface 104, inner cylindrical surface 105, outer spherical surface 107 and slit formed by end surfaces 109 and 110 previously described herein with respect to the retainer 12. Furthermore, four evenly spaced grooves 115' are formed in the bottom surface 104' and extend through the inner surface 105' and the outer spherical surface 107' about halfway toward the top surface 102'. It is foreseen that there may be more or fewer groves 115'. The grooves 115' advantageously even out the stress on the retainer 12' during expansion thereof over a shank upper portion 8, 208, 408, 608, 808 or 908 previously described herein. Thus, the grooves 115' aid in making the retainer 12' more strong and resilient, deforming outwardly during expansion in a more even or uniform fashion at the grooves 115', resulting in less stress at the portion of the retainer located directly opposite the slit formed by the end surfaces 109' and 110'.

With reference to FIGS. 59-60 the reference number 1001 generally represents a polyaxial bone screw apparatus or assembly according to the present invention. The assembly 1001 includes a shank 1004, that further includes a body 1006 integral with an upwardly extending upper portion or capture structure 1008; a receiver 1010; an open retainer structure 1012 and a compression or pressure insert 1014. FIGS. 59 and 60 further show a closure structure 1018 of the invention for capturing a longitudinal connecting member, for example, a rod 1021 within the receiver 1010. The rod 1021 is the same or substantially similar to the rod 21 or other longitudinal connecting members previously described herein with respect to the assembly 1. The receiver 1010, the insert 1014, the closure top 1018 and the rod 1021 are identical or substantially similar to the respective receiver 210, insert 214, closure top 218 and rod 221 previously described herein with respect to the assembly 201 shown in FIGS. 21-29 and previously described herein. The shank 1004 and the retainer 1012 are similar to the respective shank 204 and retainer 212 of the assembly 201, but there are some differences. Primarily, the shank and retainer have been modified to have a frusto-conical interface as compared to the cylindrical interface shown between the shank 204 and the retainer 212.

Specifically, the shank 1004, having the shank body 1006 includes a helically wound bone implantable thread 1024 (single or dual lead thread form) extending from near a neck 1026 located adjacent to the upper portion or capture structure 1008, to a tip 1028 of the body 1006 and extending radially outwardly therefrom. The neck 1026 extends axially upward from the shank body 1006. The neck 1026 may be of the same or is typically of a slightly reduced radius as compared to an adjacent upper end or top 1032 of the body 1006 where the thread 1024 terminates. Further extending axially and outwardly from the neck 1026 is the shank upper portion 1008 that provides a connective or capture apparatus disposed at a distance from the upper end 1032 and thus at a distance from a vertebra, such as the vertebra 13 when the body 1006 is implanted in such vertebra.

The shank upper portion 1008 is configured for a pivotable connection between the shank 1004 (with attached retainer 1012) and the receiver 1010 prior to fixing of the shank 1004 in a desired position with respect to the receiver 1010. The shank upper portion 1008 has an outer, convex and substantially spherical lower surface 1034 that extends outwardly and upwardly from the neck 1026 and terminates at a frusto-conical surface 1038. In some embodiments of the invention, the spherical lower surface 1034 has an outer radius that is the same or substantially similar to an outer radius of the retainer 1012 so that the surface 1034 as well as the retainer 1012 outer surface participating in the ball and socket joint formed by the shank 1004 and attached retainer 1012 within the partially spherical surface defining an inner cavity of the receiver 1010. However, in other embodiments, the radius of the shank portion 1034 may be different than a radius of the retainer 1012. Adjacent the spherical surface 1034 is the upwardly and inwardly extending frusto-conical surface 1038. Extending outwardly from the frusto-conical surface 1038 is an annular surface or upper ledge 1040 that faces downwardly toward the frusto-conical surface 1038 and is substantially perpendicular to a central axis of the shank 1004. The frusto-conical surface 1038 and the upper ledge 1040 cooperate to capture and fix the resilient open retainer 1012 to the shank upper portion 1008, prohibiting movement of the retainer 1012 along the shank axis once the retainer 1012 is located beneath ledge 1040. The illustrated frusto-conical surface 1038 is narrower at a top thereof. In other words, a diameter of the surface 1038 near the upper ledge 1040 is smaller than a diameter of the surface 1038 near the lower spherical surface 1034. Extending upwardly from the upper ledge 1040 is a spherical or domed surface 1044. The spherical surface 1044 has an outer radius configured for sliding cooperation and ultimate frictional mating with a substantially spherical concave surface of the compression insert 1014 that has the same or substantially similar radius as the surface 1044. The radius of the surface 1044 is smaller than the radius of the lower spherical surface 1034. Located near or adjacent to the surface 1044 is an annular top surface 1046. A counter sunk internal drive feature 1050 is formed in the top surface 1046 and has a hex shape designed to receive a hex tool (not shown) of an Allen wrench type, into the aperture for rotating and driving the bone screw shank 1004.

The open retainer 1012 that operates to capture the shank upper portion 1008 within the receiver 1010 is made from a resilient material, such as a stainless steel or titanium alloy, so that the retainer 1012 may be expanded during assembly. However, because there is no need to compress the retainer 1012 during assembly, an opening or slit, generally 1108 that allows for expansion of the retainer 1012 is designed to be very narrow, advantageously providing substantial or almost full surface contact between the retainer and the shank upper portion 1008 and also between the retainer and the receiver 1010 seating surface. The retainer 1012 has a central channel or hollow through bore that passes entirely through the structure 1012 from a top surface 1102 to a bottom surface 1104 thereof. The bore is primarily defined by a discontinuous inner frusto-conical surface 1105 that runs from the top surface 1102 to the bottom surface 1104. The retainer 1012 further includes an outer substantially spherical surface 1107 running between the top surface 1102 and the bottom surface 1104, the surface 1107 having the same or similar radius (when the resilient retainer 1012 is in a non-expanded, neutral or near neutral state) as the receiver 1010 seating surface and the shank lower spherical surface 1034 and thus larger than the radius of the dome 1044 of the shank 1004 that engages the similarly radiused lower surface of the insert 1014. The resilient retainer 1012 further includes first and second end surfaces disposed in spaced relation to one another forming the slit 1108 when the retainer is in a neutral or near neutral state.

The assembly 1001 is assembled in a manner similar to the assembly 1, 201 and 601, for example, as previously described herein, with the shank upper portion 1008 being snapped or popped into the receiver 1010 by pushing the shank spherical surface 1044 through the retainer 1012 already located within the receiver inner cavity. As shown in FIG. 60, once assembled, the frusto-conical surface 1038 of the shank 1004 contacts the frusto-conical surface 1105 of the retainer 1012 with the retainer top surface 1102 abutting against the shank ledge surface 1040, providing a secure fit between the shank 1004 and the retainer 1012, the retainer 1012 thus capturing the shank head 1008 within the receiver 1010. Further assembly and disassembly, if desired, and implantation and operation of the assembly 1001 is performed in a manner identical to what has been described herein with respect to the assemblies 1, 201, 601 and 801, for example.

With reference to FIGS. 61-62 the reference number 2001 generally represents another polyaxial bone screw apparatus or assembly according to the present invention. The assembly 2001 includes a shank 2004, that further includes a body 2006 integral with an upwardly extending upper portion or capture structure 2008; a receiver 2010; an open retainer structure 2012 and a compression or pressure insert 2014. FIGS. 61 and 62 further show a closure structure 2018 of the invention for capturing a longitudinal connecting member, for example, a rod 2021 within the receiver 2010. The rod 2021 is the same or substantially similar to the rod 21 or other longitudinal connecting members previously described herein with respect to the assembly 1. The receiver 2010, the insert 2014, the closure top 2018 and the rod 2021 are identical or substantially similar to the respective receiver 10, insert 14, closure top 18 and rod 21 previously described herein with respect to the assembly 1 shown in FIGS. 1-20 and previously described herein. The shank 2004 and the retainer 2012 are similar to the respective shank 4 and retainer 12 of the assembly 1, but there are some differences. Primarily, the shank and retainer have been modified to have a frusto-conical interface as compared to the cylindrical interface shown between the shank 4 and the retainer 12.

Specifically, the shank 2004, having the shank body 2006 includes a helically wound bone implantable thread 2024 (single or dual lead thread form) extending from near a neck 2026 located adjacent to the upper portion or capture structure 2008, to a tip 2028 of the body 2006 and extending radially outwardly therefrom. The neck 2026 extends axially upward from the shank body 2006. The neck 2026 may be of the same or is typically of a slightly reduced radius as compared to an adjacent upper end or top 2032 of the body 2006 where the thread 2024 terminates. Further extending axially and outwardly from the neck 2026 is the shank upper portion 2008 that provides a connective or capture apparatus disposed at a distance from the upper end 2032 and thus at a distance from a vertebra, such as the vertebra 13 when the body 2006 is implanted in such vertebra.

The shank upper portion 2008 is configured for a pivotable connection between the shank 2004 (with attached retainer 2012) and the receiver 2010 prior to fixing of the shank 2004 in a desired position with respect to the receiver 2010. The shank upper portion 2008 has an outer, convex and substantially spherical lower surface 2034 that extends outwardly and upwardly from the neck 2026 and terminates at a lower ledge 2036. The spherical lower surface 2034 has an outer radius that is the same or substantially similar to an outer radius of the retainer 2012, the surface 2034 as well as the retainer 2012 outer surface participating in the ball and socket joint formed by the shank 2004 and attached retainer 2012 within the partially spherical surface defining an inner cavity of the receiver 2010. Adjacent the surface 2034 is the annular, planar lower ledge surface 2036 positioned perpendicular to a central axis of the shank 2004. Extending outwardly and upwardly from the lower ledge 2036 is a frusto-conical surface 2038. Extending from the frusto-conical surface 2038 is an annular surface or upper ledge 2040 that is opposite the lower ledge 2036, and faces downwardly toward the frusto-conical surface 2038, the upper ledge 2040 also being substantially perpendicular to the central axis of the shank 2004. The frusto-conical surface 2038 and the upper and lower ledges 2036 and 2040 cooperate to capture and fix the resilient open retainer 2012 to the shank upper portion 2008, prohibiting movement of the retainer 2012 along the shank axis once the retainer 2012 is located between the ledges 2036 and 2040. The illustrated frusto-conical surface 2038 is narrower at a bottom thereof. In other words, a diameter of the surface 2038 near the upper ledge 2040 is larger than a diameter of the surface 2038 near the bottom ledge 2036. Extending upwardly from the upper ledge 2040 is a spherical or domed surface 2044. The spherical surface 2044 has an outer radius configured for sliding cooperation and ultimate frictional mating with a substantially spherical concave surface of the compression insert 2014 that has the same or substantially similar radius as the surface 2044. The radius of the surface 2044 is smaller than the radius of the lower spherical surface 2034. Located near or adjacent to the surface 2044 is an annular top surface 2046. A counter sunk internal drive feature 2050 is formed in the top surface 2046 and has a hex shape designed to receive a hex tool (not shown) of an Allen wrench type, into the aperture for rotating and driving the bone screw shank 2004.

The open retainer 2012 that operates to capture the shank upper portion 2008 within the receiver 2010 is made from a resilient material, such as a stainless steel or titanium alloy, so that the retainer 2012 may be expanded during assembly. However, because there is no need to compress the retainer 2012 during assembly, an opening or slit, generally 2108 that allows for expansion of the retainer 2012 is designed to be very narrow, advantageously providing substantial or almost full surface contact between the retainer and the shank upper portion 2008 and also between the retainer and the receiver 2010 seating surface. The retainer 2012 has a central channel or hollow through bore that passes entirely through the structure 2012 from a top surface 2102 to a bottom surface 2104 thereof. The bore is primarily defined by a discontinuous inner frusto-conical surface 2105 that runs from the top surface 2102 to the bottom surface 2104. The retainer 2012 further includes an outer substantially spherical surface 2107 running between the top surface 2102 and the bottom surface 2104, the surface 2107 having the same or similar radius (when in a neutral or near neutral state) as the receiver 2010 seating surface and the shank lower spherical surface 2034 and thus larger than the radius of the dome 2044 of the shank 2004 that engages the similarly radiused lower surface of the insert 2014. The resilient retainer 2012 further includes first and second end surfaces disposed in spaced relation to one another forming the slit 2108 when the retainer is in a neutral or near neutral state.

The assembly 2001 is assembled in a manner similar to the assembly 1, for example, as previously described herein, with the shank upper portion 2008 being snapped or popped into the receiver 2010 by pushing the shank spherical surface 2044 through the retainer 2012 already located within the receiver inner cavity. As shown in FIG. 62, once assembled, the frusto-conical surface 2038 of the shank 2004 contacts the frusto-conical surface 2105 of the retainer 2012 with the retainer bottom surface 2104 seated on the shank lower ledge surface 2036 and a portion of the retainer top surface 2102 abutting against the shank upper ledge surface 2040, providing a secure fit between the shank 2004 and the retainer 2012, the retainer 2012 thus capturing the shank head 2008 within the receiver 2010. Further assembly and disassembly, if desired, and implantation and operation of the assembly 2001 is performed in a manner identical to what has been described herein with respect to the assemblies 1, 201, 601 and 801, for example.

With reference to FIGS. 63-64 the reference number 3001 generally represents another polyaxial bone screw apparatus or assembly according to the present invention. The assembly 3001 includes a shank 3004, that further includes a body 3006 integral with an upwardly extending upper portion or capture structure 3008; a receiver 3010; an open retainer structure 3012 and a compression or pressure insert 3014. FIGS. 63 and 64 further show a closure structure 3018 of the invention for capturing a longitudinal connecting member, for example, a rod 3021 within the receiver 3010. The rod 3021 is the same or substantially similar to the rod 21 or other longitudinal connecting members previously described herein with respect to the assembly 1. The receiver 3010, the insert 3014, the closure top 3018 and the rod 3021 are identical or substantially similar to the respective receiver 210, insert 214, closure top 218 and rod 221 previously described herein with respect to the assembly 201 shown in FIGS. 21-29 and previously described herein. The shank 3004 and the retainer 3012 are similar to the respective shank 204 and retainer 212 of the assembly 201, but there are some differences. Primarily, the shank and retainer have been modified to have a sloping and curved interface as compared to the cylindrical interface shown between the shank 204 and the retainer 212.

Specifically, the shank 3004, having the shank body 3006 includes a helically wound bone implantable thread 3024 (single or dual lead thread form) extending from near a neck 3026 located adjacent to the upper portion or capture structure 3008, to a tip 3028 of the body 3006 and extending radially outwardly therefrom. The neck 1026 extends axially upward from the shank body 1006. The neck 3026 may be of the same or is typically of a slightly reduced radius as compared to an adjacent upper end or top 3032 of the body 3006 where the thread 3024 terminates. Further extending axially and outwardly from the neck 3026 is the shank upper portion 3008 that provides a connective or capture apparatus disposed at a distance from the upper end 3032 and thus at a distance from a vertebra, such as the vertebra 13 when the body 3006 is implanted in such vertebra.

The shank upper portion 3008 is configured for a pivotable connection between the shank 31004 (with attached retainer 3012) and the receiver 3010 prior to fixing of the shank 3004 in a desired position with respect to the receiver 3010. The shank upper portion 3008 has an outer, convex and substantially spherical lower surface 3034 that extends outwardly and upwardly from the neck 3026 and terminates at a curved surface 3038. The spherical lower surface 3034 has an outer radius that is the same or substantially similar to an outer radius of the retainer 3012 so that the surface 3034 as well as the retainer 3012 outer surface participating in the ball and socket joint formed by the shank 3004 and attached retainer 3012 within the partially spherical surface defining an inner cavity of the receiver 3010. Adjacent the spherical surface 3034 the an upwardly and inwardly extending curved surface of revolution 3038 formed about a central axis of the shank 3004, the illustrated surface 3038 being somewhat trumpet-like in form, having at least one and up to a plurality a radii. Extending outwardly from the surface 3038 is an annular surface or upper ledge 3040 that faces downwardly toward the curved surface 3038 and is substantially perpendicular to the central axis of the shank 3004. The curved surface 3038 and the upper ledge 3040 cooperate to capture and fix the resilient open retainer 3012 to the shank upper portion 3008, prohibiting movement of the retainer 3012 along the shank axis once the retainer 3012 is located beneath ledge 3040. The illustrated curved surface 3038 is narrower at a top thereof. In other words, a diameter of the surface 3038 near the upper ledge 3040 is smaller than a diameter of the surface 3038 near the lower spherical surface 3034. Extending upwardly from the upper ledge 3040 is a spherical or domed surface 3044. The spherical surface 3044 has an outer radius configured for sliding cooperation and ultimate frictional mating with a substantially spherical concave surface of the compression insert 3014 that has the same or substantially similar radius as the surface 3044. The radius of the surface 3044 is smaller than the radius of the lower spherical surface 3034. Located near or adjacent to the surface 3044 is an annular top surface 3046. A counter sunk internal drive feature 3050 is formed in the top surface 3046 and has a hex shape designed to receive a hex tool (not shown) of an Allen wrench type, into the aperture for rotating and driving the bone screw shank 3004.

The open retainer 3012 that operates to capture the shank upper portion 3008 within the receiver 3010 is made from a resilient material, such as a stainless steel or titanium alloy, so that the retainer 3012 may be expanded during assembly. However, because there is no need to compress the retainer 3012 during assembly, an opening or slit, generally 3108 that allows for expansion of the retainer 3012 is designed to be very narrow, advantageously providing substantial or almost full surface contact between the retainer and the shank upper portion 3008 and also between the retainer and the receiver 3010 seating surface. The retainer 3012 has a central channel or hollow through bore that passes entirely through the structure 3012 from a top surface 3102 to a bottom surface 3104 thereof. The bore is primarily defined by a discontinuous inner curved surface of rotation 3105 that runs from the top surface 3102 to the bottom surface 3104. The retainer 3012 further includes an outer substantially spherical surface 3107 running between the top surface 3102 and the bottom surface 3104, the surface 3107 having the same or similar radius (when the resilient retainer 3012 is in a non-expanded, neutral or near neutral state) as the receiver 3010 seating surface and the shank lower spherical surface 3034 and thus larger than the radius of the dome 3044 of the shank 3004 that engages the similarly radiused lower surface of the insert 3014. The resilient retainer 3012 further includes first and second end surfaces disposed in spaced relation to one another forming the slit 3108 when the retainer is in a neutral or near neutral state.

The assembly 3001 is assembled in a manner similar to the assembly 1, 201 and 601, for example, as previously described herein, with the shank upper portion 3008 being snapped or popped into the receiver 3010 by pushing the shank spherical surface 3044 through the retainer 3012 already located within the receiver inner cavity. As shown in FIG. 64, once assembled, the curved surface 3038 of the shank 3004 matches and is in mating contact with the curved surface 3105 of the retainer 3012 with a portion of the retainer top surface 3102 abutting against the shank ledge surface 3040, providing a secure fit between the shank 3004 and the retainer 3012, the retainer 3012 thus capturing the shank head 3008 within the receiver 3010. Further assembly and disassembly, if desired, and implantation and operation of the assembly 3001 is performed in a manner identical to what has been described herein with respect to the assemblies 1, 201, 601 and 801, for example.

With reference to FIGS. 65-66 the reference number 4001 generally represents another polyaxial bone screw apparatus or assembly according to the present invention. The assembly 4001 includes a shank 4004, that further includes a body 4006 integral with an upwardly extending upper portion or capture structure 4008; a receiver 4010; an open retainer structure 4012 and a compression or pressure insert 4014. FIGS. 65 and 66 further show a closure structure 4018 of the invention for capturing a longitudinal connecting member, for example, a rod 4021 within the receiver 4010. The rod 4021 is the same or substantially similar to the rod 21 or other longitudinal connecting members previously described herein with respect to the assembly 1. The receiver 4010, the insert 4014, the closure top 4018 and the rod 4021 are identical or substantially similar to the respective receiver 10, insert 14, closure top 18 and rod 21 previously described herein with respect to the assembly 1 shown in FIGS. 1-20 and previously described herein. The shank 4004 and the retainer 4012 are similar to the respective shank 4 and retainer 12 of the assembly 1, but there are some differences. Primarily, the shank and retainer have been modified to have a curved, surface of rotation interface as compared to the cylindrical interface shown between the shank 4 and the retainer 12.

Specifically, the shank 4004, having the shank body 4006 includes a helically wound bone implantable thread 4024 (single or dual lead thread form) extending from near a neck 4026 located adjacent to the upper portion or capture structure 4008, to a tip 4028 of the body 4006 and extending radially outwardly therefrom. The neck 4026 extends axially upward from the shank body 4006. The neck 4026 may be of the same or of a slightly reduced radius as compared to an adjacent upper end or top 4032 of the body 4006 where the thread 4024 terminates. Further extending axially and outwardly from the neck 4026 is the shank upper portion 4008 that provides a connective or capture apparatus disposed at a distance from the upper end 4032 and thus at a distance from a vertebra, such as the vertebra 13 when the body 4006 is implanted in such vertebra.

The shank upper portion 4008 is configured for a pivotable connection between the shank 4004 (with attached retainer 4012) and the receiver 4010 prior to fixing of the shank 4004 in a desired position with respect to the receiver 4010. The shank upper portion 4008 has an outer, convex and substantially spherical lower surface 4034 that extends outwardly and upwardly from the neck 4026 and terminates at an annular surface 4036. The spherical lower surface 4034 has an outer radius that is the same or substantially similar to an outer radius of the retainer 4012, the surface 4034 as well as the retainer 4012 outer surface participating in the ball and socket joint formed by the shank 4004 and attached retainer 4012 within the partially spherical surface defining an inner cavity of the receiver 4010. Adjacent the surface 4034 is the annular, planar lower ledge surface 4036 positioned perpendicular to a central axis of the shank 4004. Extending outwardly and upwardly from the lower ledge 4036 is a curved surface of rotation 4038 formed about the shank central axis. Unlike the trumpet like surface 3038 previously described with respect to the assembly 3001, the surface 4038 is uniform, defined by a curve with a single radius. Extending from the curved surface 4038 is an annular surface or upper ledge 4040 that is opposite the lower ledge 4036, and faces downwardly toward the curved surface 4038, the upper ledge 4040 also being substantially perpendicular to the central axis of the shank 4004. The curved surface 4038 and the upper and lower ledges 4036 and 4040 cooperate to capture and fix the resilient open retainer 4012 to the shank upper portion 4008, prohibiting movement of the retainer 4012 along the shank axis once the retainer 4012 is located between the ledges 4036 and 4040. Extending upwardly from the upper ledge 4040 is a spherical or domed surface 4044. The spherical surface 4044 has an outer radius configured for sliding cooperation and ultimate frictional mating with a substantially spherical concave surface of the compression insert 4014 that has the same or substantially similar radius as the surface 4044. The radius of the surface 4044 is smaller than the radius of the lower spherical surface 4034 and the outer radius of the retainer 4012. Located near or adjacent to the surface 4044 is an annular top surface 4046. A counter sunk internal drive feature 4050 is formed in the top surface 4046 and has a hex shape designed to receive a hex tool (not shown) of an Allen wrench type, into the aperture for rotating and driving the bone screw shank 4004.

The open retainer 4012 that operates to capture the shank upper portion 4008 within the receiver 4010 is made from a resilient material, such as a stainless steel or titanium alloy, so that the retainer 4012 may be expanded during assembly. However, because there is no need to compress the retainer 4012 during assembly, an opening or slit, generally 4108 that allows for expansion of the retainer 4012 is designed to be very narrow, advantageously providing substantial or almost full surface contact between the retainer and the shank upper portion 4008 and also between the retainer and the receiver 4010 seating surface. The retainer 4012 has a central channel or hollow through bore that passes entirely through the structure 4012 from a top surface 4102 to a bottom surface 4104 thereof. The bore is primarily defined by a discontinuous inner curved surface 4105 that runs from the top surface 4102 to the bottom surface 4104. The retainer 4012 further includes an outer substantially spherical surface 4107 running between the top surface 4102 and the bottom surface 4104, the surface 4107 having the same or similar radius (when in a neutral or near neutral state) as the receiver 4010 seating surface and the shank lower spherical surface 4034 and thus larger than the radius of the dome 4044 of the shank 4004 that engages the insert 4014. The resilient retainer 4012 further includes first and second end surfaces disposed in spaced relation to one another forming the slit 4108 when the retainer is in a neutral or near neutral state.

The assembly 4001 is assembled in a manner similar to the assembly 1, for example, as previously described herein, with the shank upper portion 4008 being snapped or popped into the receiver 4010 by pushing the shank spherical surface 4044 through the retainer 4012 already located within the receiver inner cavity. As shown in FIG. 66, once assembled, the curved surface 4038 of the shank 4004 aligns and closely contacts the curved surface 4105 the retainer 4012 with the retainer bottom surface 4104 seated on the shank lower ledge surface 4036 and a portion of the retainer top surface 4102 abutting against the shank upper ledge surface 4040, providing a secure fit between the shank 4004 and the retainer 4012, the retainer 4012 thus capturing the shank head 4008 within the receiver 4010. Further assembly and disassembly, if desired, and implantation and operation of the assembly 4001 is performed in a manner identical to what has been described herein with respect to the assemblies 1, 201, 601 and 801, for example.

With reference to FIGS. 67-68 the reference number 5001 generally represents another polyaxial bone screw apparatus or assembly according to the present invention. The assembly 5001 includes a shank 5004, that further includes a body 5006 integral with an upwardly extending upper portion or capture structure 5008; a receiver 5010; an open retainer structure 5012 and a compression or pressure insert 5014. FIGS. 67 and 68 further show a closure structure 5018 of the invention for capturing a longitudinal connecting member, for example, a rod 5021 within the receiver 5010. The rod 5021 is the same or substantially similar to the rod 21 or other longitudinal connecting members previously described herein with respect to the assembly 1. The receiver 5010, the insert 5014, the closure top 5018 and the rod 5021 are substantially similar to the respective receiver 10, insert 14, closure top 18 and rod 21 previously described herein with respect to the assembly 1 shown in FIGS. 1-20 and previously described herein. It is noted that to accommodate the slightly taller retainer 5012, the receiver 5010 interior has also been slightly modified to create a slightly taller inner expansion chamber for the expansion of the retainer 5012 about the shank head 5008 within such chamber. The shank 5004 and the retainer 5012 are similar to the respective shank 4 and retainer 12 of the assembly 1, but there are some differences. Primarily, the shank and retainer have been modified to provide an assembly wherein the retainer 5012 has an outer radius that is the same as an upper outer radius of the shank 5010 that in turn engages the insert 5014 at a lower concave surface thereof, also having the same radius.

Specifically, the shank 5004, having the shank body 5006 includes a helically wound bone implantable thread 5024 (single or dual lead thread form) extending from near a neck 5026 located adjacent to the upper portion or capture structure 5008, to a tip 5028 of the body 5006 and extending radially outwardly therefrom. The neck 5026 extends axially upward from the shank body 5006. The neck 5026 may be of the same or of a slightly reduced radius as compared to an adjacent upper end or top 5032 of the body 5006 where the thread 5024 terminates. Further extending axially and outwardly from the neck 5026 is the shank upper portion 5008 that provides a connective or capture apparatus disposed at a distance from the upper end 5032 and thus at a distance from a vertebra, such as the vertebra 13 when the body 5006 is implanted in such vertebra.

The shank upper portion 5008 is configured for a pivotable connection between the shank 5004 (with attached retainer 5012) and the receiver 5010 prior to fixing of the shank 5004 in a desired position with respect to the receiver 5010. The shank upper portion 5008 has an outer, convex and substantially spherical lower surface 5034 that extends outwardly and upwardly from the neck 5026 and terminates at an annular surface 5036. The spherical lower surface 5034 has an outer radius that is the same or substantially similar to an outer radius of the retainer 5012, the surface 5034 as well as the retainer 5012 outer surface participating in the ball and socket joint formed by the shank 5004 and attached retainer 5012 within the partially spherical surface defining an inner cavity of the receiver 5010. Adjacent the surface 5034 is the annular, planar lower ledge surface 5036 positioned perpendicular to a central axis of the shank 5004. Extending upwardly from the lower ledge 5036 is a cylindrical surface 5038 formed about the shank central axis. Extending from the cylindrical surface 5038 is an annular surface or upper ledge 5040 that is opposite the lower ledge 5036, the upper ledge 5040 also being substantially perpendicular to the central axis of the shank 5004. The cylindrical surface 5038 and the upper and lower ledges 5036 and 5040 cooperate to capture and fix the resilient open retainer 5012 to the shank upper portion 5008, prohibiting movement of the retainer 5012 along the shank axis once the retainer 5012 is located between the ledges 5036 and 5040. Extending upwardly from the upper ledge 5040 is a spherical or domed surface 5044. The spherical surface 5044 has an outer radius configured for sliding cooperation and ultimate frictional mating with a substantially spherical concave surface of the compression insert 5014 that has the same or substantially similar radius as the surface 5044. The radius of the surface 5044 is the same or substantially the same as the radius of the lower spherical surface 5034 and the outer radius of the retainer 5012. Located near or adjacent to the surface 5044 is an annular top surface 5046. A counter sunk internal drive feature 5050 is formed in the top surface 5046 and has a hex shape designed to receive a hex tool (not shown) of an Allen wrench type, into the aperture for rotating and driving the bone screw shank 5004.

The open retainer 5012 that operates to capture the shank upper portion 5008 within the receiver 5010 is made from a resilient material, such as a stainless steel or titanium alloy, so that the retainer 5012 may be expanded during assembly. However, because there is no need to compress the retainer 5012 during assembly, an opening or slit, generally 5108 that allows for expansion of the retainer 5012 is designed to be very narrow, advantageously providing substantial or almost full surface contact between the retainer and the shank upper portion 5008 and also between the retainer and the receiver 5010 seating surface. The retainer 5012 has a central channel or hollow through bore that passes entirely through the structure 5012 from a top surface 5102 to a bottom surface 5104 thereof. The bore is primarily defined by a discontinuous inner cylindrical surface 5105 that runs from the top surface 5102 to the bottom surface 5104. The retainer 5012 further includes an outer substantially spherical surface 5107 running between the top surface 5102 and the bottom surface 5104, the surface 5107 having the same or similar radius (when in a neutral or near neutral state) as the receiver 5010 seating surface and the shank lower spherical surface 5034 and thus the same radius as the dome 5044 of the shank 5004 that engages the insert 5014. The resilient retainer 5012 further includes first and second end surfaces disposed in spaced relation to one another forming the slit 5108 when the retainer is in a neutral or near neutral state.

The assembly 5001 is assembled in a manner similar to the assembly 1, for example, as previously described herein, with the shank upper portion 5008 being snapped or popped into the receiver 5010 by pushing the shank spherical surface 5044 through the retainer 5012 already located within the receiver inner cavity. As shown in FIG. 68, once assembled, the cylindrical surface 5038 of the shank 5004 aligns and closely contacts the cylindrical surface 5105 the retainer 5012 with the retainer bottom surface 5104 seated on the shank lower ledge surface 5036 and the retainer top surface 5102 abutting against the shank upper ledge surface 5040, providing a secure fit between the shank 5004 and the retainer 5012, the retainer 5012 thus capturing the shank head 5008 within the receiver 5010. Further assembly and disassembly, if desired, and implantation and operation of the assembly 5001 is performed in a manner identical to what has been described herein with respect to the assemblies 1, 201, 601 and 801, for example.

With reference to FIGS. 69-70 the reference number 6001 generally represents a polyaxial bone screw apparatus or assembly according to the present invention. The assembly 6001 includes a shank 6004, that further includes a body 6006 integral with an upwardly extending upper portion or capture structure 6008; a receiver 6010; an open retainer structure 6012 and a compression or pressure insert 6014. FIGS. 69 and 70 further show a closure structure 6018 of the invention for capturing a longitudinal connecting member, for example, a rod 6021 within the receiver 6010. The rod 6021 is the same or substantially similar to the rod 21 or other longitudinal connecting members previously described herein with respect to the assembly 1. The receiver 6010, the insert 6014, the closure top 6018 and the rod 6021 are identical or substantially similar to the respective receiver 210, insert 214, closure top 218 and rod 221 previously described herein with respect to the assembly 201 shown in FIGS. 21-29 and previously described herein. It is noted that the receiver 6010 has been slightly modified to accommodate the retainer 6012 that is taller than the retainer 212. The shank 6004 and the retainer 6012 are similar to the respective shank 204 and retainer 212 of the assembly 201, but there are some differences. Primarily, the shank and retainer have been modified to have a frusto-conical interface as compared to the cylindrical interface shown between the shank 204 and the retainer 212. Furthermore, the shank and retainer have been modified to provide an assembly wherein the retainer 6012 has an outer radius that is the same as an upper outer radius of the shank 6010 that in turn engages the insert 6014 at a lower concave surface thereof, also having the same radius.

Specifically, the shank 6004, having the shank body 6006 includes a helically wound bone implantable thread 6024 (single or dual lead thread form) extending from near a neck 6026 located adjacent to the upper portion or capture structure 6008, to a tip 6028 of the body 6006 and extending radially outwardly therefrom. The neck 6026 extends axially upward from the shank body 6006. The neck 6026 may be of the same or is typically of a slightly reduced radius as compared to an adjacent upper end or top 6032 of the body 6006 where the thread 6024 terminates. Further extending axially and outwardly from the neck 6026 is the shank upper portion 6008 that provides a connective or capture apparatus disposed at a distance from the upper end 6032 and thus at a distance from a vertebra, such as the vertebra 13 when the body 6006 is implanted in such vertebra.

The shank upper portion 6008 is configured for a pivotable connection between the shank 6004 (with attached retainer 6012) and the receiver 6010 prior to fixing of the shank 6004 in a desired position with respect to the receiver 6010. The shank upper portion 6008 has an outer, convex and substantially spherical lower surface 6034 that extends outwardly and upwardly from the neck 6026 and terminates at a cylindrical surface 6036. The spherical lower surface 6034 has an outer radius that is the same or substantially similar to an outer radius of the retainer 6012 so that the surface 6034 as well as the retainer 6012 outer surface participating in the ball and socket joint formed by the shank 6004 and attached retainer 6012 within the partially spherical surface defining an inner cavity of the receiver 6010. However, in other embodiments, the radius of the shank portion 6034 may be different than a radius of the retainer 6012. Adjacent the cylindrical surface 6036 is an upwardly and inwardly extending frusto-conical surface 6038. Extending outwardly from the frusto-conical surface 6038 is an annular surface or upper ledge 6040 that faces downwardly toward the frusto-conical surface 6038 and is substantially perpendicular to a central axis of the shank 6004. The frusto-conical surface 6038 and the upper ledge 6040 cooperate to capture and fix the resilient open retainer 6012 to the shank upper portion 6008, prohibiting movement of the retainer 6012 along the shank axis once the retainer 6012 is located beneath ledge 6040. The illustrated frusto-conical surface 6038 is narrower at a top thereof. In other words, a diameter of the surface 6038 near the upper ledge 6040 is smaller than a diameter of the surface 6038 near the lower spherical surface 6034. Extending upwardly from the upper ledge 6040 is a cylindrical surface 6042 followed by a spherical or domed surface 6044. The spherical surface 6044 has an outer radius configured for sliding cooperation and ultimate frictional mating with a substantially spherical concave surface of the compression insert 6014 that has the same or substantially similar radius as the surface 6044. The radius of the surface 6044 is the same or substantially similar to the radius of the lower spherical surface 6034 and the outer spherical surface of the retainer 6012. Located near or adjacent to the surface 6044 is an annular top surface 6046. A counter sunk internal drive feature 6050 is formed in the top surface 6046 and has a hex shape designed to receive a hex tool (not shown) of an Allen wrench type, into the aperture for rotating and driving the bone screw shank 6004.

The open retainer 6012 that operates to capture the shank upper portion 6008 within the receiver 6010 is made from a resilient material, such as a stainless steel or titanium alloy, so that the retainer 6012 may be expanded during assembly. However, because there is no need to compress the retainer 6012 during assembly, an opening or slit, generally 6108 that allows for expansion of the retainer 6012 is designed to be very narrow, advantageously providing substantial or almost full surface contact between the retainer and the shank upper portion 6008 and also between the retainer and the receiver 6010 seating surface. The retainer 6012 has a central channel or hollow through bore that passes entirely through the structure 6012 from a top surface 6102 to a bottom surface 6104 thereof. The bore is primarily defined by a discontinuous inner frusto-conical surface 6105 that runs from the top surface 6102 to the bottom surface 6104. The retainer 6012 further includes an outer substantially spherical surface 6107 running between the top surface 6102 and the bottom surface 6104, the surface 6107 having the same or similar radius (when the resilient retainer 6012 is in a non-expanded, neutral or near neutral state) as the receiver 6010 seating surface, the shank lower spherical surface 6034 and the dome 6044 of the shank 6004 that engages the similarly radiused lower surface of the insert 6014. The resilient retainer 6012 further includes first and second end surfaces disposed in spaced relation to one another forming the slit 6108 when the retainer is in a neutral or near neutral state.

The assembly 6001 is assembled in a manner similar to the assembly 1, 201 and 601, for example, as previously described herein, with the shank upper portion 6008 being snapped or popped into the receiver 6010 by pushing the shank spherical surface 6044 through the retainer 6012 already located within the receiver inner cavity. As shown in FIG. 70, once assembled, the frusto-conical surface 6038 of the shank 6004 closely contacts the frusto-conical surface 6105 of the retainer 6012 along an entire surface thereof with a portion of the retainer top surface 6102 abutting against the shank ledge surface 6040, providing a secure fit between the shank 6004 and the retainer 6012, the retainer 6012 thus capturing the shank head 6008 within the receiver 6010. Further assembly and disassembly, if desired, and implantation and operation of the assembly 6001 is performed in a manner identical to what has been described herein with respect to the assemblies 1, 201, 601 and 801, for example.

With reference to FIGS. 71-72 the reference number 7001 generally represents a polyaxial bone screw apparatus or assembly according to the present invention. The assembly 7001 includes a shank 7004, that further includes a body 7006 integral with an upwardly extending upper portion or capture structure 7008; a receiver 7010; an open retainer structure 7012 and a compression or pressure insert 7014. FIGS. 71 and 72 further show a closure structure 7018 of the invention for capturing a longitudinal connecting member, for example, a rod 7021 within the receiver 7010. The rod 7021 is the same or substantially similar to the rod 21 or other longitudinal connecting members previously described herein with respect to the assembly 1. The receiver 7010, the insert 7014, the closure top 7018 and the rod 7021 are identical or substantially similar to the respective receiver 210, insert 214, closure top 218 and rod 221 previously described herein with respect to the assembly 201 shown in FIGS. 21-29. It is noted that the receiver 7010 has been slightly modified to accommodate the retainer 7012 that is taller than the retainer 212. The shank 7004 and the retainer 7012 are similar to the respective shank 204 and retainer 212 of the assembly 201, but there are some differences. Primarily, the shank and retainer have been modified to have a combination frusto-conical and cylindrical interface as compared to the cylindrical interface shown between the shank 204 and the retainer 212. Furthermore, the shank and retainer have been modified to provide an assembly wherein the retainer 7012 has an outer radius that is the same as an upper outer radius of the shank 7010 that in turn engages the insert 7014 at a lower concave surface thereof, also having the same radius.

Specifically, the shank 7004, having the shank body 7006 includes a helically wound bone implantable thread 7024 (single or dual lead thread form) extending from near a neck 7026 located adjacent to the upper portion or capture structure 7008, to a tip 7028 of the body 7006 and extending radially outwardly therefrom. The neck 7026 extends axially upward from the shank body 7006. The neck 7026 may be of the same or slightly reduced radius as compared to an adjacent upper end or top 7032 of the body 7006 where the thread 7024 terminates. Further extending axially and outwardly from the neck 7026 is the shank upper portion 7008 that provides a connective or capture apparatus disposed at a distance from the upper end 7032 and thus at a distance from a vertebra, such as the vertebra 13 when the body 7006 is implanted in such vertebra.

The shank upper portion 7008 is configured for a pivotable connection between the shank 7004 (with attached retainer 7012) and the receiver 7010 prior to fixing of the shank 7004 in a desired position with respect to the receiver 7010. The shank upper portion 7008 has an outer, convex and substantially spherical lower surface 7034 that extends outwardly and upwardly from the neck 7026 and terminates at a cylindrical surface 7035. The spherical lower surface 7034 has an outer radius that is the same or substantially similar to an outer radius of the retainer 7012 so that the surface 7034 as well as the retainer 7012 outer surface participating in the ball and socket joint formed by the shank 7004 and attached retainer 7012 within the partially spherical surface defining an inner cavity of the receiver 7010. However, in other embodiments, the radius of the shank portion 7034 may be different than a radius of the retainer 7012. Adjacent the cylindrical surface 7035 is an annular surface 7036 disposed perpendicular to a central axis of the shank 7004. The surface 7036 is in turn adjacent to an upwardly and inwardly extending frusto-conical surface 7038. Extending outwardly from the frusto-conical surface 7038 is an annular surface or upper ledge 7040 that faces downwardly toward the frusto-conical surface 7038 and is substantially perpendicular to the central axis of the shank 7004. The cylindrical surface 7035, lower ledge 7036, frusto-conical surface 7038 and upper ledge 7040 cooperate to capture and fix the resilient open retainer 7012 to the shank upper portion 7008, prohibiting movement of the retainer 7012 along the shank axis once the retainer 7012 is located beneath ledge 7040. The illustrated frusto-conical surface 7038 is narrower at a top thereof. In other words, a diameter of the surface 7038 near the upper ledge 7040 is smaller than a diameter of the surface 7038 near the cylindrical surface 7035. Extending upwardly from the upper ledge 7040 is a cylindrical surface 7042 followed by a spherical or domed surface 7044. The spherical surface 7044 has an outer radius configured for sliding cooperation and ultimate frictional mating with a substantially spherical concave surface of the compression insert 7014 that has the same or substantially similar radius as the surface 7044. The radius of the surface 7044 is the same or substantially similar to the radius of the lower spherical surface 7034 and the outer spherical surface of the retainer 7012. Located near or adjacent to the surface 7044 is an annular top surface 7046. A counter sunk internal drive feature 7050 is formed in the top surface 7046 and has a hex shape designed to receive a hex tool (not shown) of an Allen wrench type, into the aperture for rotating and driving the bone screw shank 7004.

The open retainer 7012 that operates to capture the shank upper portion 7008 within the receiver 7010 is made from a resilient material, such as a stainless steel or titanium alloy, so that the retainer 7012 may be expanded during assembly. However, because there is no need to compress the retainer 7012 during assembly, an opening or slit, generally 7108 that allows for expansion of the retainer 7012 is designed to be very narrow, advantageously providing substantial or almost full surface contact between the retainer and the shank upper portion 7008 and also between the retainer and the receiver 7010 seating surface. The retainer 7012 has a central channel or hollow through bore that passes entirely through the structure 7012 from a top surface 7102 to a bottom surface 7104 thereof. The bore is primarily defined by a discontinuous inner frusto-conical surface 7105 that runs from the top surface 7102 to a cylindrical surface 7106 that in turn is adjacent to the bottom surface 7104. The retainer 7012 further includes an outer substantially spherical surface 7107 running between the top surface 7102 and the bottom surface 7104, the surface 7107 having the same or similar radius (when the resilient retainer 7012 is in a non-expanded, neutral or near neutral state) as the receiver 7010 seating surface, the shank lower spherical surface 7034 and the dome 7044 of the shank 7004 that engages the similarly radiused lower surface of the insert 7014. The resilient retainer 7012 further includes first and second end surfaces disposed in spaced relation to one another forming the slit 7108 when the retainer is in a neutral or near neutral state.

The assembly 7001 is assembled in a manner similar to the assembly 1, 201 and 601, for example, as previously described herein, with the shank upper portion 7008 being snapped or popped into the receiver 7010 by pushing the shank spherical surface 7044 through the retainer 7012 already located within the receiver inner cavity. As shown in FIG. 72, once assembled, the frusto-conical surface 7038 of the shank 7004 closely contacts the frusto-conical surface 7105 of the retainer 7012 along an entire surface thereof with a portion of the retainer top surface 7102 abutting against the shank ledge surface 7040. Also, the retainer inner cylindrical surface 7106 closely mates with the shank outer cylindrical surface 7035, with a portion of the retainer being seated on the ledge surface 7036. Such a plurality of closely contacting surfaces provides a secure fit between the shank 7004 and the retainer 7012, the retainer 7012 thus capturing the shank head 7008 within the receiver 7010. Further assembly and disassembly, if desired, and implantation and operation of the assembly 7001 is performed in a manner identical to what has been described herein with respect to the assemblies 1, 201, 601 and 801, for example.

It is to be understood that while certain forms of the present invention have been illustrated and described herein, it is not to be limited to the specific forms or arrangement of parts described and shown.

What is claimed and desired to be secured by Letters Patent is as follows:

1. A pivoting bone anchor assembly, comprising:
   a receiver defining a chamber communicating with a first channel, the first channel sized and shaped for receiving a portion of a longitudinal connecting member, the chamber communicating with a receiver bottom opening, the receiver chamber having a spherical seating surface adjacent the bottom opening and an upper expansion region, the first channel opening onto a top of the receiver;
   a shank having a lower portion integral with an upper portion extending along a longitudinal axis, the upper portion including a circumferential capture recess with an external interface surface, the upper portion further including a first radiused surface above the recess and a second radiused surface below the recess;
   an insert positioned within the receiver and configured to engage the shank upper portion; and
   a resilient open retainer having an internal interface surface and a third radiused surface, the retainer being expandable over the first radiused surface and snapping into the shank capture recess within the upper expansion region of the receiver chamber, with the retainer internal interface surface frictionally engaging the shank external interface surface to maintain the retainer in an expanded state, when the shank upper portion is bottom loaded into the receiver chamber through the receiver bottom opening,
   wherein the second radiused surface and the third radiused surface align to define a partially spherical bearing surface to pivotably engage the spherical seating surface when the retainer internal interface surface is frictionally engaged with the shank external interface surface, and wherein both the insert and the retainer are top-loaded into the receiver before the shank upper portion is bottom-loaded into the receiver chamber through the bottom opening.

2. The pivoting bone anchor assembly of claim 1, wherein the insert is configured to engage both the shank upper portion and the retainer third radiused surface.

3. The pivoting bone anchor assembly of claim 1, wherein the shank circumferential capture recess is defined by an upper annular ledge and a lower annular ledge and the retainer has at least a first top planar surface engaging the shank upper annular ledge.

4. The pivoting bone anchor assembly of claim 1, wherein the receiver has at least one of a crimped wall surface and a spring tab pressing onto one or more arms of the insert.

5. The pivoting bone anchor assembly of claim 1, wherein the insert has a second channel and is top loaded into the receiver and rotated into position above the retainer after the retainer is positioned in the receiver chamber, with the insert second channel rotating into alignment with the receiver first channel.

6. The pivoting bone anchor assembly of claim 1, wherein the insert is top loaded into the receiver and rotated into position above the retainer after the retainer is positioned in the receiver chamber, with the insert having a blocking feature configured to inhibit further rotation of the insert within the receiver once an insert second channel becomes aligned with the first channel.

7. The pivoting bone anchor assembly of claim 1, wherein the retainer is a discontinuous ring forming a slit.

8. The pivoting bone anchor assembly of claim 7, wherein the ring has at least one planar surface.

9. The pivoting bone anchor assembly of claim 1, wherein the circumferential capture recess of the shank is frusto-conical having a diameter near the shank first radiused surface and a wider diameter near the shank second radiused surface.

10. The pivoting bone anchor assembly of claim 1, wherein the insert has a pair of arms forming a second channel and a partially spherical bottom surface in engagement with the shank first radiused surface, the insert being located between the shank upper portion and the first channel for receiving in the second channel the portion of the longitudinal connecting member that is also receivable in the first channel.

11. The pivoting bone anchor assembly of claim 1, wherein the first, second, and third radiused surfaces align to define a partially spherical bearing surface configured to pivotably engage both the receiver spherical seating surface and a partially spherical bottom surface of the insert.

12. The pivoting bone anchor assembly of claim 1, wherein the retainer is positioned within the receiver before the insert and the insert is positioned within the receiver before the shank.

13. A pivoting bone anchor, comprising:
a receiver defining a chamber communicating with a channel, the channel sized and shaped for receiving a portion of a rod, the chamber communicating with a lower opening;
a shank having a threaded body integral with an upper portion including a circumferential capture recess with an external interface surface bounded by a downward-facing upper ledge and an upward-facing lower ledge, the upper portion further including a first convex surface above the upper ledge and a second convex surface below the lower ledge, the shank upper portion being upwardly loadable into the receiver through the lower opening with the shank body extending out of and downwardly from the receiver lower opening;
a rod engaging insert being located within the receiver channel prior to the upward loading of the shank into the receiver; and
a resilient open retainer being located in the receiver chamber prior to upward loading of the shank, the retainer having a nominal shape with a third convex outer surface, the retainer being expandable in the chamber about the shank upper portion and receiving the first convex surface therethrough to capture the shank upper portion in the chamber, with a retainer internal interface surface snapping into frictional engagement with the shank external interface surface to maintain the retainer in an expanded state, the interface surfaces having at least one of cylindrical, frusto-conical and curved geometry, the retainer and shank being joined relative to one another and in pivotal relationship with a receiver sidewall surface prior to locking of the retainer against the receiver,
wherein the second convex surface and the third convex surface align to define a partially spherical bearing surface when the retainer internal interface surface is frictionally engaged with the shank external interface surface, and
wherein the pivoting bone anchor is configured for assembly with the retainer being downwardly top loaded into the receiver followed by the insert being downwardly top loaded into the receiver followed by the shank upper portion being upwardly bottom loaded into the receiver.

14. The pivoting bone anchor of claim 13, wherein the insert is spaced from the retainer in all angular orientations of the shank with respect to the receiver.

15. The pivoting bone anchor of claim 13, wherein the insert has an outer surface engaging an inner surface of the receiver.

16. The pivoting bone anchor of claim 15, wherein the receiver has at least one of a crimped wall surface and a spring tab pressing onto the insert.

17. The pivoting bone anchor of claim 13, wherein the receiver channel is a first channel and the insert has a second channel, the insert being top loaded into the receiver and then rotated into a position above the retainer with the second channel aligned with the first channel.

18. The pivoting bone anchor of claim 13, wherein the receiver channel is a first channel and the insert has a second channel, the insert is rotated into position above the retainer, the insert having a blocking feature and the receiver having a stop for abutment with the blocking feature when the second channel is aligned with the first channel.

19. The pivoting bone anchor of claim 13, wherein the retainer is a discontinuous ring forming a through slit, the ring having from none to a plurality of grooves.

20. The pivoting bone anchor of claim 19, wherein the ring has at least one planar surface.

21. The pivoting bone anchor of claim 13,
wherein the shank external interface surface further comprises curved geometry that defines a concave surface; and
wherein the retainer internal interface surface further comprises a curved geometry that defines a convex inner surface mating with the conclave surface.

22. The pivoting bone anchor of claim 13, wherein the insert has a partially spherical bottom surface radiused to mate with the shank upper portion and the retainer, the insert partially spherical bottom surface being in engagement with at least a portion of the shank first convex surface and the retainer third convex outer surface, the insert located between the shank upper portion and the receiver channel for receiving the portion of the rod located in the receiver channel.

23. A pivoting bone anchor assembly comprising:
a receiver defining a chamber communicating with a first channel, the first channel sized and shaped for receiving a portion of a longitudinal connecting member, the chamber communicating with a lower opening and having a lower spherical seating surface portion and an upper expansion portion;
a shank having a threaded body integral with an upper portion, the upper portion having a first curved surface portion located adjacent an annular top of the upper portion and a mid-portion located beneath the first curved surface portion, the mid-portion being adjacent to an upper and a lower planar annular surface, the upper planar annular surface being adjacent to the first curved surface portion, the mid-portion having an interface surface, the interface surface having one of cylindrical, frusto-conical and curvate profile, the lower planar annular surface being adjacent to the interface surface, the shank body extending out of and downwardly from the receiver lower opening;
a resilient open retainer configured for top loading into the chamber upper expansion portion prior to the shank upper portion, the retainer having a top surface, the retainer expandable in the chamber upper expansion portion about the shank upper portion and receiving the first curved surface portion therethrough to capture the shank upper portion in the chamber, the retainer snapping into the shank mid-portion with the retainer top surface abutting the shank upper planar annular surface and a retainer interface surface frictionally engaging the shank interface surface to maintain the retainer in an expanded state, the retainer and shank being in fixed relation to one another and in pivotal relationship with the receiver prior to locking of the retainer against the receiver lower spherical seating surface; and
a top loaded insert having a pair of arms forming a second channel, the insert being in engagement with the shank first curved surface portion, the insert located between the shank upper portion and the first channel for receiving the portion of the longitudinal connecting member located in the receiver channel, the portion of the longitudinal connecting member being received in the second channel,
wherein the retainer is positioned within the chamber after which the insert is positioned within the first channel above the retainer, followed by the shank upper portion being uploaded into the chamber through the lower opening and captured by the retainer.

24. A pivoting bone anchor, comprising:
a receiver defining a chamber communicating with a receiver channel, the receiver channel sized and shaped for receiving a portion of a longitudinal connecting member, the chamber communicating with a lower opening;
a shank having a threaded body integral with an upper portion including a circumferential capture recess with an external interface surface bounded by a downward-facing upper annular surface and an upward-facing lower annular surface, the upper portion having a first convex surface above the upper annular surface and a second convex surface below the lower annular surface, the shank upper portion being positioned into the receiver through the receiver lower opening;
a resilient open retainer configured for top-loading into the chamber, the retainer having a third convex surface, the retainer being expandable in the chamber about the shank upper portion and receiving the first convex surface therethrough to snap onto and capture the shank upper portion in the chamber with a retainer internal interface surface that is frictionally engaged with the shank external interface surface to maintain the retainer in an expanded state, the internal and external interface surfaces being at least one of cylindrical, frusto-conical and curved geometry, the retainer and shank being in fixed relation to one another and in pivotal relationship with the receiver prior to locking of the retainer against the receiver within the chamber; and
a top loaded insert having a lower surface in engagement with at least a portion of the shank first convex surface, the insert located between the shank upper portion and the receiver channel for receiving the portion of the longitudinal connecting member located in the receiver channel,
wherein the retainer and insert are positioned within the receiver before the shank.

25. A pivoting bone anchor comprising:
a receiver defining a chamber communicating with a channel, the receiver channel being sized and shaped for receiving a portion of a longitudinal connecting member, the chamber communicating with a lower opening;
a shank having a threaded body integral with an upper portion and a first axis being located centrally and parallel to the body, the shank extending out of and downwardly from the receiver lower opening, the shank upper portion having a first convex surface and being bottom loaded into the chamber through the lower opening;
a resilient and open retainer configured for top-loading into the receiver chamber prior to the bottom loading of the shank, the retainer having a second convex outer surface, the retainer being expandable in the chamber about the shank upper portion and receiving at least a portion of the first convex surface therethrough to snap onto and capture the shank upper portion in the chamber, the retainer being frictionally joined to the shank at an interface surface located along the shank upper portion adjacent the first convex surface and in an expanded state, the interface surface being frustoconical defined as tapering from a smaller diameter to a larger diameter toward the shank body, the retainer and shank being attached to one another and in pivotal relationship with respect to the receiver prior to locking of the retainer and shank within the receiver chamber; and
a top loaded insert, the insert having a lower surface radiused to mate with the shank first convex surface and the retainer second convex outer surface, the insert being located between the shank upper portion and the receiver channel for receiving the portion of the longitudinal connecting member located in the receiver channel,
wherein both the retainer and the insert ere positioned within the receiver prior to the shank.

26. A pivoting bone anchor comprising:
a receiver defining a chamber communicating with a channel, the receiver channel being sized and shaped for receiving a portion of a longitudinal connecting member, the chamber communicating with a lower opening;

a shank having a threaded body integral with an upper portion and a first axis being located centrally and parallel to the body, the shank extending out of and downwardly from the receiver lower opening, the shank upper portion having a first convex surface and being bottom loaded into the chamber through the lower opening;

a resilient and open retainer top loaded into the chamber prior to bottom loading of the shank, the retainer having a second convex outer surface, the retainer being expandable in the chamber by being pushed up against an abutment surface within the chamber, wherein the retainer snaps onto the shank upper portion to capture the shank upper portion in the chamber, the retainer being frictionally joined to the shank at an interface surface located along the shank upper portion adjacent the first convex surface and in an expanded state, the interface surface being frustoconical defined as tapering from a smaller diameter to a larger diameter toward the shank body, the retainer and shank being attached to one another and in a pivotal relationship with respect to a receiver sidewall surface prior to locking of the retainer against the receiver; and an insert top loaded into the receiver channel and having a lower surface radiused to mate with the shank first convex outer surface and the retainer second convex surface, the insert being located between the shank upper portion and the receiver channel for receiving the portion of the longitudinal connecting member located in the receiver channel, wherein both the retainer and insert are positioned within the receiver prior to the shank.

27. A pivoting bone anchor assembly, comprising:

a receiver defining a chamber communicating with a first channel, the first channel sized and shaped for receiving a portion of a longitudinal connecting member, the chamber communicating with a lower opening;

a shank having a lower bone anchor portion and an upper portion, the upper portion having a first curved surface located near a top of the upper portion, the shank upper portion being configured for bottom loading into the receiver chamber through the receiver lower opening with the lower bone anchor portion extending out of and downwardly from the receiver lower opening;

a resilient open retainer being top loaded into the chamber, the retainer expandable in the chamber about the shank upper portion and receiving the first curved surface therethrough to snap onto and capture the shank upper portion in the chamber, the retainer being frictionally engaged to the shank at en inset interface located along the shank upper portion between the first curved surface and the shank lower bone anchor portion to maintain the retainer in an expanded state, the inset interface defining upper and lower annular shelf surfaces, wherein the lower annular shelf surface has a greater radius than the upper annular shelf surface, the retainer positioned below the first curved surface, the retainer and shank being in fixed relation to one another and m pivotal relationship with the receiver prior to locking of the retainer against the receiver; and an insert being top loaded into the receiver after the retainer, wherein the retainer and the insert are both positioned within the receiver prior to the shank upper portion being bottom loaded into the receiver chamber through the receiver lower opening.

28. The pivoting bone anchor of claim 27, wherein the retainer has an outer second curved surface with a second radius larger than that of the first curved surface.

29. The pivoting bone anchor assembly of claim 27, wherein the top loaded insert further comprises a lower surface radiused to mate and engage with the shank upper portion and the retainer and configured for engagement with at least one of a portion of the shank first curved surface and a retainer third curved surface when the insert is located between the shank upper portion and the portion of the longitudinal connecting member located in the receiver channel.

30. The pivoting bone anchor assembly of claim 27, further comprising the shank upper portion first curved surface having a first radius with respect to a first axis extending longitudinally through the shank, the shank upper portion having a second curved surface below the inset interface having a second radius with respect to the first axis, and the retainer having an outer third curved surface having a third radius with respect to the first axis, and wherein the third radius is substantially equal to the first and second radiuses.

31. The pivoting bone anchor assembly of claim 27, further comprising the shank upper portion first curved surface having a first radius with respect to a first axis extending longitudinally through the shank, the shank upper portion having a second curved surface below the inset interface having a second radius with respect to the first axis, and the retainer having an outer third curved surface having a third radius with respect to the first axis, and wherein the third radius is different from the first and second radiuses.

* * * * *